(12) United States Patent
Anvari

(10) Patent No.: US 12,239,570 B2
(45) Date of Patent: Mar. 4, 2025

(54) SLEEP APNEA DETECTION AND MITIGATION DEVICE

(71) Applicant: Kiomars Anvari, Walnut Creek, CA (US)

(72) Inventor: Kiomars Anvari, Walnut Creek, CA (US)

(73) Assignee: Kiomars Anvari, Walnut Creek, CA (US)

( * ) Notice: Subject to any disclaimer, the term of this patent is extended or adjusted under 35 U.S.C. 154(b) by 0 days.

(21) Appl. No.: 18/814,647

(22) Filed: Aug. 26, 2024

(65) Prior Publication Data

US 2024/0415691 A1    Dec. 19, 2024

Related U.S. Application Data

(63) Continuation-in-part of application No. 18/635,236, filed on Apr. 15, 2024, and a continuation-in-part of
(Continued)

(51) Int. Cl.
| | |
|---|---|
| *A62B 7/10* | (2006.01) |
| *A61F 5/56* | (2006.01) |
| *A61G 13/12* | (2006.01) |
| *A61M 16/00* | (2006.01) |
| *A61M 16/06* | (2006.01) |

(Continued)

(52) U.S. Cl.
CPC ............ *A61F 5/56* (2013.01); *A61G 13/1215* (2013.01); *A61G 13/1265* (2013.01); *A61M 16/0066* (2013.01); *A61M 16/024* (2017.08); *A61M 16/06* (2013.01); *A61M 16/0883* (2014.02); *A61M 16/1065* (2014.02); *A61M 16/107* (2014.02); *A61M 2016/0033* (2013.01); *A61M 2202/0208* (2013.01); *A61M 2205/8206* (2013.01); *A61M 2205/8237* (2013.01); *A61M 2209/088* (2013.01); *A61M 2230/42* (2013.01)

(58) Field of Classification Search
CPC ....... A61B 7/10; A62B 18/003; A62B 18/006; A62B 18/02; A62B 18/025; A62B 18/04; A62B 18/045; A62B 18/08; A62B 18/084; A62B 23/00; A62B 23/02; A41D 13/1153; A61M 16/105
See application file for complete search history.

(56) References Cited

U.S. PATENT DOCUMENTS

| | | | | |
|---|---|---|---|---|
| 2,318,790 A | * | 5/1943 | Martindale ............ | A41D 13/11 128/206.16 |
| 2,758,307 A | * | 8/1956 | Treiber .............. | A41D 13/1184 2/9 |

(Continued)

*Primary Examiner* — LaToya M Louis

(57) ABSTRACT

Sleep apnea detection and mitigation equipment that uses a face mask connected to a pillow with an embedded device is described. The embedded device has an air inlet assembly to pull in air from the environment, an exhaust assembly to release air to the environment, a control circuit, and an oxygen tank with a regulator. The inlet assembly releases filtered air into the face mask through an air tube and the exhaust assembly pulls contaminated air from the interior of the face mask through another air tube. Airflow sensors within the path of the airflow are used to measure the real time airflow data. The control circuit uses the measured real time airflow data to detect sleep apnea. The control circuit also reshapes the pillow to mitigate the apnea.

13 Claims, 48 Drawing Sheets

Related U.S. Application Data application No. 18/436,349, filed on Feb. 8, 2024, now Pat. No. 12,076,596.

(51) Int. Cl.
  *A61M 16/08* (2006.01)
  *A61M 16/10* (2006.01)

(56) References Cited

U.S. PATENT DOCUMENTS

| | | | | |
|---|---|---|---|---|
| 3,921,223 A | * | 11/1975 | Hoyecki | A61F 9/068 2/9 |
| H1361 H | * | 10/1994 | Tardiff, Jr. | B32B 27/12 2/205 |
| 5,490,502 A | * | 2/1996 | Rapoport | A61M 16/026 128/207.18 |
| 7,481,221 B2 | * | 1/2009 | Kullik | A61M 16/0009 128/204.11 |
| 7,578,013 B2 | * | 8/2009 | Aikman | A47C 20/026 5/636 |
| 7,828,524 B2 | * | 11/2010 | Chen | F04D 25/084 415/206 |
| 8,261,742 B2 | * | 9/2012 | Strothmann | A61M 16/026 128/204.26 |
| 9,248,248 B2 | * | 2/2016 | Virr | A61M 16/0066 |
| 10,477,976 B2 | * | 11/2019 | North | A47G 9/10 |
| 10,537,754 B1 | * | 1/2020 | Vukelja | A62B 18/003 |
| 10,874,151 B1 | * | 12/2020 | Clark | A41D 13/0025 |
| 11,324,902 B1 | * | 5/2022 | Esplin | A61M 16/1005 |
| 11,471,711 B2 | * | 10/2022 | Connor | A62B 18/08 |
| 2005/0028250 A1 | * | 2/2005 | Zaic | A42B 3/16 2/209 |
| 2005/0229557 A1 | * | 10/2005 | Little | A47C 7/383 55/385.1 |
| 2005/0267595 A1 | * | 12/2005 | Chen | A61F 5/0036 623/23.65 |
| 2005/0268912 A1 | * | 12/2005 | Norman | A61M 16/0069 128/204.23 |
| 2008/0092894 A1 | * | 4/2008 | Nicolazzi | A61B 5/6814 128/204.23 |
| 2008/0222813 A1 | * | 9/2008 | Aikman | A47C 20/027 340/870.11 |
| 2008/0237287 A1 | * | 10/2008 | Mitchinson | A45F 3/04 224/645 |
| 2009/0050154 A1 | * | 2/2009 | Strothmann | A61M 16/161 128/204.23 |
| 2009/0127304 A1 | * | 5/2009 | Uygur | A45F 5/02 224/250 |
| 2009/0178202 A1 | * | 7/2009 | Kovalyak | A47D 15/008 5/655 |
| 2011/0079225 A1 | * | 4/2011 | Vole | A61M 15/08 128/206.24 |
| 2013/0227768 A1 | * | 9/2013 | Van Waes | A42B 3/185 2/10 |
| 2014/0124528 A1 | * | 5/2014 | Fangrow | A61J 1/2096 222/1 |
| 2014/0196187 A1 | * | 7/2014 | Beliveau | A41D 13/11 2/9 |
| 2014/0245539 A1 | * | 9/2014 | Ooba | A47C 27/083 5/636 |
| 2014/0261428 A1 | * | 9/2014 | Chen | A62B 23/02 128/205.12 |
| 2015/0290479 A1 | * | 10/2015 | Augustine | A62B 23/02 128/200.28 |
| 2016/0058134 A1 | * | 3/2016 | Blunt | A44C 15/005 454/329 |
| 2017/0361134 A1 | * | 12/2017 | Virr | A62B 18/082 |
| 2018/0001120 A1 | * | 1/2018 | Virr | B01D 46/009 |
| 2018/0042409 A1 | * | 2/2018 | Johnson | A61G 13/121 |
| 2018/0078798 A1 | * | 3/2018 | Fabian | A62B 18/10 |
| 2018/0318540 A1 | * | 11/2018 | Barlow | A61M 16/0683 |
| 2019/0091436 A1 | * | 3/2019 | Hsueh | C02F 1/4618 |
| 2020/0114178 A1 | * | 4/2020 | Waterford | A62B 23/025 |
| 2020/0289773 A1 | * | 9/2020 | Zachar | A61M 16/0003 |
| 2020/0289777 A1 | * | 9/2020 | Bearne | A61M 16/06 |
| 2020/0397087 A1 | * | 12/2020 | Crenshaw | A41D 1/002 |
| 2020/0406069 A1 | * | 12/2020 | Fu | A62B 18/025 |
| 2021/0077762 A1 | * | 3/2021 | Mauger | A61M 16/107 |
| 2021/0093903 A1 | * | 4/2021 | Edwards | A62B 18/006 |
| 2021/0339058 A1 | * | 11/2021 | Connor | A62B 18/08 |
| 2021/0345694 A1 | * | 11/2021 | Volk | A41D 13/1161 |
| 2021/0345702 A1 | * | 11/2021 | Volk | A41D 13/11 |
| 2021/0379312 A1 | * | 12/2021 | Bernard | B29C 45/1676 |
| 2022/0008760 A1 | * | 1/2022 | Chen | A62B 18/088 |
| 2022/0023790 A1 | * | 1/2022 | Lee | A62B 18/003 |
| 2022/0118288 A1 | * | 4/2022 | Space | F24F 8/80 |
| 2022/0143344 A1 | * | 5/2022 | Mauger | A61L 9/20 |
| 2022/0161065 A1 | * | 5/2022 | Tindall | A62B 18/084 |
| 2022/0266068 A1 | * | 8/2022 | Connor | A62B 7/10 |
| 2022/0305301 A1 | * | 9/2022 | Yoon | A62B 18/025 |
| 2022/0339377 A1 | * | 10/2022 | Esplin | A61M 16/0003 |
| 2022/0387829 A1 | * | 12/2022 | Mattila | A62B 18/006 |
| 2023/0011058 A1 | * | 1/2023 | Squires | A62B 18/025 |

* cited by examiner

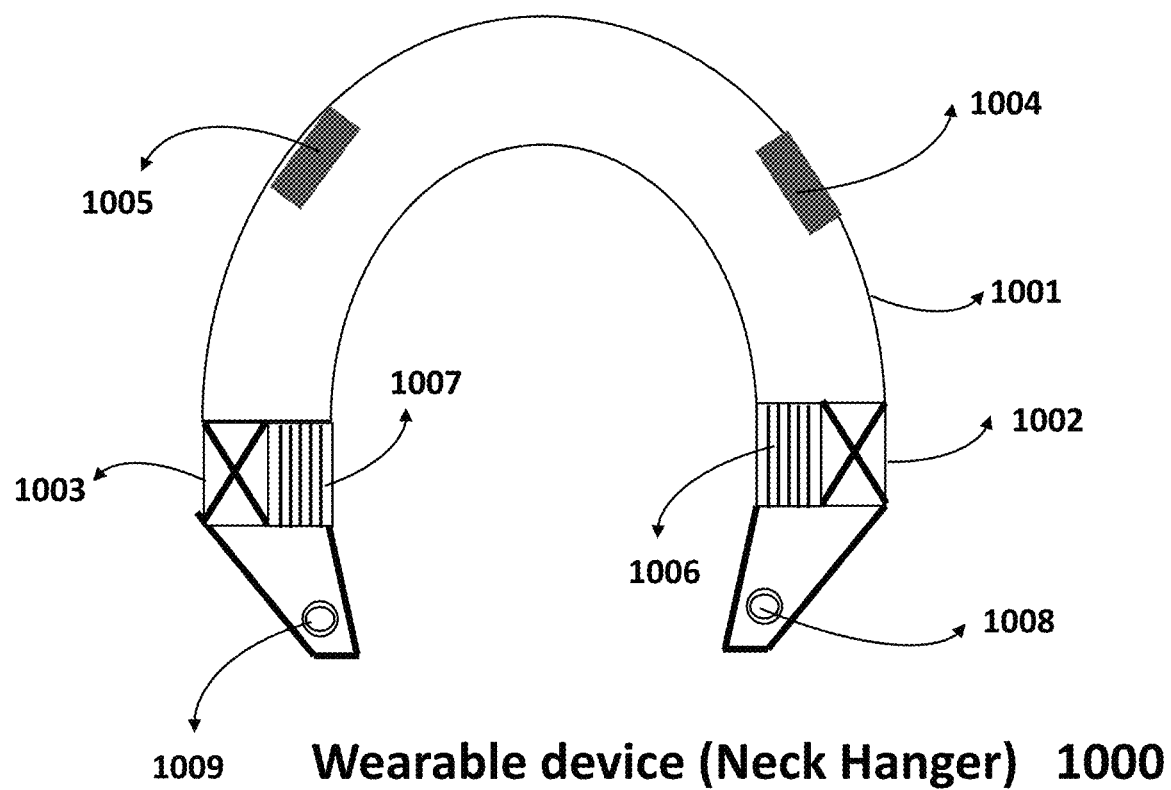

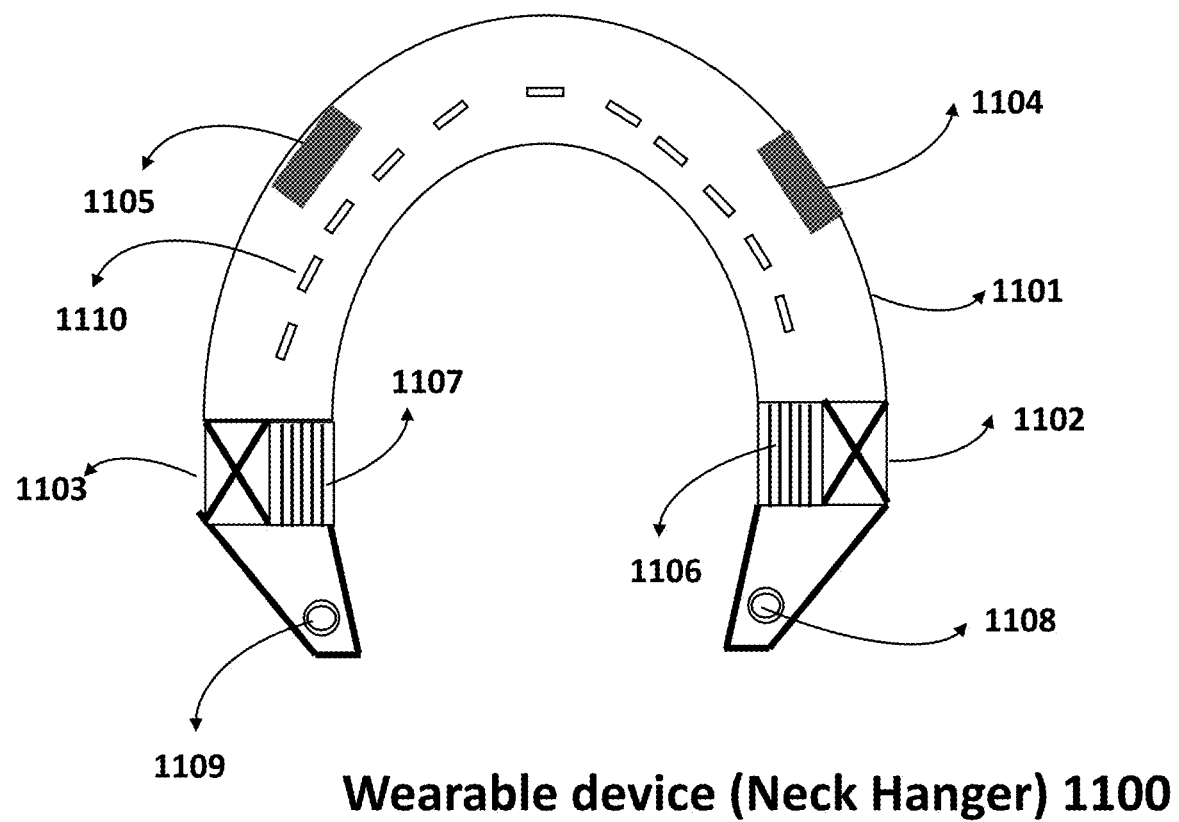

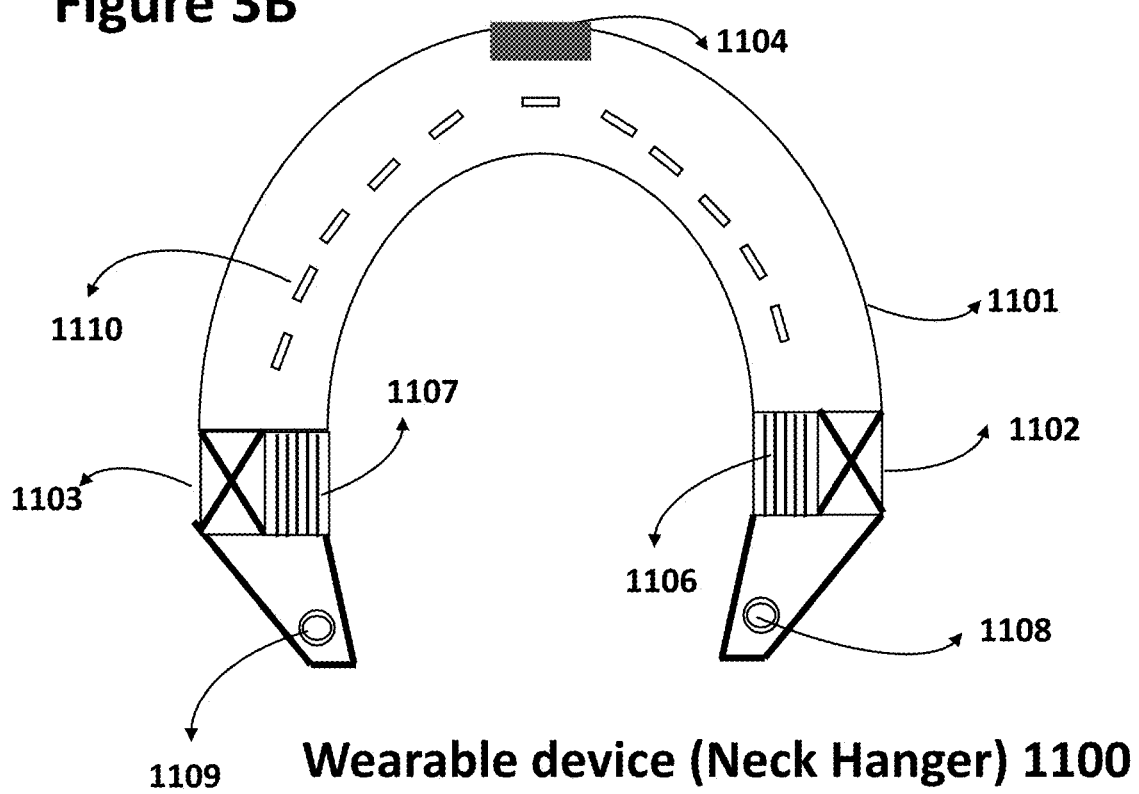

Wearable device (Neck Hanger) 1200

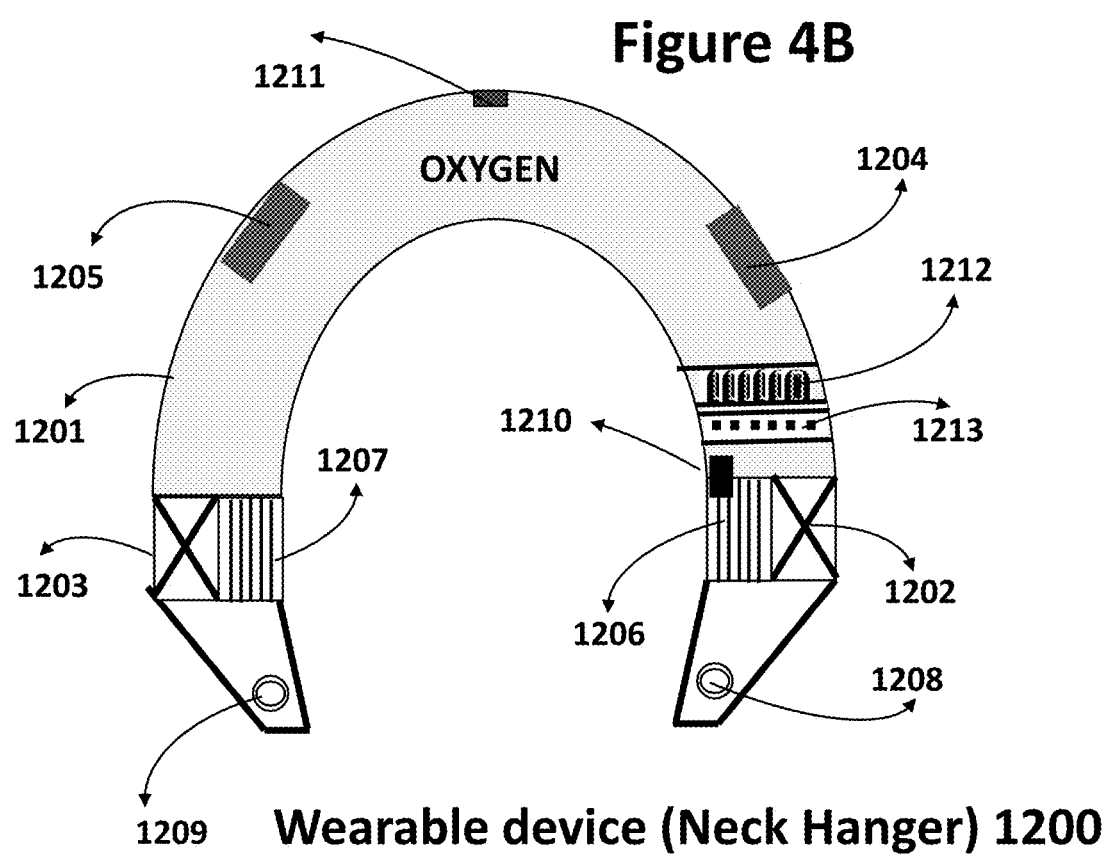

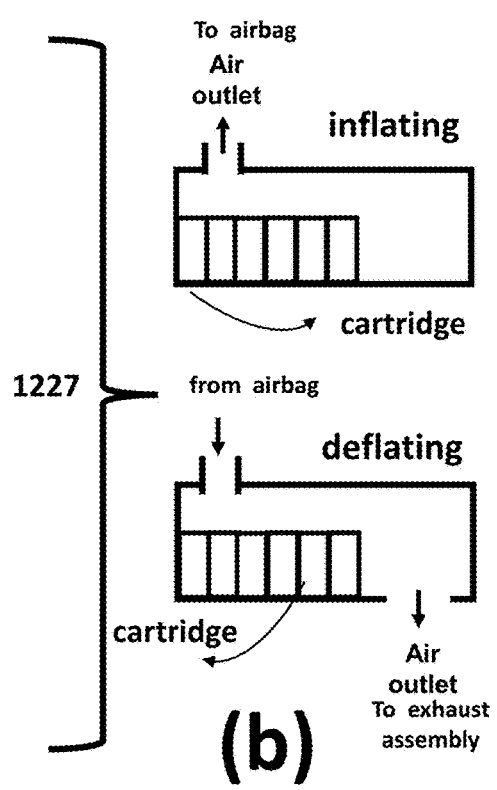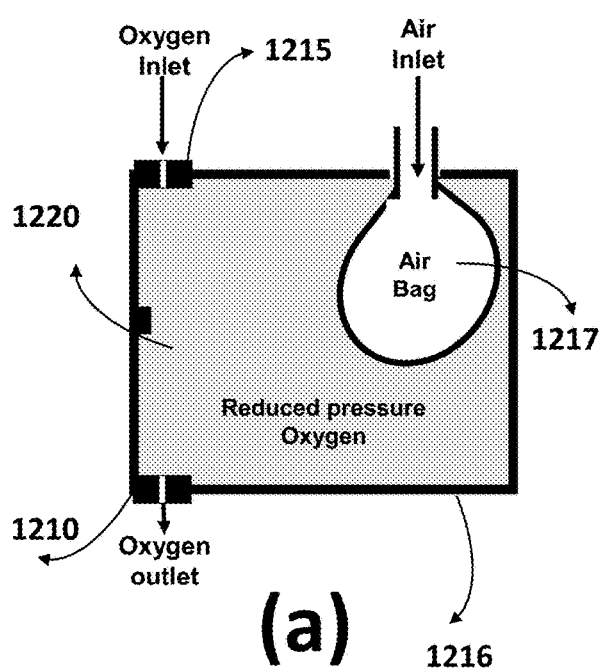
Figure 4L

Wearable device (Neck hanger) Figure on the right shows a detail of wearable device (Neck hanger) figure on the left Figure on the right shows a detail of wearable device (Neck hanger) attached to the mask on the left figure Figure on the right shows a detail of wearable device (Neck hanger) attached to the mask on the left figure

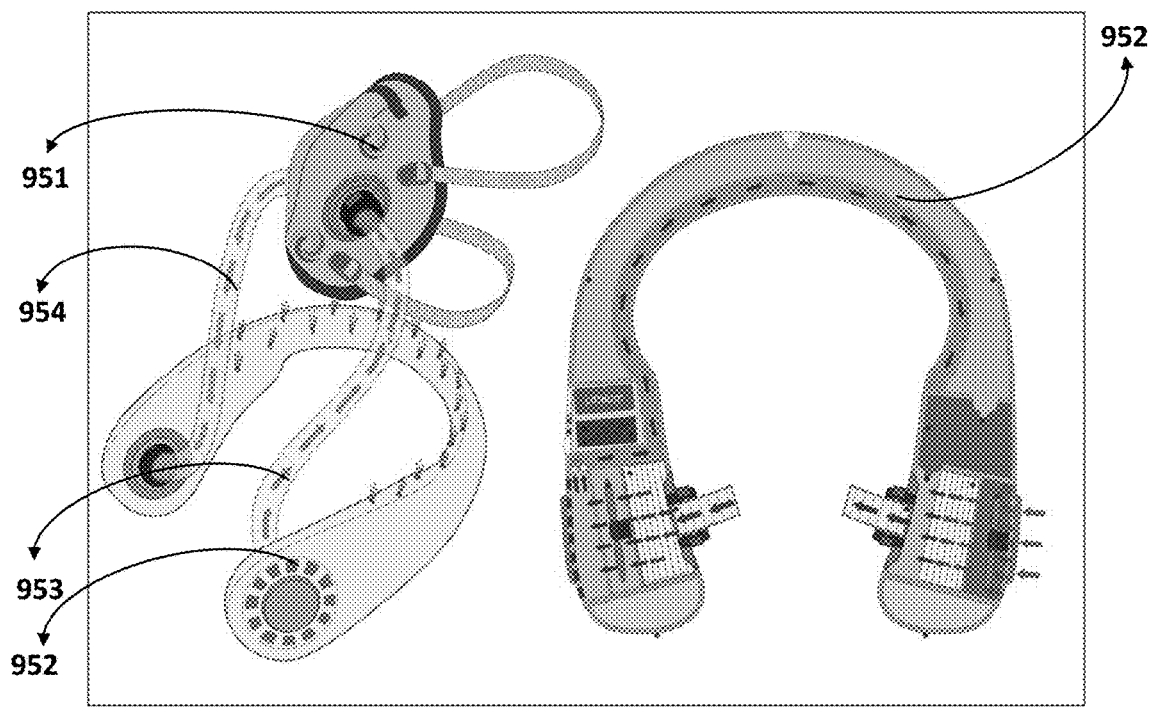
Figure on the right shows a detail of wearable device (Neck hanger) attached to the mask on the left figure Smart phone on the left communicates wirelessly with the face mask with wearable device (Neck hanger) on the right figure

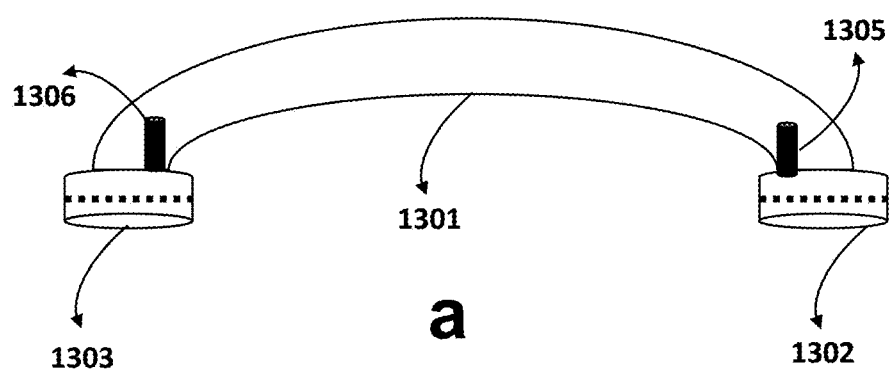
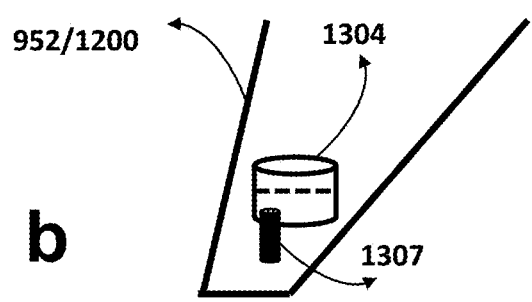
Figure 10

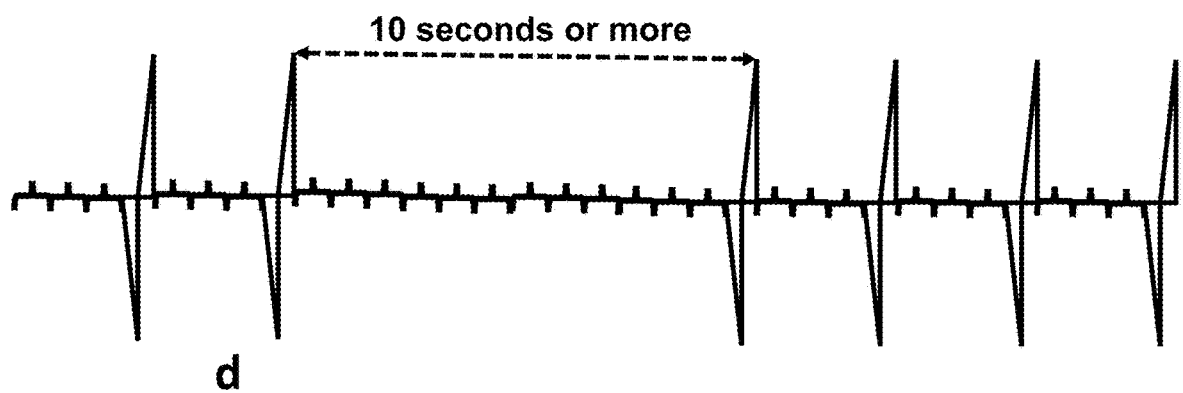
d
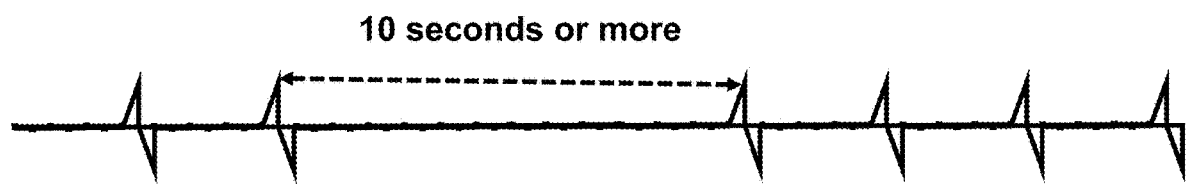
e  Figure 11B

SLEEP APNEA DETECTION AND MITIGATION DEVICE

The application claims priority to the following related applications and included here are as a reference.

Application: U.S. patent application Ser. No. 18/635,236 filed Apr. 15, 2024.
Application: U.S. patent application Ser. No. 18/436,349 filed Feb. 8, 2024.
Application: U.S. patent application Ser. No. 17/986,005 filed Nov. 14, 2022.
Application: U.S. patent application Ser. No. 17/891,205 filed Aug. 19, 2022.
Application: U.S. patent application No. 63/272,659 filed Oct. 27, 2021.

BACKGROUND

Controlling air pollution in the environment has become increasingly important owing to the health risks of exposure to high concentrations of harmful air pollutants. PM2.5 or particles that make the air polluted and have diameter less than 2.5 micrometres (more than 100 times thinner than a human hair) remain suspended in the air for longer time. These particles are formed because of burning fuel, chemical reactions that take place in the air, and other sources of aerosol droplets. To protect people against the harmful effects of air pollution, filtering of these pollutants is significant. Thus, understanding the filtration performance of solutions is essential for assessing the air quality.

Masks have been on the market for many years and are especially suitable in the "urban environment", i.e., when walking, biking, and commuting in the city and having to get through heavy traffic where cars are the source of pollution (especially those diesel cars). The masks have always been mentioned as an effective tool against environmental threats. They are considered as protective equipment to preserve the respiratory system against the non-desirable air droplets and aerosols such as viral or pollution particles.

The aerosols can be pollution existence in the air, or the infectious airborne viruses initiated from the sneezing, coughing of the infected people. The filtration efficiency of the different masks against these aerosols are not the same, as the particles have different sizes, shapes, and properties. Therefore, the challenge is to fabricate the filtration masks with higher efficiency to decrease the penetration percentage in the nastiest conditions. To achieve this concept, knowledge about the mechanisms of the penetration of the aerosols through the masks at different effective environmental conditions is necessary.

Breathing clean air is something that most of us take for granted, until it's taken away from us. It is essential to maintaining good health. We would be surprised to know, over 99% of the world's population breathes unsafe air. Air pollution, according to the World Health Organization (WHO), has resulted in nearly 7 million deaths annually, with low- and middle-income countries suffering from the highest exposures. Air pollution is one of the leading causes of death around the world, one in nine to be specific. It's a global health crisis, and it is imperative that we focus on protecting and preserving our respiratory health.

There is a need for a Smart Protective Mask that offers its user clean air to breathe. Wherein air is first actively pulled in from the environment, filtered and then inhaled. Next, contaminated, exhaled air is also filtered and expelled from the device back out into the surrounding environment.

A unique design that sets it apart from simple surgical masks or cumbersome respirators, lightweight and portable, much smaller than other options on the market today with a wearable device that attaches nicely to the body and is adjustable for comfort.

A solution that is unobtrusive and easy to use, it does not interfere with daily tasks or work, whereas many respirators require attachment around the waist and can get in the way. It also offers multiple functions—air filtration, oxygen supply, air conditioning.

What needs to set the smart protective mask apart from other respiratory devices is that Unlike other masks, air is actively pulled in and pushed out of the device. An individual does not have to rely on their breath or pressure from inhalation and exhalation to do the work of creating air flow. The mask does the work for them. It essentially creates a clean breathing environment in the mask. So, it's easy to use, making it more likely to be used. And it comprehensively addresses the issue of exposure to poor air quality, whether it's outdoor or indoor air pollution or even hazardous work environments.

The atmosphere is composed mostly of gases. While air is mostly gas, it also holds tiny particles. Particulate matter (PM) is everything in the air that is not a gas. Particles with a diameter of 10 micrometers or less can enter deep inside a person's lungs. Fine particles with a diameter of 2.5 micrometers or less can penetrate the lung barrier and enter a person's blood system. They are the most health-damaging. Both short and long-term exposure to air pollutants increases the risk of developing a range of health issues. The most severe impacts are felt by those who are already ill, children, the elderly, and those most affected by poverty. However, all the following are impacted:

Densely Populated Cities & Urban Areas: where people are regularly exposed to particulate pollution.
Developing Countries: with limited environmental regulations and heavy industrialization.
Industrial Zones: which, without proper management and mitigation strategies, have toxic or contaminated air.
Healthcare Industries: where staff and patients are exposed to airborne transmissions or contamination.
Hazardous Work Environments: where employees are exposed to toxic fumes and gases or who work in confined or poorly ventilated spaces.
Public Safety Workers: whose air quality can be compromised by hazardous substances.
High-Elevation Sports: where decreased air pressure and lower oxygen concentrations can severely affect health.

The solution needs to protect and preserve respiratory health in the event of poor air quality and low oxygen concentration in all these instances.

Another application of a mask with air flow provided in its interior is to detect and mitigate sleep apnea. Sleep apnea is a common condition in which our breathing stops and restarts many times while we sleep. This can prevent our body from getting enough oxygen. We may want to talk to our healthcare provider about sleep apnea if someone tells us that we snore or gasp during sleep, or if we experience other symptoms of poor-quality sleep, such as excessive daytime sleepiness.

There are Two Types of Sleep Apnea:

Obstructive sleep apnea happens when our upper airway becomes blocked many times while we sleep, reducing or completely stopping airflow. This is the most common type of sleep apnea. Anything that could narrow our airway such as obesity, large tonsils, or changes in our hormone levels can increase our risk for obstructive sleep apnea.

Health problems due to poor sleep and sleep disorders are very common in urban as well as rural populations in recent times. Among the different sleep disorders, sleep apnea syndrome (SAS) or obstructive sleep apnea (OSA) is one of the common varieties, characterized by the recurrent cessation of breathing during sleep. However, such problems emanating from sleep disorders often remain undiagnosed and untreated in their earlier stages. One of the reasons for this could be the lack of easy diagnostic procedures to detect sleep disorders like OSA.

Polysomnography (PSG) is the gold standard method for sleep apnea diagnosis. PSG consists of an overnight recording of different physiological signals such as electroencephalogram (EEG), electrooculogram (EOG), electromyogram (EMG), electrocardiogram (ECG), airflow, oxygen saturation in arterial blood, respiratory efforts, snoring, and body, etc. PSG is an expensive, time consuming, and labor-intensive procedure. Hence, there exists a need for developing reliable diagnostic alternatives in sleep studies using fewer biological signals that can provide effective diagnosis and treatment of patients with sleep related complaints.

Central sleep apnea happens when our brain does not send the signals needed to breathe. Health conditions that affect how our brain controls our airway and chest muscles can cause central sleep apnea. This condition is different from obstructive sleep apnea, in which breathing stops because the throat muscles relax and block the airway. Central sleep apnea is less common than obstructive sleep apnea.

Central sleep apnea can result from other conditions, such as heart failure and stroke. Another possible cause is sleeping at a high altitude. Treatments for central sleep apnea might involve managing existing conditions, using a device to assist breathing, or using supplemental oxygen.

In another application the wearable device comprises an oxygen tank with a pressure regulator. A pressure regulator is a valve that controls the pressure of a fluid to a desired value, using negative feedback from the controlled pressure. Regulators are used for gases and liquids and can be an integral device with a pressure setting, a restrictor and a sensor all in the one body, or consist of a separate pressure sensor, controller and flow valve.

Two types are found: The pressure reduction regulator and the back-pressure regulator. Both types of regulator use feedback of the regulated pressure as input to the control mechanism, and are commonly actuated by a spring loaded diaphragm or piston reacting to changes in the feedback pressure to control the valve opening, and in both cases the valve should be opened only enough to maintain the set regulated pressure.

This application discloses a novel sleep apnea detection and mitigation device. The device uses a face mask connected to a pillow with an embedded device. The embedded device has an air inlet assembly to pull in air from the environment, an exhaust assembly to release air to the environment, a control circuit, and an oxygen tank with a regulator. The inlet assembly releases filtered air into the face mask through an air tube and the exhaust assembly pulls contaminated air from the interior of the face mask through another air tube. Airflow sensors within the path of the airflow are used to measure the real time airflow data. The control circuit uses the measured real time airflow data to detect sleep apnea. The control circuit also reshapes or vibrates the pillow to mitigate the apnea.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a respirator that is used for protection against aerosols in the environment uses a wearable device that is a neck hanger, a head ring, a helmet, a backpack, a chest pack or bag, a waist or body attachment.

In another aspect, the wearable device is connected to a face mask via two flexible air pipes (tubes).

In another aspect, the wearable device is a tube with circular, rectangular, or any proprietary cross sections.

In one aspect, the wearable device uses two fans, one for an inlet assembly to pull in the air from the environment and one for an exhaust assembly to receive the interior air of a face mask used by the respirator.

In another aspect, the wearable device uses two filters, one to filter the air in the inlet assembly and one to filter the contaminated air in the exhaust assembly.

In another aspect, the filtered air in the exhaust assembly through some opening holes on the peripheral of the wearable device is blown towards head and face of the person wearing the respirator for cooling.

In one aspect, the area of opening holes across the peripheral of the wearable device are different to provide a uniform air flow towards the face, neck, and head.

In another aspect, there is an oxygen tank inside the wearable device.

In another aspect, the wearable device has valve to refill the oxygen tank.

In one aspect, the wearable device has a regulator that controls the pressure of oxygen within the regulator and the amount of oxygen flow to the face mask.

In another aspect, the regulator is a container with an inlet oxygen valve and an outlet oxygen valve.

In one aspect, the regulator uses a sensor to measure the oxygen pressure within the container and an airbag to increase or decrease the oxygen pressure and amount of oxygen exiting the outlet oxygen valve by inflating or deflating the airbag.

In another aspect, the airbag is inflated automatically through an air pipe connected to a valve in wearable device's exhaust assembly, or an air pump attached externally to the wearable device and connected to an airbag inlet/outlet valve.

In another aspect, the airbag is inflated and deflated by the inlet/outlet valve on the peripheral surface of the wearable device.

In one aspect, the oxygen pressure inside the regulator container and the amount of oxygen that exits the regulator are controlled by expandable pads (polymer pads or other material).

In one aspect, an electroactive polymer (EAP) is a polymer that exhibits a change in size or shape when stimulated by an electric field.

In another aspect, the pads are expanded and contracted by a voltage applied across them under control of a control circuit.

In one aspect, an artificial intelligence (AI) algorithm executed in a central processing unit (CPU) of the control circuit uses information data from regulator sensor, other sensors, and external devices or networks to determine when the airbag needs to be inflated or deflated.

In another aspect, the filtered air from the environment is mixed with oxygen before being released into the face mask through an air pipe (tube).

In one aspect, the wearable device has a housing for the control circuit and a power supply.

In another aspect, the control circuit controls the speed of the fans and various sensors used by the wearable device, the face mask and the air pipe (tube) connecting the face mast to the wearable device.

In one aspect, sensors are located at various locations of the wearable device and the face mask to control various functions and measure various data.

In another aspect, sensors are not on all the time. They are switched on and off as needed to save power. The switching on/off can be configured in the control circuit and the control circuit based on the configuration parameters turns the sensors on, collect information data for processing and then turns the sensors off to save power.

In one aspect, the power supply uses a rechargeable battery.

In another aspect, the rechargeable battery is charged by solar power using micro-panels (small panels) attached to external surface of the face mask and external surface of the wearable device.

In one aspect, the power supply has a DC (Direct Current) converter circuit to convert solar energy to the DC voltage required for charging the battery.

In one aspect, the rechargeable battery is charged through a USB (universal serial bus) or other power ports.

In one aspect, the battery is charged wirelessly.

In another aspect, a charger with a USB or other power cords is used to connect to the wearable device for charging the battery.

In one aspect, the control circuit and battery can be removed and replaced.

In another aspect, the wearable device has a physical activation key or nob attached to the exterior surface of the wearable device.

In one aspect, the wearable device has a reset bottom or can be reset through USB port or a wireless transceiver.

In one aspect, the USB port is used to communicate with an external device for configuration, software download, monitoring, alarm, and diagnostic.

In another aspect, the control circuit has a transceiver to communicate wirelessly with an external device for configuration, software download, monitoring, alarm, and diagnostics.

In one aspect, the transceiver used by the control circuit is Bluetooth, Zigbee, infrared, or WiFi (wireless fidelity).

In another aspect, the transceiver supports fifth generation (5G), sixth generation (6G), or beyond 5G/6G protocols and allows respirator (face mask with wearable device) to act as an Internet of Things (IoT) device to communicate with 5G, 6G, beyond 5G/6G or WiFi IoT network.

In one aspect, the control circuit controls all functions of the respirator (face mask with the wearable device).

In another aspect, the environment air is passed through a filter before being pulled in by a fan in the air inlet assembly.

In one aspect, both air pipes (tubes) that are connected to the wearable device and the face mask also perform filtering of the air pulled in from environment and the contaminated air released from interior of the face mask.

In another aspect, the wearable device is a pillow that is placed around the neck of a person (wearer) like a neck pillow used by people traveling by airplane.

In one aspect, the pillow can have any shape if it does not interfere with the user's normal sleep like with a normal pillow.

In another aspect, the pillow in addition to all the functions, components and capabilities of the wearable device can be reshaped and change size and shape to adjust a position of the head of the person to mitigate snoring and sleep apnea.

In one aspect, the reforming, change of shape and size of the pillow are performed under control of an artificial intelligence (AI) algorithm executed in a central processing unit of the control circuit.

In another aspect, the control circuit AI algorithm uses the real time measured data from all or subset of the sensors internally or externally attached to the pillow, air tubes, and face mask as well as all biometric devices that are attached to the body of the person using the sleep apnea detection and mitigation device to decide when and how to reshape or change the shape and size of the pillow.

In one aspect, control circuit uses expandable polymer pads and airbags to reshape or change the shape and size of the pillow.

In another aspect, the control circuit reshapes or changes the shape and size of the pillow by applying voltage across the expandable polymer pads or inflating and deflating of the airbags.

BRIEF DESCRIPTION OF THE DRAWINGS

FIG. 2 illustrates a wearable device that is a neck hanger and supplies air to the face mask.

FIG. 3A illustrates a neck hanger (wearable device) that blows air towards the neck and head for cooling.

FIG. 3B illustrates a neck hanger (wearable device) with a single housing for battery and control circuit.

FIG. 4B depicts a neck hanger with a regulator.

FIG. 4L illustrates the structure of a regulator using an airbag and inflating cartridges.

FIG. 6G shows the direction of air flow when the wearable device is used to cool the neck and head.

FIG. 10 illustrates the possible positions of airflow sensors.

FIG. 11B depicts airflow when apnea occurs.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications, and equivalents, which may be included within the spirit and scope of the various embodiments as defined by the appended claims.

Furthermore, in the following description of embodiments, numerous specific details are set forth to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
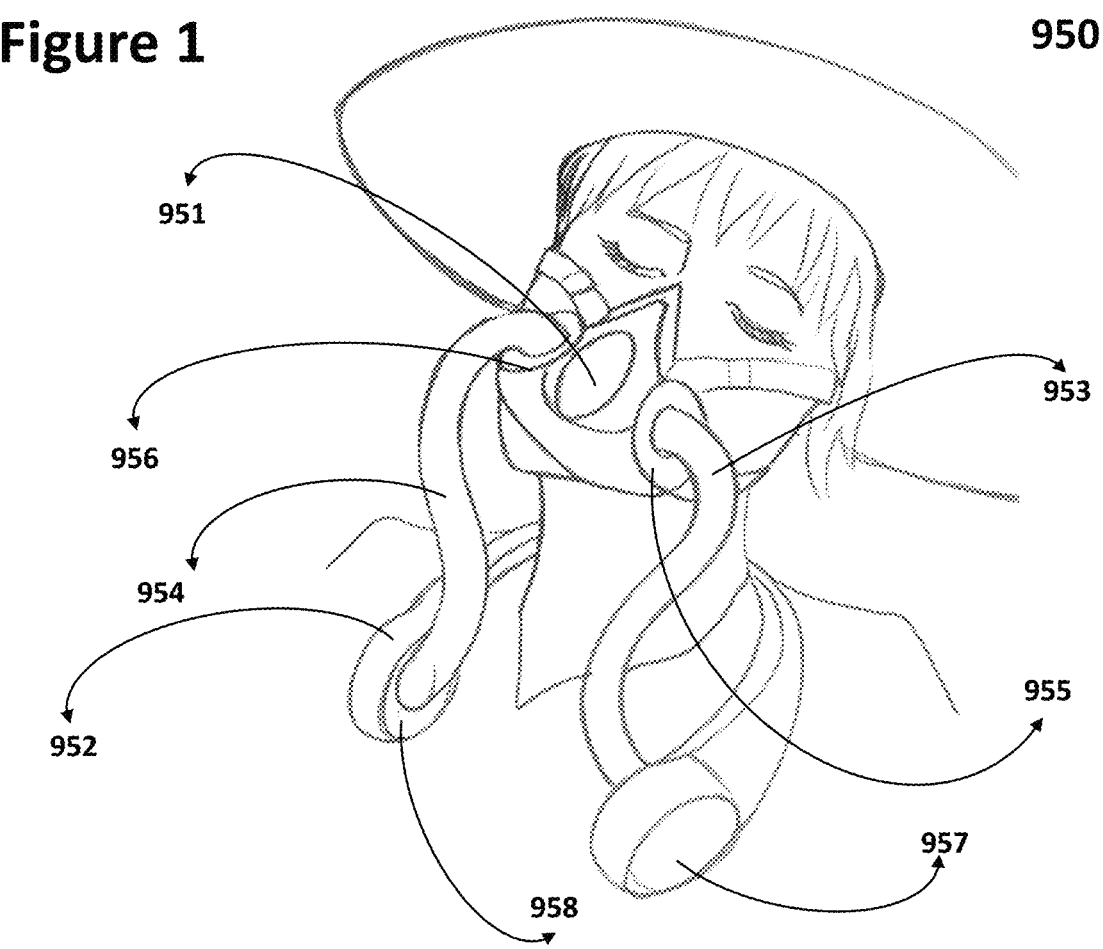
FIG. 1 illustrates a respirator using a face mask and a neck hanger (wearable device).

FIG. 1 depicts a novel respirator 950 using a face mask 951 and a wearable device (that is a neck hanger) 952. The respirator 950 comprises a typical face mask 951, an air pipe (tube) 953 that receives air from inlet assembly 957, an air pipe (tube) 954 that receives contaminated air from interior of the face mask 951 and delivers it to exhaust assembly 958. Air pipes (tubes) 953 and 954 are attached to the face mask 951 through connectors 955 and 956. Fresh air is pulled in from free space and filtered by inlet assembly 957 and delivered to face mask 951 using an air pipe 953 that is connected to both wearable device (neck hanger) 952 and face mask 951. Contaminated air from interior of the face mask 951 is received by air pipe 954 that is connected to both face mask 951 and wearable device (neck hanger) 952 and delivered to wearable device exhaust assembly 958 to be released into free space (environment). The air pipes 953 and 954 may be part of wearable device (neck hanger) 952 or face mask 951.

In one embodiment, the wearable device (neck hanger) 952 is also used as a neck cooler by blowing some of the air it pulls in by inlet assembly 957 from free space towards the neck.

In one embodiment, the wearable device (neck hanger) 952 is used as a neck cooler by blowing the filtered contaminated air received from interior of the face mask 951 by exhaust assembly 958 towards the neck.

In one embodiment, the wearable device (neck hanger) 952 is used as a neck cooler by blowing some of the filtered environment air pulled in by inlet assembly 957 and the filtered contaminated air received from the interior of the face mask 951 by exhaust assembly 957 towards the neck using air apertures or opening holes.

In another embodiment, the air flow of aperture or opening hole is controlled by changing the opening of the aperture or hole.

In another embodiment, the wearable device (neck hanger) 952 pulls in (sucks) the air from free space using inlet assembly 957 and sends it to the face mask 951 without filtering.

In one embodiment, the wearable device (neck hanger) 952 pulls in (sucks) the air from free space using inlet assembly 957 and sends it to the face mask 951 after being filtered.

In another embodiment, the wearable device (neck hanger) 952 pulls in (sucks) the air from free space using inlet assembly 957 and sends some of it after being filtered into the interior of the face mask 951 and blows the remaining of the sucked air filtered or unfiltered towards the neck for cooling.

In one embodiment, the air pipes 953 and 954 are part of the wearable device (neck hanger) 952 and can be slid inside the wearable device (neck hanger) 952 when not connected to the face mask 951.

In one embodiment, the air pipes 953 and 954 are independent components and are connected to both face mask 951 and wearable device (neck hanger) 952 through various simple (connectors) methods that prevent any air leak.

In another embodiment, the amount of air passed through interior of the face mask 951 is controlled by various known practical methods such as inlet assembly 957, the amount of air that is used for cooling, releasing extra air, etc.

In another embodiment, the amount of air used by wearable device (neck hanger) 952 for cooling neck (back of the head) is controlled by various known practical methods such as opening and closing the apertures or holes that blows the air, reducing the opening of the apertures or holes, etc.

In one embodiment, the amount of sucked (pulled in) air from free space (environment) by the wearable device (neck hanger) 957 and contaminated air from interior of face mask 951 by exhaust assembly 958 is controlled and adjusted through various known practical methods such changing the DC voltage applied to the inlet or exhaust assembly fans.

In one embodiment, wearable device (neck hanger) 952 stores oxygen and through an injection valve mixes a controlled amount of oxygen with filtered or unfiltered air sucked (pulled in) from free space by inlet assembly 957 before sending the mixed air through air pipe 953 into the interior of the face mask 951.

In another embodiment, the amount of oxygen that mixes with sucked and filtered or unfiltered air from free space is controlled for different applications.

In one embodiment, the novel respirator 950 is used for various applications when the body needs air with required oxygen level. These applications are people with asthma, high elevation hikers, hospital patients, nurses, doctors, miners, gliders, people with breathing problem, people with heart problem, people with medical problems that need higher level of oxygen, skiers at high elevations, ordinary people in areas with high level of air pollution (cities), fire fighters, tourist in high elevation places, factory workers, carpenters, chemical lab workers, airplane passengers, and any other application that requires a face mask.

FIG. 2 depicts a wearable device 1000. The wearable device (neck hanger) 1000 has an inlet assembly 957 that uses a fan 1002 to suck (pull in) the air from environment, filter it with filter 1006 and send it from outlet 1008 into the interior of the face mask 951 through air pipe 953. The contaminated air from interior of face mask 951 is sent through air pipe 954 to inlet 1009 of wearable device 1000, then exhaust assembly 958 filters the contaminated air by filter 1007 before released into the environment by fan 1003.

The wearable device 1000, among other things includes a flexible tube 1001, sucking fans 1002 and 1003, filters 1006 and 1007, battery housings 1004 and 1005, outlet 1008 and inlet 1009.

The flexible tube 1001 can be solid or hollow depending on the application of wearable device 1000. The flexible tube 1001 is made of very light materials to keep the overall weight of the wearable device 1000 low. The battery housings 1004 and 1005 (it is possible to use only one housing with one battery to power both fans) accommodate the batteries that power the fans 1002 and 1003. The outlet 1008 and inlet 1009 have circular (square, or other) cross sections and provide necessary requirements to connect to air pipes 953 and 954 without any leakage of air.

The fans 1002 and 1003 both pull in (suck) air from environment and the interior of the face mask 951 respectively and their sucking power is adjusted independently by controlling the DC voltage applied to them from the batteries housed in1004 and 1005 (the control is done by a control circuit that resides in one of the battery housings or a single housing that provides power to both fans) assigned to them. The filters 1006 and 1007 both are either high efficiency particulate air (HEPA) filter, ultra-low particulate air (ULPA) filters, or a proprietary filter based on the application of the neck hanger 1000.

There are several options for filtering the environment air and interior air of the face mask. The filtering function by filter 1006 can be performed first, then the filtered air is sucked (pulled in) by sucking fan 1002. Another option is to suck (pull in) the environment air by sucking fan 1002 first and then filter it by filter 1006. A third option is to perform the function of filtering inside air pipe 953. In other words, air pipe 953 which connects the wearable device (neck hanger) 952 (through connector 1008) and face mask 951 functions both as a tunnel for the flow of air from neck hanger 952 to the interior of face mask 951 and a filter (HEPA, ULPA, or proprietary). A fourth option is to have filter at two of the above-mentioned locations (before sucking fan, after sucking fan, and air pipe). A fifth option is to have the filter at all three locations explained above (before sucking fan, after sucking fan, and air pipe). The above options also apply to air pipe 954, sucking fan 1003 and filter 1007.

Filter can perform one or more functions. It can filter various types of aerosols that are harmful for breathing, droplets, particles in the air, or unpleasant smells. It is possible to add filters in various locations mentioned above to take care of aerosols, droplets, particles, and unpleasant smells. This applies to all wearable devices (neck hangers, head ring, helmet, backpack, chest pack or bag and body attachments) that will be explained in later paragraphs.

Tubes 1001, 1201, and1901 can have any shape and cross sections and it all depends on the application and type of wearable device (neck hangers, head ring, helmet, backpack, chest pack or bag, and body attachments). In this application only a neck hanger and head ring explained in detail. Other solutions like helmet, backpack, chest pack or bag, and other body attachments have the same components and parts with different shape, size, and material. Therefore, what is disclosed in this application applies to all types of wearable devices that can be used for the respirator of 950,1900, and other types of respirators.

FIG. 3A shows a wearable device (neck hanger) 1100. Neck hanger 1100 in addition to facilitating flow of fresh and filtered air into the interior of the face mask 951 performs cooling of the neck (head and face) by blowing air towards the neck and head. The air sucked (pulled in) by fan 1102 is filtered by filter 1106 in inlet assembly 957 first, then a portion of the filtered air is sent into the interior of the face mask 951 from outlet 1108 through air pipe 953 and the remaining of the filtered air through apertures or holes 1110 is blown towards the neck and the head. The speed of the air flow from the apertures 1110 can be adjusted by reducing the opening area of the apertures or by totally closing a selected number of apertures 1110.

Contaminated air from the interior of face mask 951 is sucked (pulled in) by exhaust assembly 958 using fan 1103 from inlet 1109 through air pipe 954, filtered by filter 1107, then sent to the apertures 1110 for blowing towards the neck and the head. Fan 1103 in addition to the contaminated air it sucks from the interior of the mask through air pipe 954 and inlet 1109 may also sucks (pulls in) air from environment through a separate inlet on the neck hanger tube 1101 to increase the amount of the air that is blown towards neck and head through apertures 1110.

The wearable device (neck hanger) 1100, among other things includes a flexible tube 1101, sucking fans 1102 and 1103, filters 1106 and 1107, battery and control circuit housings 1104 and 1105 (it is possible to use one housing with one battery and control circuit for both fans and other functions), outlet 1108, aperture 1110, inlet 1109 and possible additional inlet for sucking the environment air by fan 1103.

Flexible tube 1101 can be solid or hollow depending on the application of wearable device (neck hanger) 1100. The flexible tube 1101 is made of very light materials to keep the overall weight of the neck hanger 1100 low. Tube 1101 has either a U-shape, a horseshoe shape, or any proprietary shape and cross section. The battery housings 1104 and 1105 accommodate the batteries (and a control circuit) that power the fans 1102 and 1103. The outlet 1108 and inlet 1109 have circular (square, or other) cross sections and provide necessary requirements to connect to air pipes 953 and 954 without any leakage of air. Additional inlet also can be provided on flexible pipe 1101 to be used by fan 1103 to suck extra air from the environment. Tube 1101 can have a key on its external surface for turning on and off the operation of the wearable device (neck hanger) 1100. The wearable device (neck hanger) 1100 can also have a reset botton on the external surface of tube 1101 to reset the control circuit.

The flexible tube 1101 is hollow and made of very light materials (like plastic, fiber glass, aluminum, etc.) to keep the overall weight of the wearable device (neck hanger) 1100 low. The battery housings 1104 and 1105 accommodate the batteries (and a control circuit) that power the fans 1102 and 1103. The DC voltage from batteries applied to fans is independently adjusted by control circuit housed in wearable device (neck hanger) 1100.

FIG. 3B shows the wearable device (neck hanger) 1100 when only one housing 1104 is used for the battery that powers the fans, LED, sensors, control circuit electronics, and any moving components that requires power.

Figure 4A:
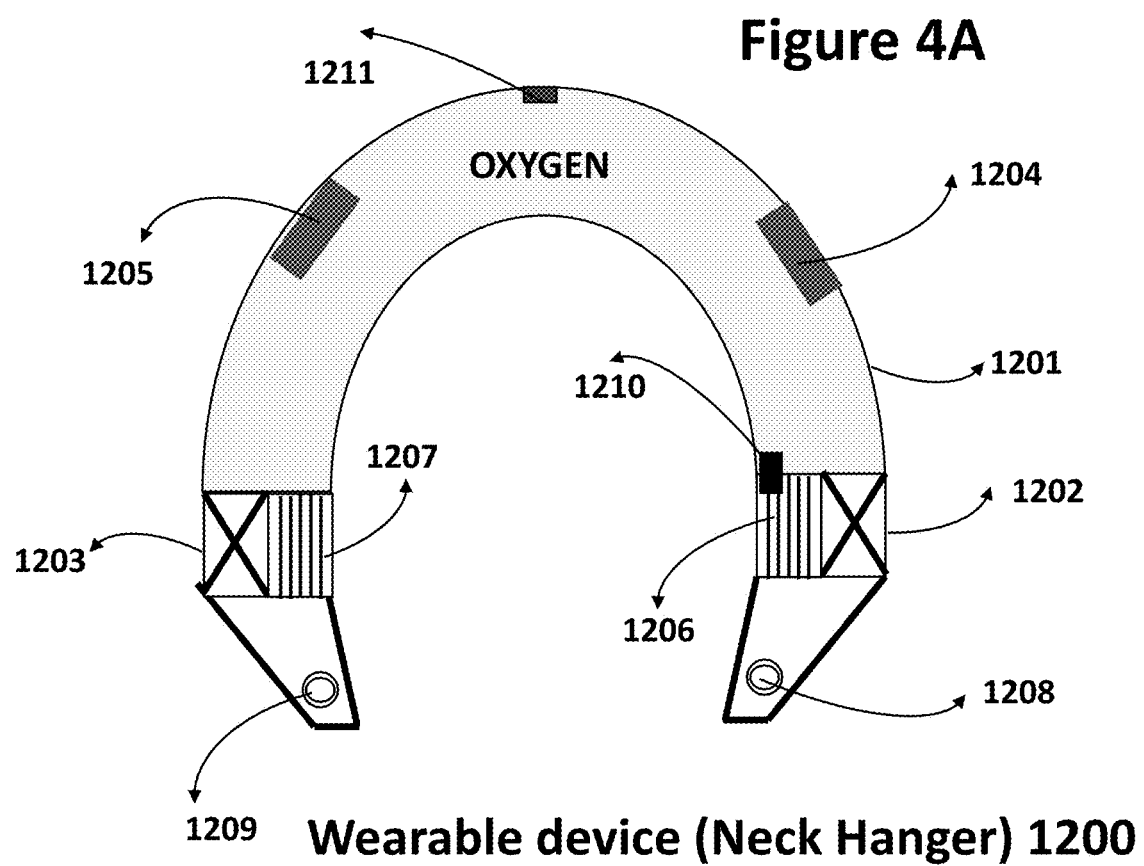
FIG. 4A illustrates a neck hanger (wearable device) that supplies air and oxygen into the face mask.

The housing in addition to the battery also houses the control circuit electronics. The housing has an USB port or other ports for charging the batteries and communication of the control circuit with external device, FIG. 4A illustrates wearable device (neck hanger) 1200. Wearable device (neck hanger) 1200, in addition to the functions that wearable device (neck hanger) 1000 performs is also an oxygen tank for storing oxygen. Wearable device (neck hanger) 1200 facilitates flow of fresh and filtered air that is mixed with oxygen from an oxygen tank inside the face mask 951. The air sucked (pulled in) by fan 1202 is filtered by filter 1206 and mixed with injected oxygen from valve 1210 before flowing into the interior of face mask 951 from outlet 1208 and through air pipe 953. Contaminated air from the interior of face mask 951 is sucked (pulled in) by fan 1203 through air pipe 954 and inlet 1209 then filtered by filter 1207 and released to the environment.

Wearable device (neck hanger) 1200, among other things includes a flexible or solid oxygen tank 1201, sucking fans 1202 and 1203, filters 1206 and 1207, battery/control circuit housings 1204 and 1205, outlet 1208, inlet 1209, oxygen valve 1210 and oxygen refill port 1211.

The solid (flexible) circular (square or other shapes) oxygen tank 1201 houses pure oxygen for mixing with filtered fresh air from the environment. The flexible or solid circular (square or others) oxygen tank 1201 is made of very light materials to keep the overall weight of the wearable device (neck hanger) 1200 low. The battery housings 1204 and 1205 accommodates the batteries that power the fans 1202 and 1203. The outlet 1208 and inlet 1209 have circular (square or others) cross sections and provide necessary requirements to connect to air pipes 953 and 954 without any leakage of air. The sucked (pulled in) air from environment by fan 1202 is first filtered by HEPA, ULPA, or any proprietary filter 1206 then mixed with the oxygen from oxygen tank released by valve 1210 before flowing into the interior of the face mask 951 through outlet 2108 and air pipe 953. The oxygen tank is refilled through refill port 1211.

The valve 1210 is controlled to inject oxygen continuously or as needed. When oxygen is injected continuously it can be controlled to inject the amount of oxygen that is needed and the person wearing face mask 951 feels comfortable. The oxygen can also be injected as needed. This is done in two ways. The first way is to have a controller that injects the oxygen in a controlled interval by opening the injection valve 1210 for a controlled time window and then closing the injection valve 1210. The interval between two injection time windows is also controlled. Therefore, the injection valve1210 opens for a time window and closes for an interval of time and again opens for the time window. Both the open time window and closed time interval between two openings of injection valve 1210 is controlled by a controller within the control circuit using an artificial intelligence (AI) algorithm executed in a CPU. This way the oxygen tank lasts longer.

The second method is opening the injection valve 1210 manually as needed. The person wearing respirator 950 decides when there is a need for extra oxygen and opens the injection valve1210 for a defined time window. The time window can be different each time injection valve 1210 is opened manually. The injection valve 1210 can continuously be left open during the time respirator 950 is being used.

FIG. 4B depicts a wearable device (neck hanger) 1200 with a regulator. The regulator consists of pressure reducer 1212 and a flow adjuster 1213. These two components 1212 and 1213 are adjusted mechanically or automatically. The oxygen tank can be a tank within tube 1201. The entire tube 1201 or a portion of it can also be used as oxygen tank. It all depends on several parameters which are safety issues, weight, pressure of compressed oxygen (in any form, gas, solid or liquid), and complexity. The regulator should also function as a pressure gauge and a flow meter. One way of providing these two functions is to use sensors, one as pressure sensor and another as flow sensor. The other approach is to have provisions for a pressure gauge or flow meter to be connected to the regulator when needed like a valve that is used to refill the oxygen tank.

There are three basic operating components in most regulators: a loading mechanism, a sensing element, and a control element. These three components work together to accomplish pressure reduction. The Loading Mechanism determines the setting of the regulator delivery pressure. Most regulators use a spring as the loading mechanism. When the regulator hand knob is turned, the spring is compressed. The force that is placed on the spring is communicated to the sensing element and the control element to achieve the outlet pressure.

The Sensing Element senses the force placed on the spring to set the delivery pressure. Most regulators use a diaphragm as the sensing element. The diaphragm may be constructed of elastomers or metal. The sensing element communicates this change in force to the control element.

The Control Element is a valve that accomplishes the reduction of inlet pressure to outlet pressure. When the regulator hand knob is turned, the spring (loading mechanism) is compressed. The spring displaces the diaphragm (sensing element). The diaphragm then pushes on the control element, causing it to move away from the regulator seat. The orifice becomes larger to provide the flow and pressure required. FIGS. 4C through 4N disclose three different methods or ways of implementing a regulator for wearable devices.

Figure 4C:
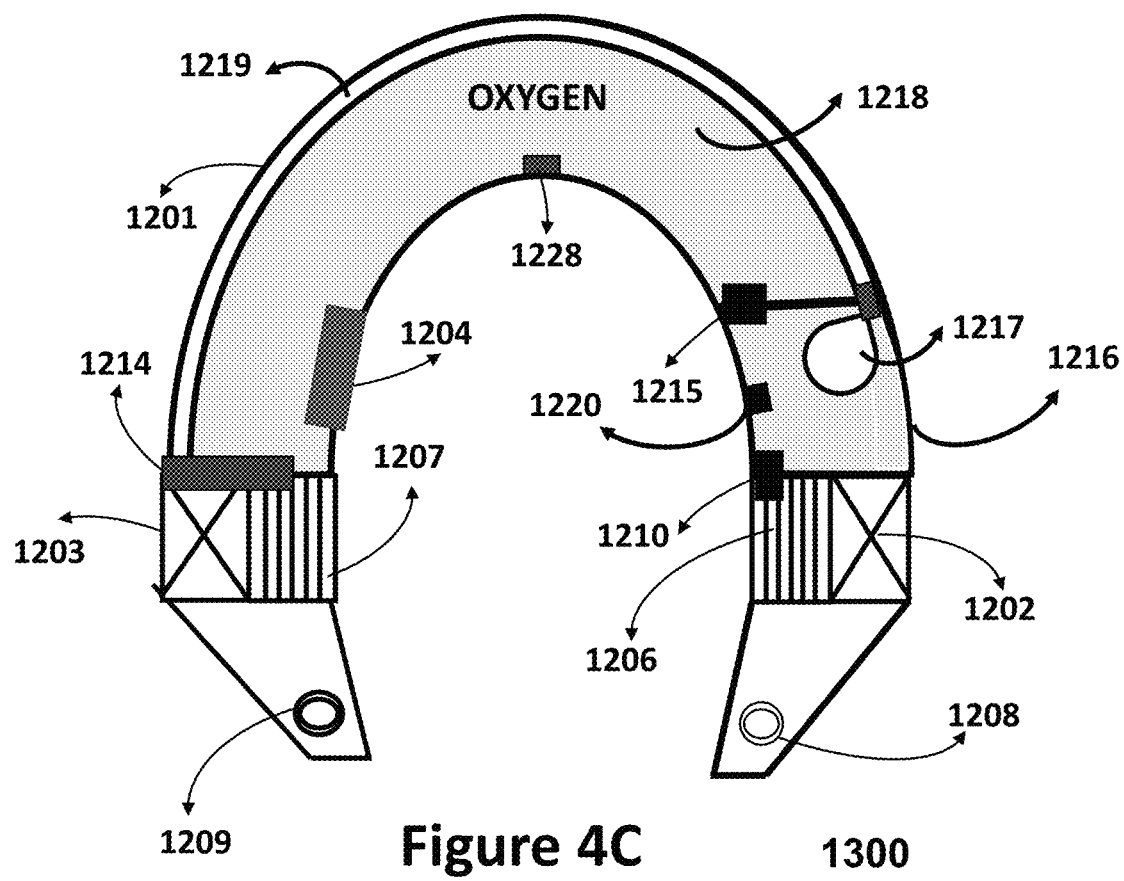
FIG. 4C shows a wearable device with a regulator using an airbag that is internally inflated and deflated.

FIG. 4C depicts a wearable device (neck hanger) 1300 with a regulator. The regulator comprises of an oxygen container 1216 that holds the released oxygen from oxygen tank 1218, an airbag 1217 acting as loading mechanism, a sensor 1220 that senses the oxygen pressure and reports to the control circuit, an inlet valve 1215, and an outlet valve 1210. The regulator is attached to the oxygen tank 1218 and through inlet 1215 receives oxygen.

It is also attached to the air inlet assembly 957 (fan 1202 and filter 1206) for delivering oxygen through outlet valve 1210 to be mixed with the filtered inlet air from the environment. The airbag 1217 is inflated and deflated through air duct 1219 and valve 1214 which is attached to the exhaust assembly (fan 1203 and filter 1207). The inflation and deflation of the airbag 1217 is controlled by pressure sensor 1220 and control circuit 1204. By inflating and deflating the airbag the amount and pressure of the oxygen exiting outlet 1210 is controlled. The regulator can be stand alone or an integral part of oxygen tank 1218 of wearable device (neck hanger) 1300.

Figure 4D:
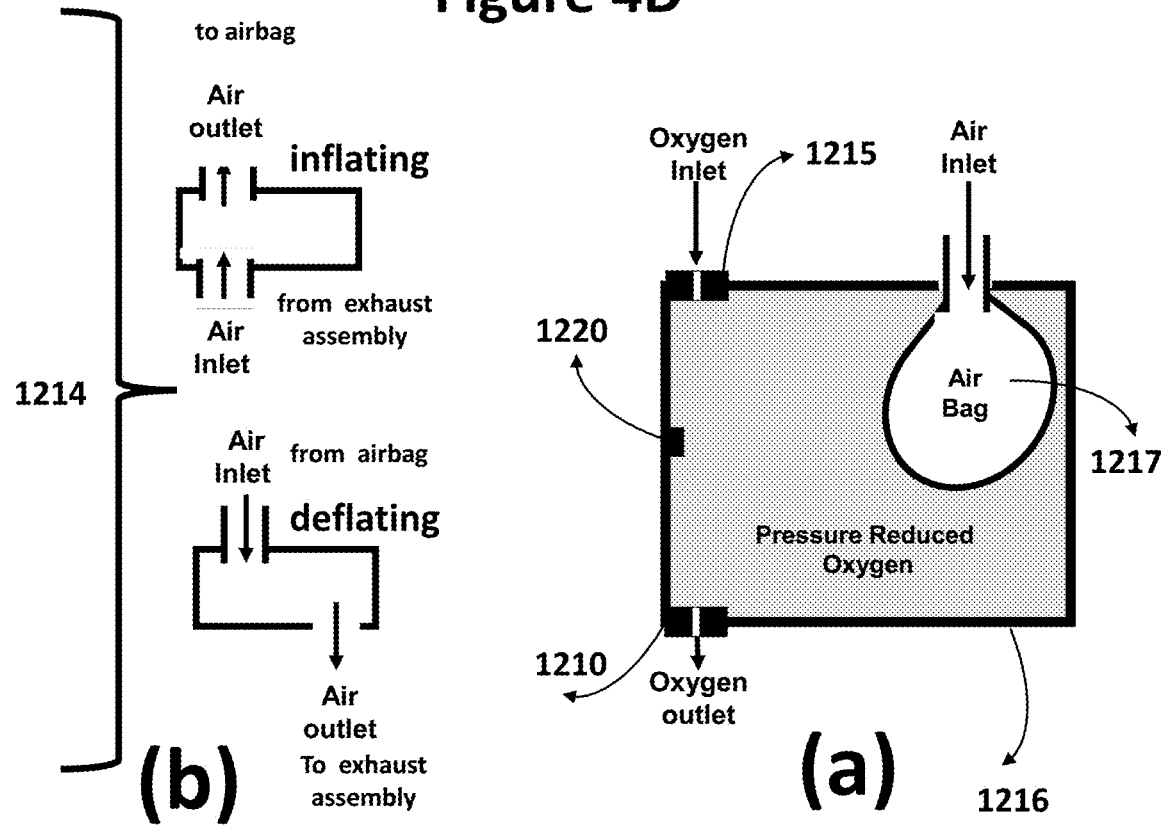
FIG. 4D illustrates the structure of a regulator using airbag with method of inflating and deflating the airbag.

FIG. 4D shows an implementation of the regulator used in wearable device (neck hanger) 1300. The drawing "a" on the right of FIG. 4D illustrates container 1216 that holds the oxygen that its pressure is controlled by airbag 1217. Valve 1215 injects oxygen from oxygen tank 1218 into container 1216. By inflating and deflating airbag 1217 the volume of the container 1216 is decreased or increased which results in increasing and decreasing of the oxygen pressure inside the container 1216 and the pressure and amount of the oxygen which is released from valve 1210 and mixed in the inlet assembly 957 with the air that is sucked (pulled in) from the environment by fan 1202 and filtered by filter 1206 before being released into the interior of the face mask 951. The control of inflating and deflating airbag 1217 is done by sensor 1220 and control circuit 1204 (control circuit resides in power housing 1204). The sensor 1220 real time measures the oxygen pressure within container 1216 and sends the data to control circuit 1204 to be used. The control circuit 1204 also uses the information data it receives from other sensors of respirator 950, from IoT network, from IoT device (smart phones. tablet, laptop, and any smart wireless device), and from IoT biometric devices that are attached to the body of the person using the respirator. An artificial intelligence (AI) algorithm executed in the CPU of control circuit 1204 analyzes all the information data to determine when to inflate or deflate the airbag.

Inflating and deflating of the airbag is done internal to wearable device (neck hanger) 1300. The airbag through air pipe (tube) 1219 is connected to valve 1214. The drawing "b" on the left side of FIG. 4D shows the structure of valve 1214. The valve 1214 has three apertures. One of them that is connected to the air pipe (tube) 1219 is used as both inlet (during inflating) and outlet (during deflating). The other two apertures are connected to exhaust assembly 958 (fan 1203, and filter 1207) either side of the exhaust fan 1203. One of these two apertures is used as inlet during inflating while the other aperture is closed. The other aperture is used as an outlet during deflating while the inlet one is closed. The design of valve 1214 is not the subject of this application.

As was explained above the opening and closing of the apertures of valve 1214 are controlled by the control circuit and its AI algorithm. AI algorithm uses the configuration data, real time information data collected by various sensors used internally and externally by the respirator 950, real time information data received from external IoT network and IoT devices, and IoT biometric devices attached to the body of user of respirator 950 to determine how to control the regulator. The regulator controls the amount of oxygen needed to be mixed in inlet assembly 957 with filtered air from the environment before sending it into the interior of the face mask 951 due to the following reasons.

Real time reduction in the pressure of the stored oxygen in the oxygen tank 1218 while being used.

Information data collected by AI from biometric devices attached to the body of the person using the respirator.

Information data collected by AI from some sensors used by the respirator such as the elevation that respirator 950/1900 is used.

Information data received by AI from medical doctors or staff monitoring the person using the respirator through IoT network and smart devices.

Information data collected by AI from some sensors used by respirator 950/1900 such as the environment the respirator is used.

Information data collected by AI from some sensors used by the respirator such as the movement of the person using the respirator.

Figure 4E:
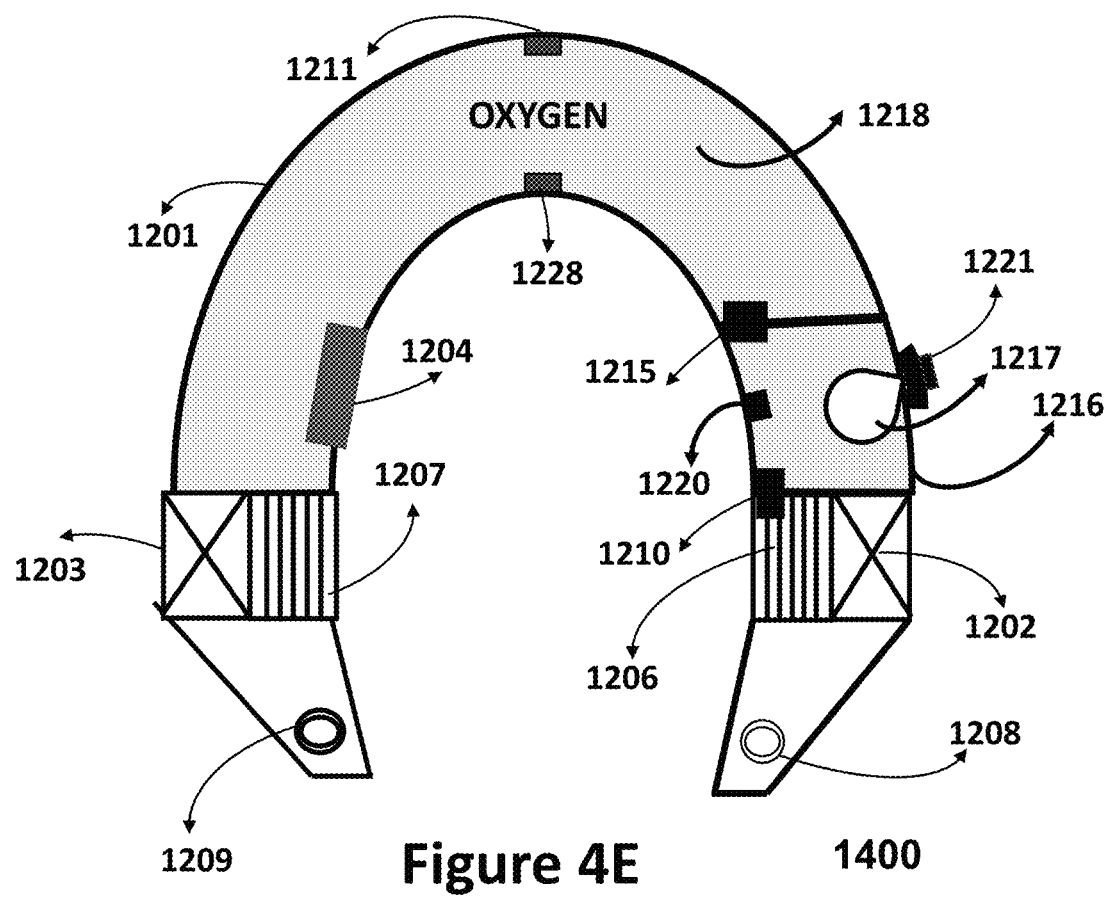
FIG. 4E shows a wearable device with a regulator that uses an airbag that is externally inflated and deflated.

FIG. 4E depicts a wearable device (neck hanger) 1400 with a regulator that is controlled manually. The regulator used in FIG. 4E, like regulator shown in FIG. 4C, uses an airbag to control the amount of oxygen mixed in inlet assembly 957 with filtered air from the environment before sending it into the interior of face mask 951/1904. The manually controlled regulator of FIG. 4E comprises of an oxygen container 1216 that holds the released oxygen from oxygen tank 1218, an airbag 1217 acting as loading mechanism, a sensor 1220 that senses the oxygen pressure and reports to control circuit 1204, an inlet valve 1215, an outlet valve 1210, and an external valve 1221 which acts as an air inlet and air outlet for the airbag 1217. When there is no inflating and deflating of airbag the valve 1221 stops the environmental air to enter the airbag and the air inside the airbag to exit to the environment. Sensor 1228 measures the oxygen pressure within the oxygen tank and sends the result to the CPU of control circuit 1204 to be used by AI algorithm. The oxygen pressure within oxygen tank 1218 is reduced as it is being used by the respirator 950/1900 and as a result the regulator needs to adjust its container 1216 internal oxygen pressure to maintain steady output at the outlet valve 1210.

Figure 4F:
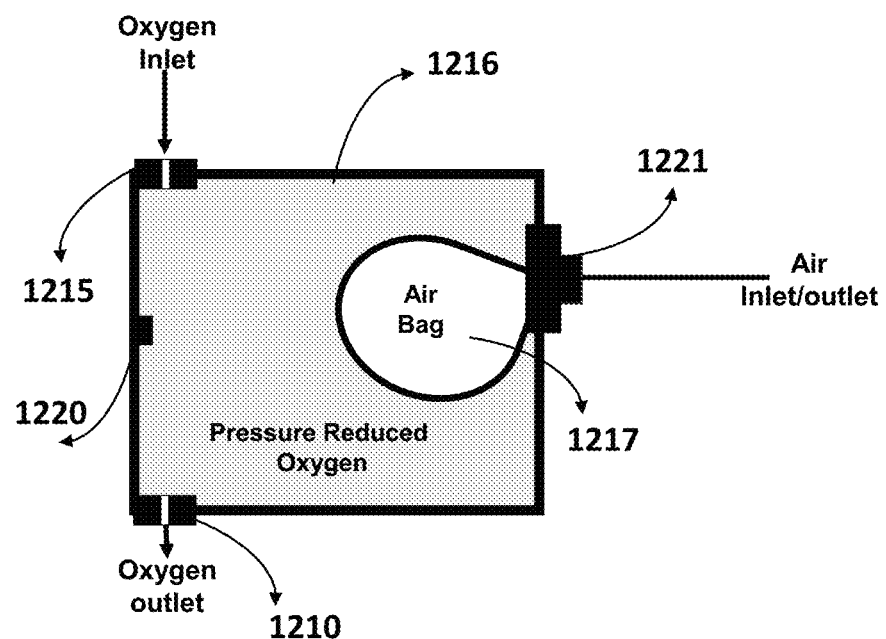
FIG. 4F illustrates the structure of a regulator using an airbag with external method of inflating and deflating.

FIG. 4F shows the detailed structure of manually controlled regulator. Airbag 1217 is used to control the amount of oxygen leaves the valve 1210 that mixes in inlet assembly 957 with filtered environment air before being sent into the interior of the face mask 951/1904. Sensor 1220 measures the oxygen pressure inside container 1216 and sends the measured data to control circuit's CPU (central processing unit). The CPU's AI algorithm uses the real time measured data from sensor 1220, the configuration data, real time information data collected by other sensors used internally and externally by respirator 950/1900, real time information data received from external IoT network and IoT devices, and IoT biometric devices attached to the body of user of respirator 950/1900 to determine how to control the regulator. The control is done by inflating and deflating the airbag. The inflating and deflating of airbag 1217 are done manually through the external valve 1221 by the person using respirator 950/1900 or medical staff that monitor the person. The AI uses vibration of wearable device 1400, an LED light on the respirator, an alarm sound, a message/alarm to an IoT smart device wirelessly (using Bluetooth, WiFi, Zigbee, infra-red, or any other wireless protocol), or a message/alarm through IoT network to a smart phone/device, computer or tablet to indicate that the pressure of the oxygen within the regulator needs to be adjusted. The medical staff or the person using the respirator manually adjusts the oxygen pressure within container 1216 using the inlet/outlet external valve 1221. This is done by inflating or deflating the airbag using mouth or an air pump. The person or medical staff, while inflating or deflating airbag 1217 monitor the LED until the light goes green or watch a smart phone/device that shows when the inflation or deflation needs to stop.

Figure 4G:
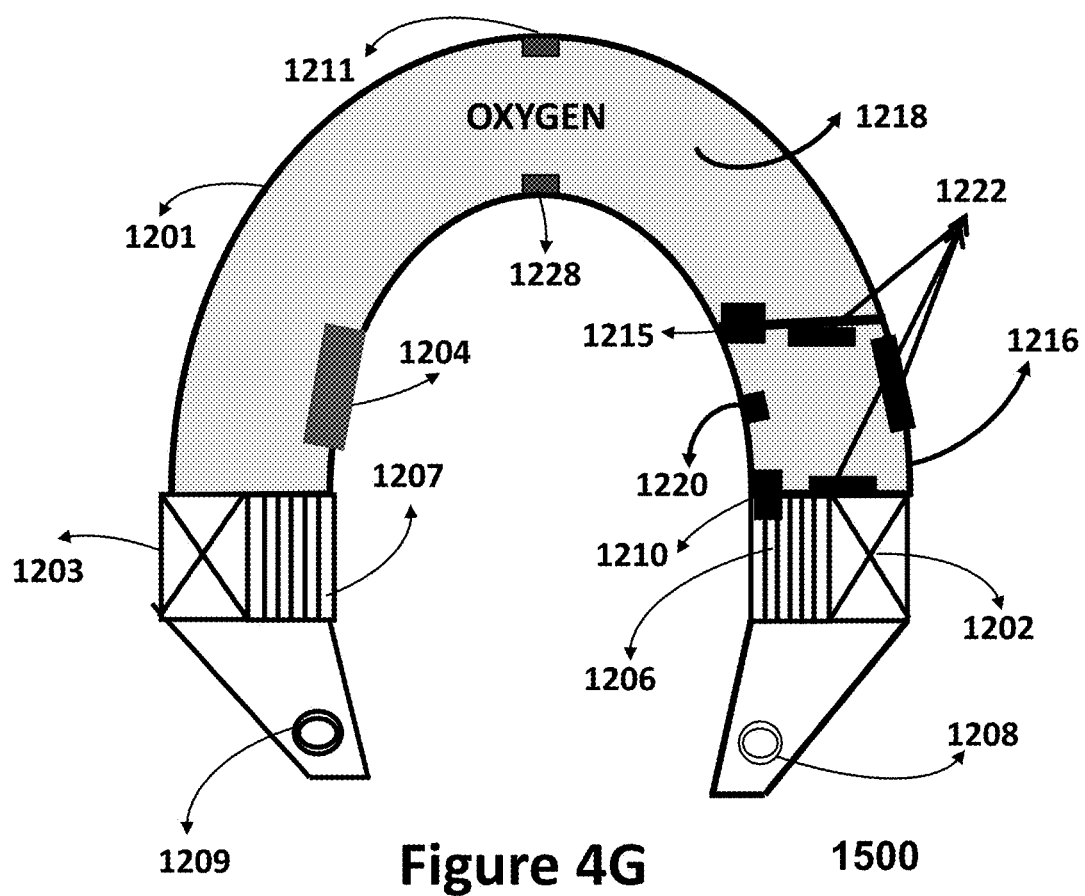
FIG. 4G shows a wearable device with a regulator that uses expandable (contractable) pads.

FIG. 4G depicts a wearable device (neck hanger) 1500 with a regulator. The regulator comprises of an oxygen container 1216 that holds the released oxygen from oxygen tank 1218, expandable pads 1222 acting as loading mechanism, a sensor 1220 that senses the oxygen pressure inside the regulator and reports to the control circuit 1204, an inlet valve 1215, and an outlet valve 1210. The regulator is attached to the oxygen tank 1218, and through inlet 1215 receives oxygen. It is also attached to inlet assembly 957 (fan 1202 and filter 1206) for delivering oxygen through outlet valve 1210 to be mixed with the filtered air from the environment. The expandable pads 1222 are increased in size by applying a voltage to them from control circuit 1204 under the control of AI algorithm in the CPU. AI determines to apply voltage to which expandable pad as well as the amount of voltage. By applying voltage to the expandable pads, the amount and pressure of the oxygen at the outlet 1210 is controlled. The regulator's container 1216 can be stand alone or an integral part of oxygen tank 1218 of wearable device 1500 which is the neck hanger of FIG. 4G.

Figure 4H:
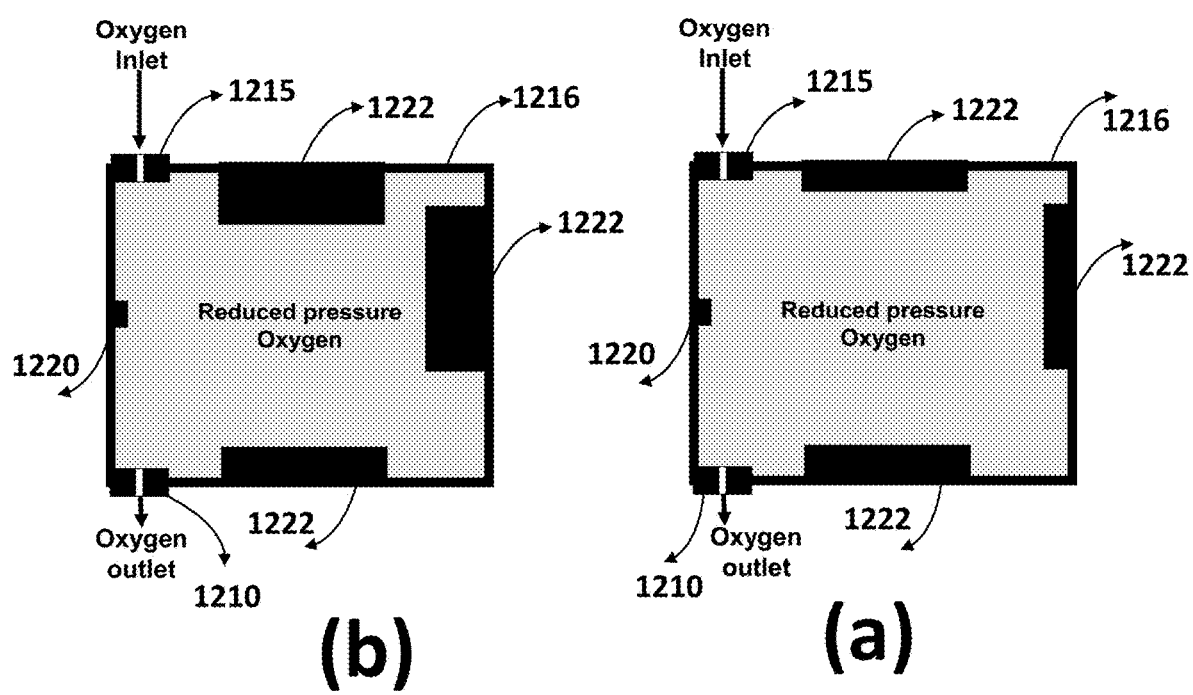
FIG. 4H illustrates the structure of a regulator using expandable (contractable) pads to control the oxygen pressure within the regulator by applying voltage across the two ends of the pads.

FIG. 4H shows the structure of the regulator used in wearable device 1500. The drawing "a" on the right of FIG. 4H illustrates container 1216 that holds the oxygen that its pressure is controlled by expandable pads 1222. Valve 1215 injects oxygen from oxygen tank 1218 into container 1216. By applying voltage across one or more expandable pads 1222 within the container 1216 as shown in drawing "b" in FIG. 4H the volume of the container 1216 is decreased or increased which results in increasing and decreasing the oxygen pressure inside container 1216. This controls the pressure and amount of the oxygen which is released from valve 1210 to be mixed in inlet assembly 957 with the air that is sucked (pulled in) from the environment by fan 1202 and filtered by filter 1206 before being released into the interior of face mask 951. The control of the voltage that is applied across one or more expandable pads 1222 is done by sensor 1220 and control circuit 1204. The sensor 1220 real time measures the oxygen pressure within the container 1216 and sends the data to control circuit 1204, The control circuit 1204 also uses the information data it receives from other sensors of respirator 950/1900, from IoT network, from IoT device (smart phones. tablet, laptop, and any smart wireless device), and from IoT biometric devices that are attached to the body of the person using respirator 950/1900. An artificial intelligence (AI) algorithm executed in the CPU of control circuit 1204 analyzes all the information data to determine when and the amount of voltage that is required to be applied across one or more expandable pads 1222.

Expandable pad is an electroactive polymer (EAP) that exhibits a change in size or shape when stimulated by voltage. In the early 1990s, ionic polymer-metal composites (IPMCs) were developed and shown to exhibit electroactive properties far superior to previous EAPs. The major advantage of IPMCs was that they were able to show activation (deformation) at voltages as low as 1 or 2 volts. This is orders of magnitude less than any previous EAP. Not only was the activation energy for these materials much lower, but they could also undergo much larger deformations. IPMCs were shown to exhibit anywhere up to 380% strain, orders of magnitude larger than previously developed EAPs.

The regulator uses a plurality of expandable pads inside container 1216. Each time control circuit 1204 decides to adjust the oxygen pressure inside the regulator it activates one or more expandable pads from the plurality of expandable pads and activates them by applying voltage across them.

Figure 4I:
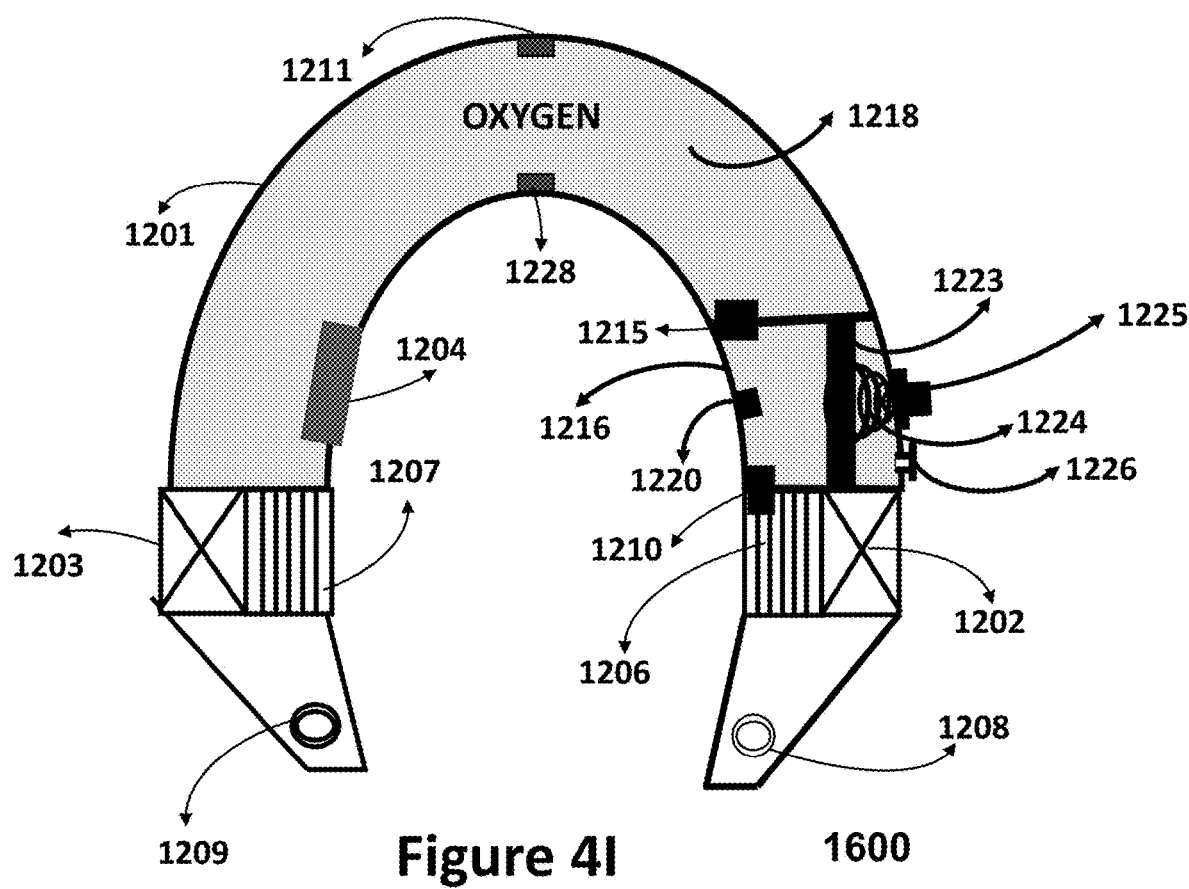
FIG. 4I shows a wearable device with a regulator that uses an internal moving piston using a spring.

FIG. 4I depicts a wearable device (neck hanger) 1600 with a regulator that is controlled manually. The regulator uses a spring as the loading mechanism to control the amount of oxygen mixed in the inlet assembly 957 with filtered air from the environment before sending it into the interior of face mask 951/1904. The manually controlled regulator of FIG. 4I comprises of an oxygen container 1216 that holds the released oxygen from oxygen tank 1218, a spring 1224 acting as loading mechanism, a sensor 1220 that senses the oxygen pressure and reports to the control circuit 1204, an inlet valve 1215, an outlet valve 1210, an external hand nob 1225 to compress and decompress spring 1224, a spring head 1223 to stop oxygen leak out of the loading mechanism (spring 1224, hand nob 1225, and ring head 1223), and an aperture 1226 for keeping the environment air pressure inside the loading mechanism. Sensor 1228 measures the oxygen pressure within the oxygen tank and sends the result to the control circuit CPU to be used by AI algorithm. The oxygen pressure within oxygen tank 1218 is reduced as it is being used by the respirator 950/1900 and as a result the regulator 1216 needs to adjust its container 1216 internal oxygen pressure to maintain steady output at the outlet valve 1210. The regulator can be stand alone or an integral part of oxygen tank 1218 of wearable device which is the neck hanger of FIG. 4I.

Figure 4J:
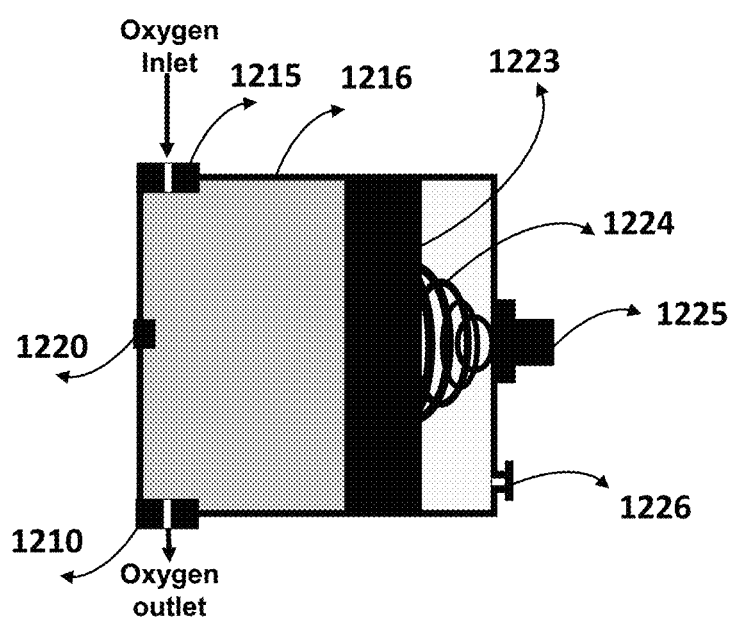
FIG. 4J shows a regulator that uses an internal moving piston controlled by external nobs.

FIG. 4J shows the detailed structure of manually controlled regulator used in wearable device 1600. Spring 1224 is used to control the amount of oxygen leaves valve 1210 that in inlet assembly 957 mixes with filtered environment air before being sent into the interior of face mask 951/1904. Sensor 1220 measures the oxygen pressure inside container 1216 and sends the measured data to control circuit's CPU (central processing unit). The CPU's AI algorithm uses the real time measured data from sensor 1220, the configuration data, real time information data collected by other sensors (including the oxygen tank 1218) that are internally and externally attached to respirator 950/1900, real time information data received from external IoT network and IoT devices, and data from IoT biometric devices attached to the body of user of respirator 950/1900 to determine how to control the regulator. The control is done by compressing or decompressing spring 1224. This is done manually through external nob 1225 by the person using the respirator or medical staff that monitor the respirator. The AI uses vibration of the respirator, an LED light on the respirator, an alarm sound, a message/alarm sent to an IoT smart device wirelessly (using Bluetooth, WiFi, Zigbee, infra-red, or any other wireless protocol), or a message/alarm through IoT network sent to a smart phone, computer or tablet to inform the person using the respirator or the medical staff monitoring it that the oxygen pressure within the regulator is dropped below a required threshold. The medical staff or the person using the respirator manually adjusts the oxygen pressure within the regulator's container using external nob 1225. This is done by compressing or decompressing spring 1224. The wearer or medical staff while compressing or decompressing the spring 1224 monitors the LED until the light goes green or watches a smart phone/device that shows when the compressing or decompressing needs to stop. While spring 1224 is compressed or decompressed the spring head 1223 stops oxygen from left side of spring head 1223 leaks to its right side.

Figure 4K:
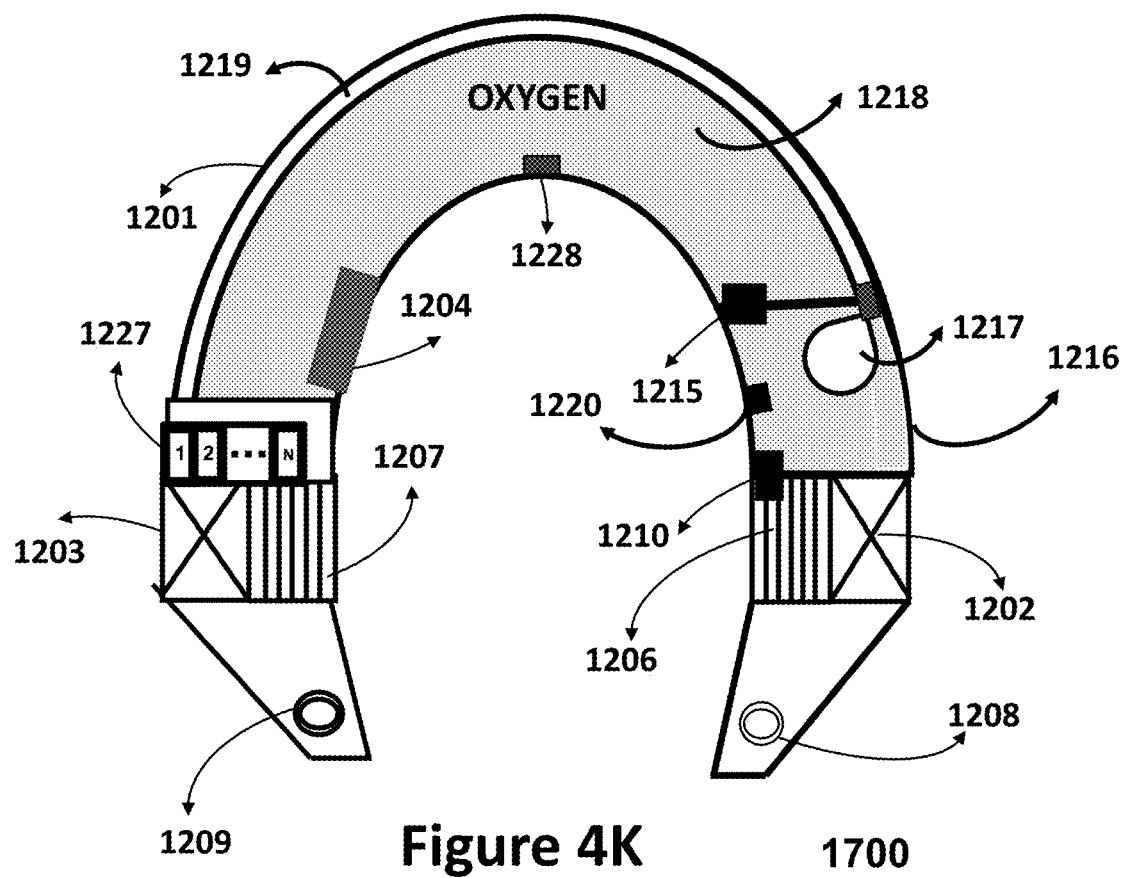
FIG. 4K shows a wearable device with a regulator using an airbag that is internally inflated using inflating cartridges and deflated through air duct and a valve connected to the exhaust assembly.

FIG. 4K depicts a wearable device (neck hanger) 1700 with a regulator using inflator cartridge. The regulator comprises of an oxygen container 1216 that holds the released oxygen from oxygen tank 1218, an airbag 1217 acting as loading mechanism, a sensor 1220 that senses the oxygen pressure and reports to the control circuit 1204, an inlet valve 1215, and an outlet valve 1210. The regulator is attached to the oxygen tank 1218 and through inlet 1215 receives oxygen. It is also attached to air inlet assembly 957 with fan 1202 and filter 1206 for delivering oxygen through outlet valve 1210 to be mixed with the filtered air from the environment. The airbag 1217 is inflated and deflated through air duct 1219 and inflator cartridge/deflator valve 1227 which is attached to exhaust assembly (fan 1203 and filter 1207) 958. The inflation and deflation of the airbag 1217 is controlled by pressure sensor 1220 and control circuit 1204. By inflating and deflating the airbag the amount and pressure of the oxygen at the outlet 1210 is controlled. The regulator can be stand alone or an integral part of oxygen tank 1218 of wearable device 1700 which is the neck hanger of FIG. 4K.

FIG. 4L shows the implementation of the regulator. The drawing "a" on the right of FIG. 4L illustrates container 1216 that holds the oxygen that its pressure is controlled by airbag 1217. Valve 1215 injects oxygen from oxygen tank 1218 into container 1216. By inflating and deflating airbag 1217 the volume of the container 1216 is decreased or increased which results in increasing and decreasing of the oxygen pressure in container 1216 and the pressure and amount of the oxygen which is released from valve 1210. The released oxygen from valve 1210 mixes in inlet assembly 957 with the air that is sucked (pulled in) from the environment by fan 1202 and filtered by filter 1206 before being released into the interior of the mask 951/1904. The control of inflating and deflating airbag 1217 is done by sensor 1220 and control circuit 1204. The sensor 1220 real time measures the oxygen pressure within container 1216 and sends the data to control circuit 1204. The control circuit 1204 also uses the information data it receives from other sensors of the respirator 950/1900 and information data from IoT network, IoT device (smart phones, tablet, laptop, and any smart wireless device), and IoT biometric devices that are attached to the body of the person using the respirator by its artificial intelligence (AI) algorithm to determine when to inflate or deflate the airbag.

Inflating and deflating of the airbag is done internal to wearable device (neck hanger) 1700. The airbag through an air pipe (tube) 1219 is connected to valve 1214. The drawing "b" of valve 1214 is shown on the left side of FIG. 4L. Valve 1227 has two apertures. One of them that is connected to the air pipe (tube) 1219 is used as both inlet (during inflating) and outlet (during deflating). The other aperture is connected to the exhaust assembly between exhaust fan 1203 and exhaust filter 1207 and is used as an outlet only. One of these two apertures is used as inlet during inflating while the other aperture is closed. The two apertures are open and used as outlets during deflating. The design of valve 1227 is not the subject of this application. The inflating is done by triggering one of the inflators within the inflator cartridge. The inflator cartridge houses multiple inflators and when needed triggers one or more of them. Inflators, when triggered due to a chemical reaction, release nitrogen gas (or any other safe gas) that inflates the airbag. The amount of nitrogen gas (or any other safe gas) that each cartridge releases can be equal or different. The inflators are triggered by the control circuit's AI algorithm. When the airbag needs to be inflated the outlet valve is closed and when the airbag is deflated the outlet is open and the air inside the airbag is sucked out by the exhaust fan and released to the environment.

Figure 4M:
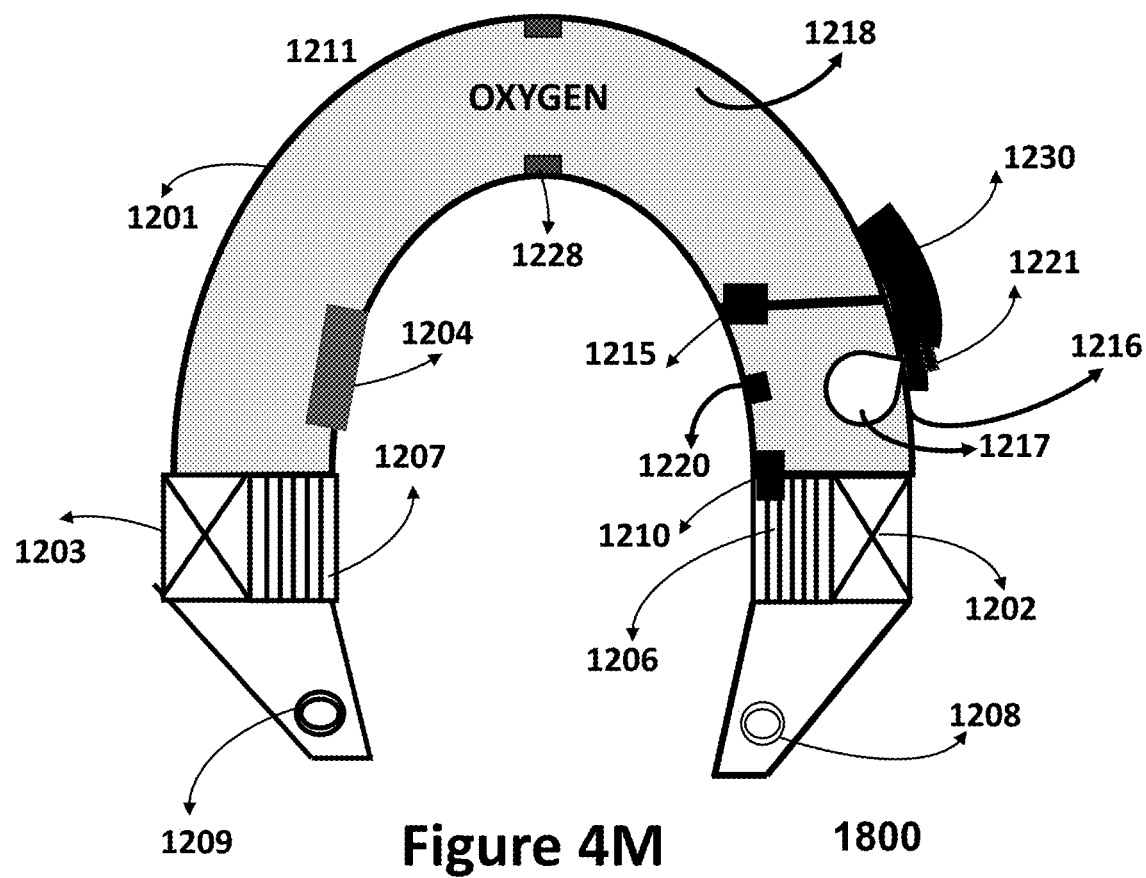
FIG. 4M shows a wearable device with a regulator using an airbag that is inflated and deflated using an integrated air pump.

FIG. 4M depicts a wearable device (neck hanger) 1800 with a regulator that uses an integrated air pump. The regulator comprises of an oxygen container 1216 that holds the released oxygen from oxygen tank 1218, an airbag 1217 acting as loading mechanism, a sensor 1220 that senses the oxygen pressure and reports to the control circuit 1204, an inlet valve 1215, and an outlet valve 1210. The regulator is attached to the oxygen tank 1218 and through inlet 1215 receives oxygen. It is also attached to air inlet assembly 957 (that holds fan 1202 and filter 1206) for delivering oxygen through outlet valve 1210 to be mixed with the filtered air from the environment. The airbag 1217 is inflated and deflated through valve 1221 which is attached to an external air pump 1230. The inflation and deflation of the airbag 1217 is controlled by pressure sensor 1220 and control circuit 1204. By inflating and deflating the airbag the amount and pressure of the oxygen at the outlet 1210 is controlled. The regulator can be stand alone or an integral part of oxygen tank 1218 of wearable device which in this example is the neck hanger of FIG. 4M. The process to control inflating and deflating of the airbag by the AI algorithm executed in the CPU of the control circuit 1204 is like solutions used in FIGS. 4C, 4G, and 4K.

Figure 4N:
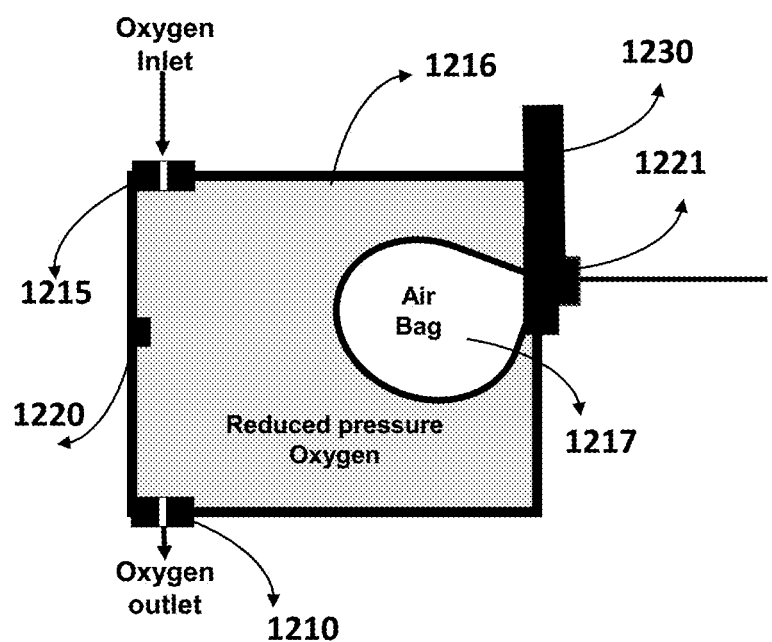
FIG. 4N shows the structure of a regulator using an airbag and integrated air pump.

FIG. 4N shows the implementation of the regulator used by wearable device 1800. Container 1216 holds the oxygen that its pressure is controlled by airbag 1217. Valve 1215 injects oxygen from oxygen tank 1218 into container 1216. By inflating and deflating airbag 1217 the volume of the container 1216 is decreased or increased which results in increasing and decreasing the oxygen pressure in the container 1216 and the pressure and amount of the oxygen which is released from valve 1210. The oxygen released from valve 1210 is mixed in inlet assembly with the air that is sucked (pulled in) from the environment by fan 1202 and filtered by filter 1206 before being released into the interior of the mask 951/1904. The control of inflating and deflating airbag 1217 is done by sensor 1220 and controller circuit 1204. The sensor 1220 real time measures the oxygen pressure within container 1216 and sends the data to controller 1204. The controller 1204 also uses the information data it receives from other sensors of the respirator 950/1900 and information data from IoT network, IoT device (smart phones, tablet, laptop, and any smart wireless device), and IoT biometric devices (that are attached to the body of the person using the respirator) by its artificial intelligence (AI) algorithm to determine when to inflate or deflate the airbag. The inflating and deflating are performed by air pump 1230 attached to valve 1221. The air pump 1230 functions as an air blower and air sucker by change of polarity of DC voltage applied to it from control circuit 1204 controlled by the AI algorithm. It is also possible to use other methods or solutions to make the air pump act as a blower and sucker of air.

In all regulators of FIGS. 4C to 4N the control circuit that resides in housing 1204 plays the main role in controlling the function of regulator and ultimately the respirator. The control circuit has a CPU that executes an AI algorithm to control various functions of the respirator 950/1900. The AI algorithm relies on all or subset of following information data to manage and control the function of the respirator:

I. the information data from various sensors installed internal or external in the respirator,
II. information data obtained from biometric devices that are attached to the person who is using the respirator,
III. information data obtained from external devices that directly communicate with the control circuit using wireless protocols mentioned earlier,
IV. information data obtained from IoT devices through IoT networks used by medical staff or the person wearing the respirator, and
V. any information data from manual keys or buttons, and nobs installed externally on the respirator.

All the valves used in the wearable device can be controlled to have a specified air flow. Manual valves are controlled manually by turning a handle or lever. They are commonly used in low-pressure and low-flow applications where automated control is not required. Automatic valves are controlled by an actuator, which is powered by electricity, air, or hydraulic pressure. The control circuit in power housing 1204 as mentioned before controls all functions of the respirators 950/1900 which includes controlling the air flow of all the valves. The control of the valves includes opening and closing them as well as the amount of air flow when they are open. This function also allows use of oxygen when is needed by specifying a time window oxygen is used and a time window no oxygen is mixed with filtered environmental air in the inlet assembly. All these features are controlled by AI algorithm and are considered when control of oxygen pressure within the regulator is performed. The design of air valves and oxygen valves are not subject to this disclosure.

The sensors measure the pressure and the flow of the oxygen and send the information to the control circuit that is in the battery or power housing. The wearer device can have a single housing for a single battery to power both inlet assembly sucking fan 1202 and exhaust assembly sucking fan 1203. The speed of the fans is controlled by the control circuit by changing the DC (direct current) voltage applied to the sucking fans 1202 and 1203. The power housing for battery and control circuit can have a USB port or other power ports for charging the battery. The USB port is also used for communication between control circuit and external device. The control circuit can also use a wireless transceiver like Bluetooth, Zigbee, Infrared, or WiFi (wireless fidelity) to communicate with external devices.

The control circuit within the power housing performs several tasks. One of the tasks is to control the speed of the fans by changing the DC voltage applied to the fans. The control circuit based on the information data it obtains from various sensors (in the air pipes, inside the face mask), configuration data, IoT network, smart devices, and biometric devices decides what voltage to apply to the sucking fans 1202 and 1203. The decision is made by an artificial intelligence (AI) algorithm that is executed in the control circuit's CPU (central processing unit). A second task is to monitor the amount of charge of the batteries through appropriate sensors and use an LED (light emission diode) which is capable of deeming, a red LED when the charge is below a threshold, or communication to an external device like smart phone the amount of available charge. A third task is to monitor the pressure of oxygen tank and estimate the amount oxygen in the tank and indicate when the tank needs to be refilled through a red LED or communicating with an external device. A fourth task is to use the oxygen pressure measured within the regulator and facilitate increasing or lowering the oxygen pressure at the outlet of the regulator. A fifth task is to connect to an external device and configure respirator 950/1900. The configurations parameters are initial operating parameters of respirator 950/1900 that include various thresholds, and settings. Another task of control circuit is to perform diagnostic and alarms.

Figure 5:
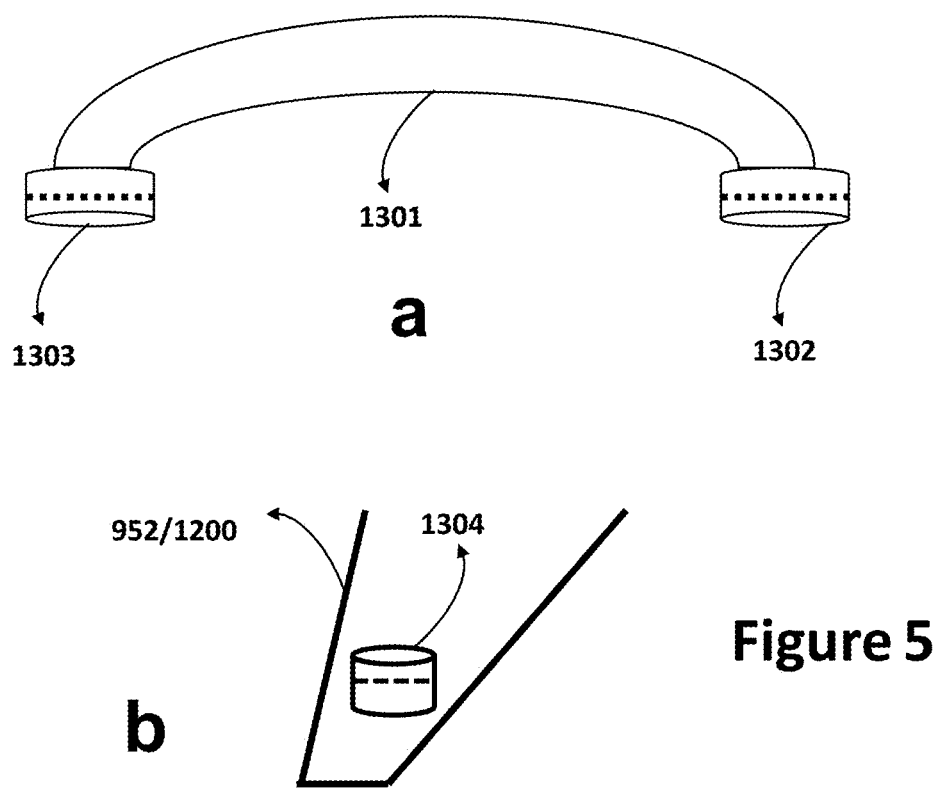
FIG. 5 illustrates the air pipe (tube) that carries air to the face mask and its connection port to the wearable device.

FIG. 5 shows flexible air pipe 953/954 in drawing "a" and outlet or inlet of wearable device (neck hanger) 952/1200 in drawing "b". Flexible air pipe 953/954 comprises of air pipe 1301 and female heads 1302 and 1303. Female heads 1302 and 1303 are used to connect the flexible pipe 953/954 to face mask 951 and wearable device (neck hanger) 952/1200. Wearable device (neck hanger) 952/1200 has the male head 1304 for the female head 1302 of air pipe 1301.

There are various methods of connecting the air pipe 1301 to the wearable device (neck hanger). Flexible pipe fittings are available in a variety of shapes and materials. Some of these methods are:

a) Push fitting.
b) Press fitting.
c) Telescopic tube fitting
d) Telescopic tube lock
e) Telescoping clamp
f) Telescoping tube pushing
g) Telescopic tube by quick connect.
h) Using threaded male and female heads Female head 1303 of the flexible (or solid) pipe 1301 is for connecting to face mask 951. Female head 1303 can be different from female head 1302 due to its connection to the mask. Instead of female head it is possible to use a male head for 1303 and have the female head on the face mask 951. The same can be applied to head 1302, use male head for 1302 and have the female head on the wearable device (neck hanger).

The air pipe 953/954 is flexible and its length changes when the head of the person wearing the mask with neck hanger moves left, right, down, and up. The air pipe (tube) expands like an expandable hose when there is a need. The flexible pipe 953/954 expands when the head moves and shrinks to its original length when head returns.

Figure 6A:
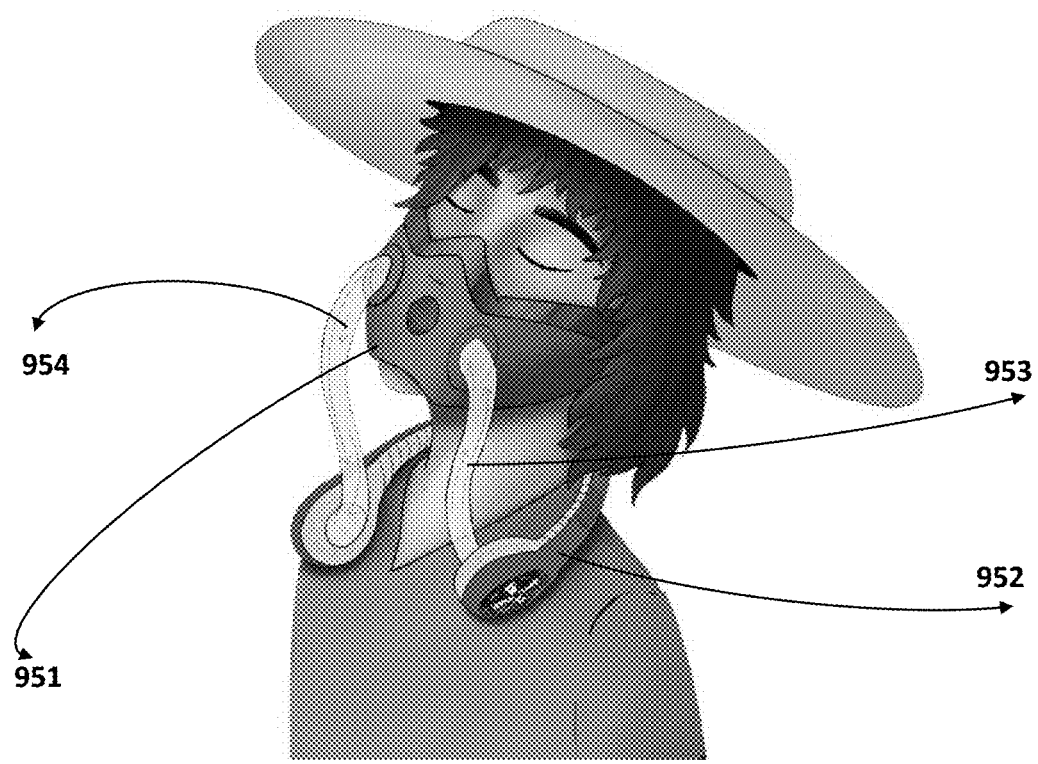
FIG. 6A shows a typical industrial design for respirators using a face mask with wearable device.

FIG. 6A depicts a typical industrial design for novel respirator 950. This figure shows one implementation of wearable device (neck hanger) 952/1200 with fans located at either end whether a "U" shape, horseshoe shape, or proprietary shape is used. Wearable device (neck hanger) 952/1200 may be flexible and the person who wears it being able to adjust it for comfort. The air pipes (tubes) 953 and 954 are also flexible to allow easy connection to face mask 951 and wearable device (neck hanger) 952 and provide a comfortable feeling for the person who wears respirator 950. The flow of the air is from air pipe 953 to air pipe 954 through the interior of face mask 951. This flow of the air will not be disturbed due to the direction the sucking fans suck the air and blow the air.

Figure 6B:
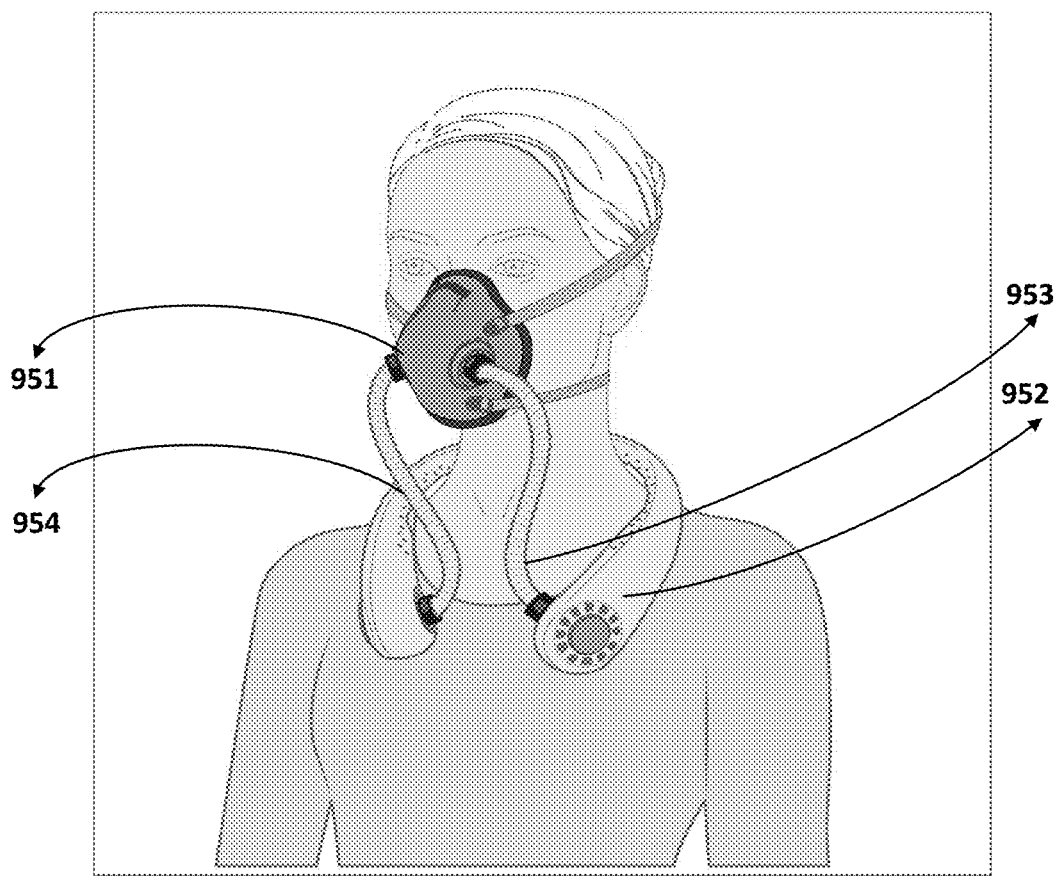
FIG. 6B illustrates how a respirator with a face mask and a wearable device is worn by a person.
Figure 6C:
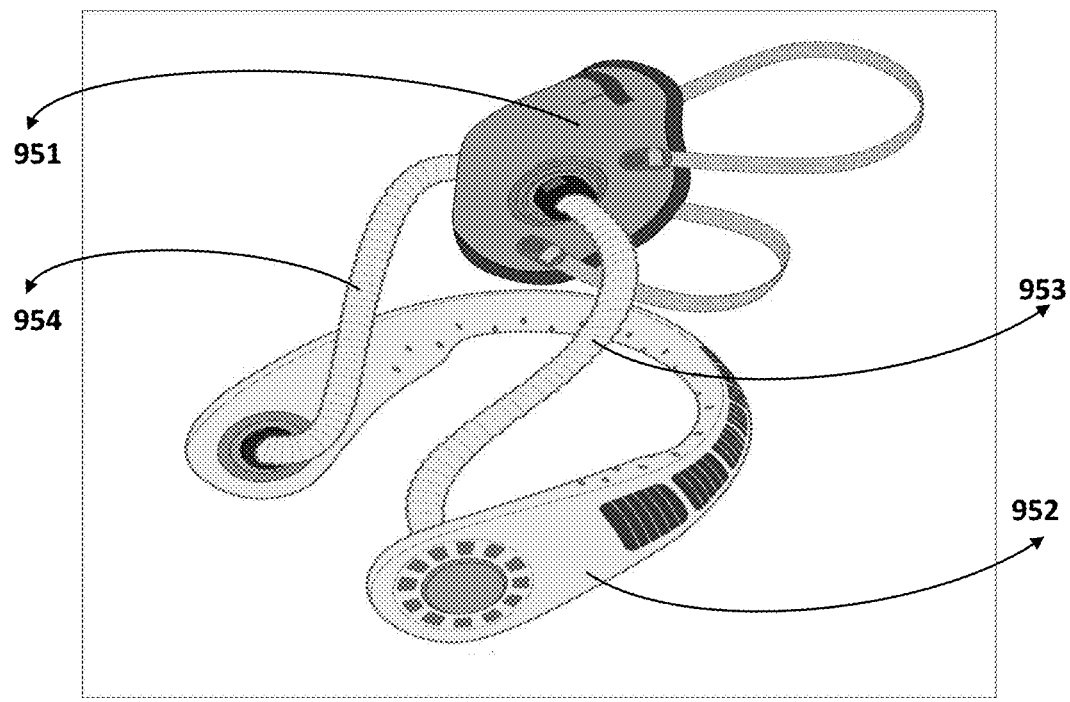
FIG. 6C depicts various components of a respirator with a face mask and a wearable device.
Figure 6D:
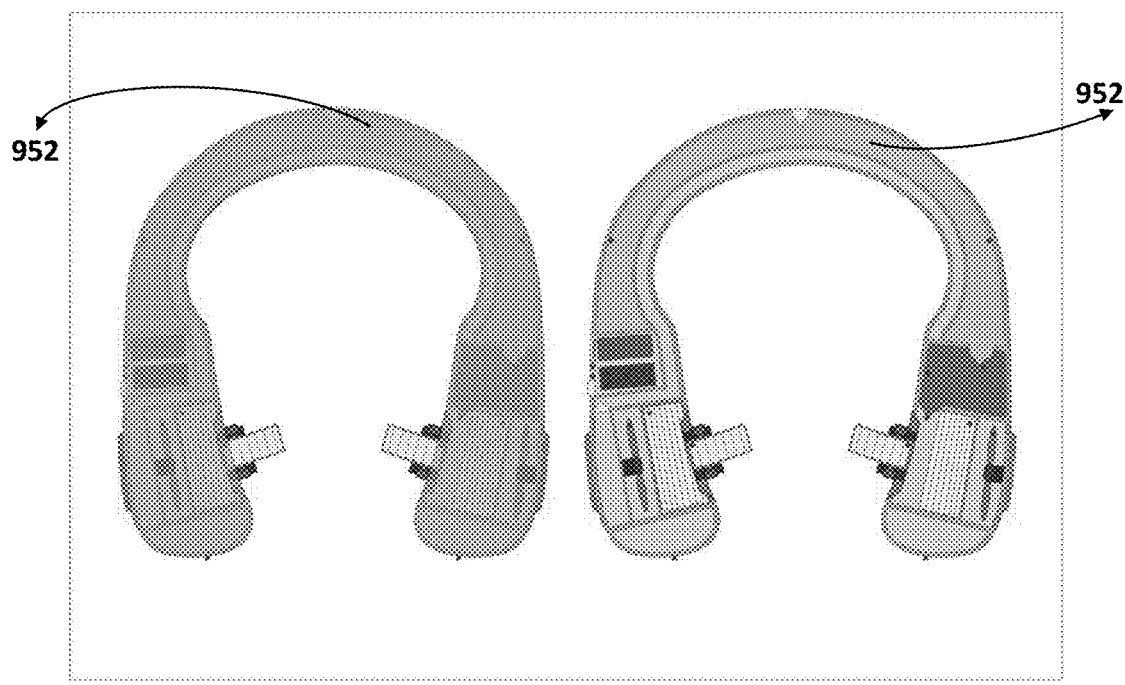
FIG. 6D shows the cross-section views of the wearable device.

FIG. 6B shows how face mask 951 with wearable device (neck hanger) 952/1200 is worn by a person. It shows how the face mask is attached to the face and how the air pipes are connected to the face mask and wearable device (neck hanger). FIG. 6C shows the respirator 950/1900 with all the components. It also shows where the mini solar cells are connected and where the cooling apertures or holes are located. FIG. 6D depicts the cross-section views of the wearable device (neck hanger) 952/1200.

Figure 6E:
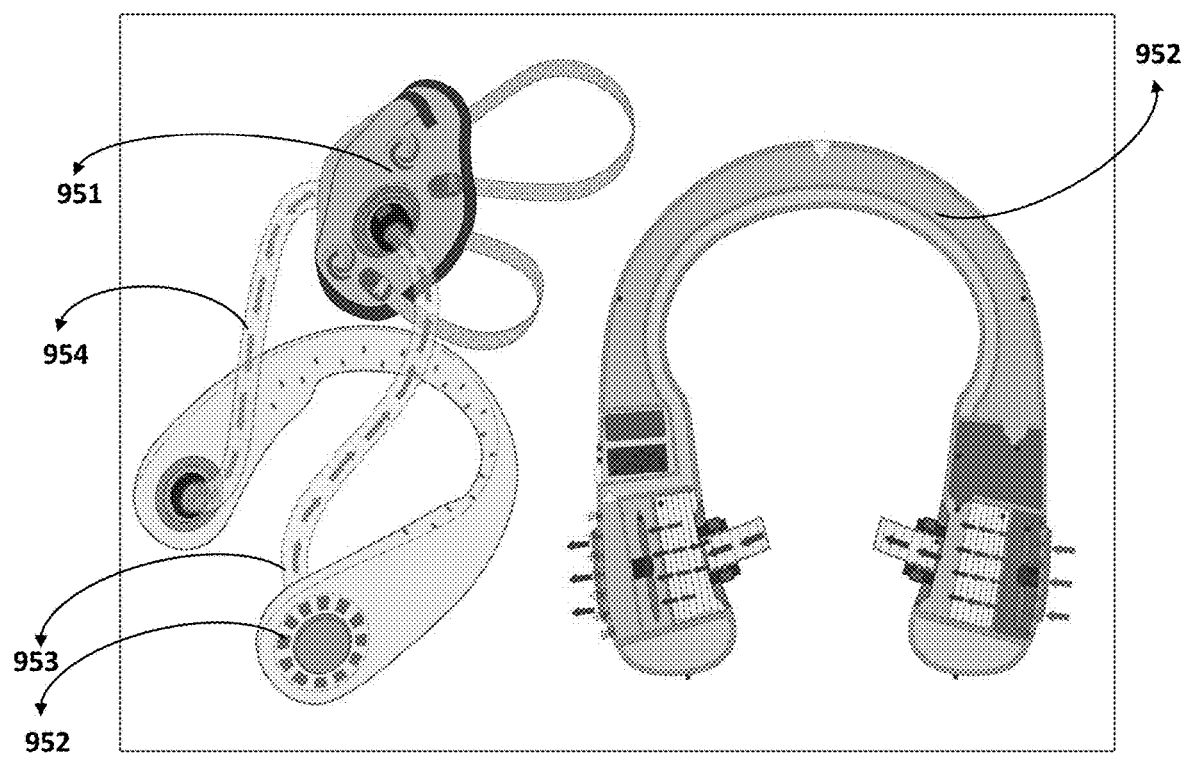
FIG. 6E illustrates the direction of air flow within the wearable device, air pipes (tubes) and the face mask.

FIG. 6E illustrates the direction of air flow within the wearable device (neck hanger), air pipes (tubes) and the face mask. The air from the environment that is contaminated is sucked by fan 1202, filtered by filter 1206 and then clean air is blown into the interior of the face mask through air pipe 953. The clean air inside the mask becomes contaminated due to exhaling of the person wearing the mask, then the contaminated air is sucked out (pulled out) of the interior of the mask by fan 1203 through air pipe 954, filtered by filter 1207 and then clean air is released back to the environment.

Figure 6F:
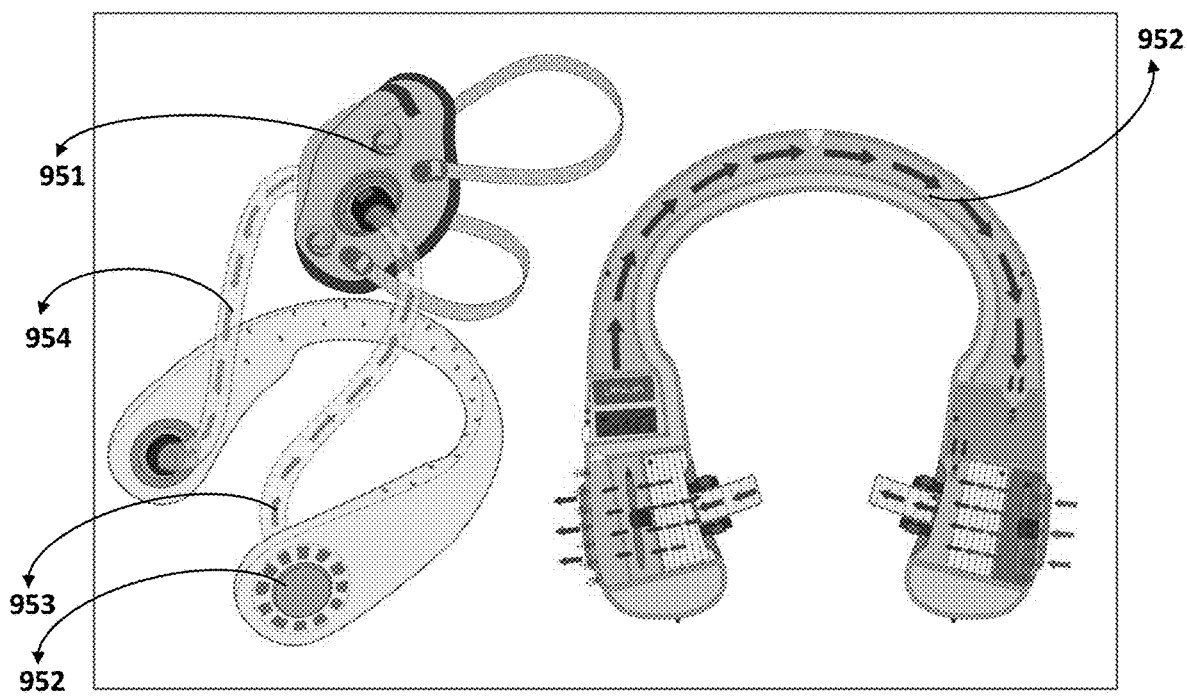
FIG. 6F depicts the airflow within the wearable device when oxygen is mixed with the air that is flowing into the interior of the face mask.

FIG. 6F depicts how oxygen is added to the air that is sent into the interior of the face mask. The contaminated air from the environment is sucked by fan 1002, filtered and cleaned by filter 1006, then oxygen is added to the clean air and then mix of clean air and oxygen is sent into the interior of the face mask through air pipe 953. The clean air inside the interior of the mask becomes contaminated due to exhaling of the person wearing the face mask, then the contaminated air is sucked out (pulled out) of the interior of the face mask by fan 1003 through air pipe 954, filtered by filter 1007 and clean air is released back to the environment.

FIG. 6G shows how the cleaned interior air of the face mask is used for cooling the neck and head. The contaminated air from interior of the face mask is sucked through air pipe 954, filtered by filter 1207, then blown out towards the neck and head through apertures or holes 1110.

Figure 6H:
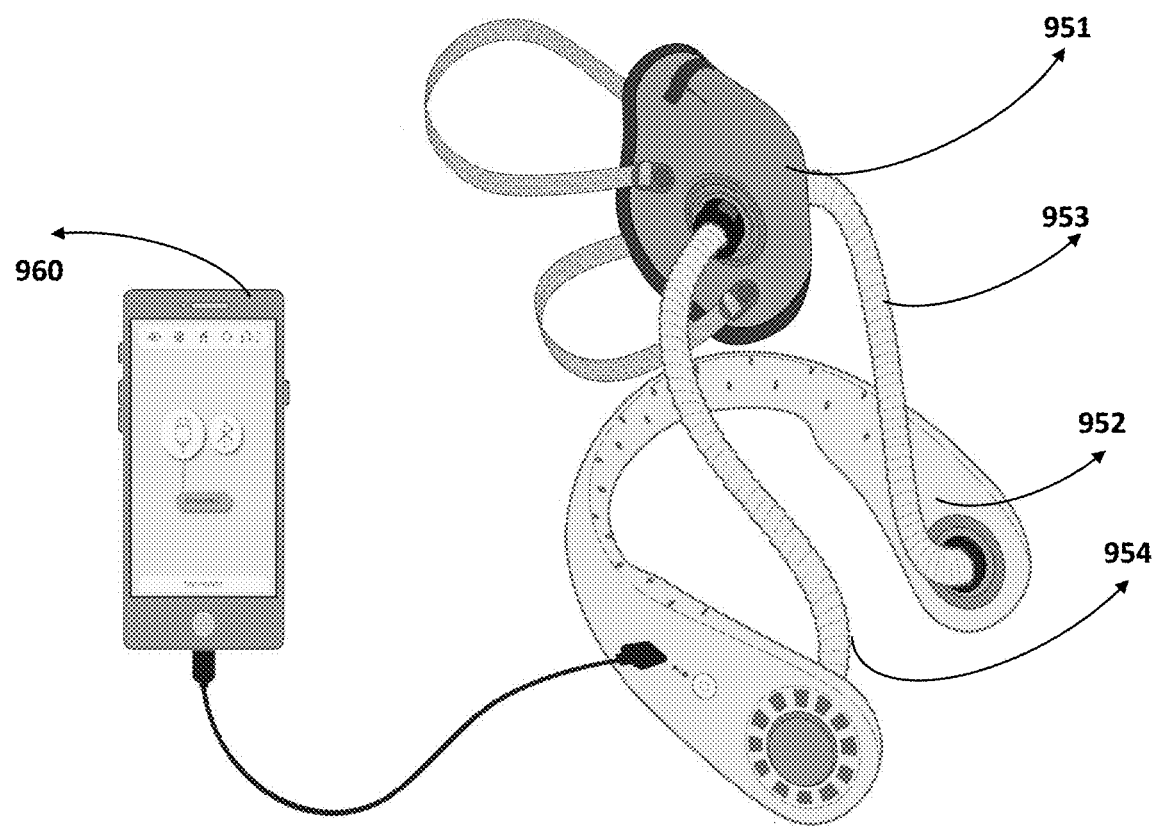
FIG. 6H illustrates connection of the respirator with a face mask and a wearable device to an external device using a USB cable.

FIG. 6H illustrates communication of respirator 950/1900 with an external device using a USB cable. The USB cable end ports can be different for the external device. Wearable device (neck hanger) 952/1200 uses the USB end of the cable but the end that is connected to the device can be a proprietary port specific to the external device.

Figure 6I:
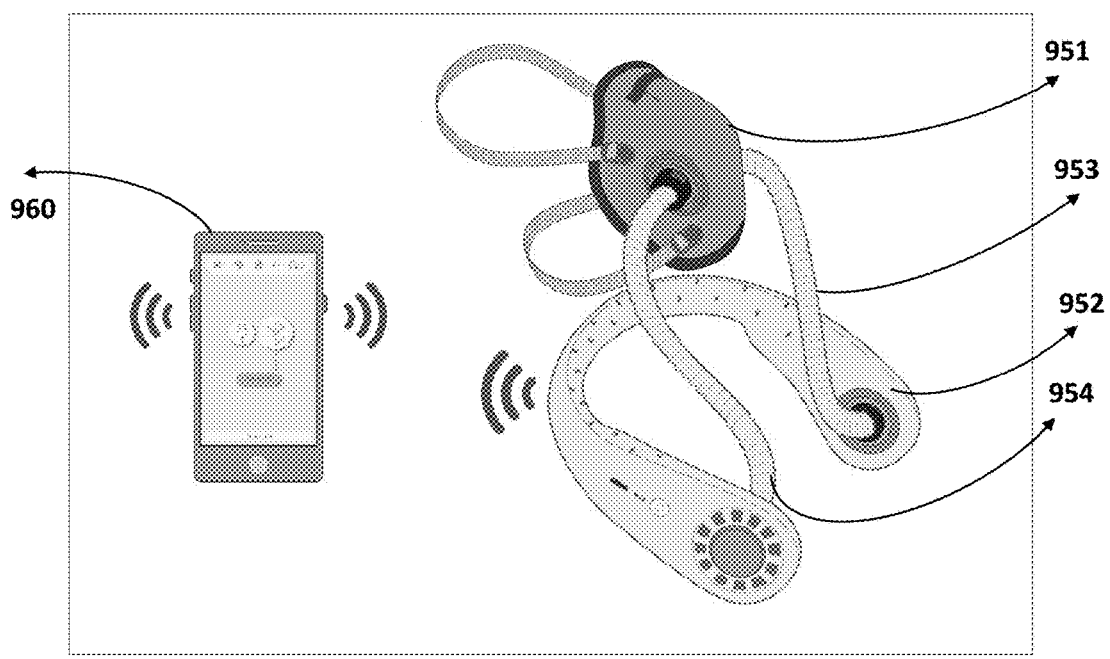
FIG. 6I depicts connection of the respirator with a face mask and a wearable device to an external device using wireless transceiver.

FIG. 6I depicts communication of respirator 950/1900 with an external device using a wireless transceiver. The wireless transceiver can be WiFi (wireless fidelity), Bluetooth, Zigbee, Infrared, 5G, 6G, and beyond 5G/6G. Respirator 950/1900 can act as an IoT (Internet of things) device and uses 5G, 6G, or beyond 5G/6G to communicate with another device through IoT network (5G, 6G, or beyond 5G/6G). In both methods (FIGS. 6H and 6I) the external device is used for diagnostic, alarm, control, status, software download, and configuration.

Figure 6J:
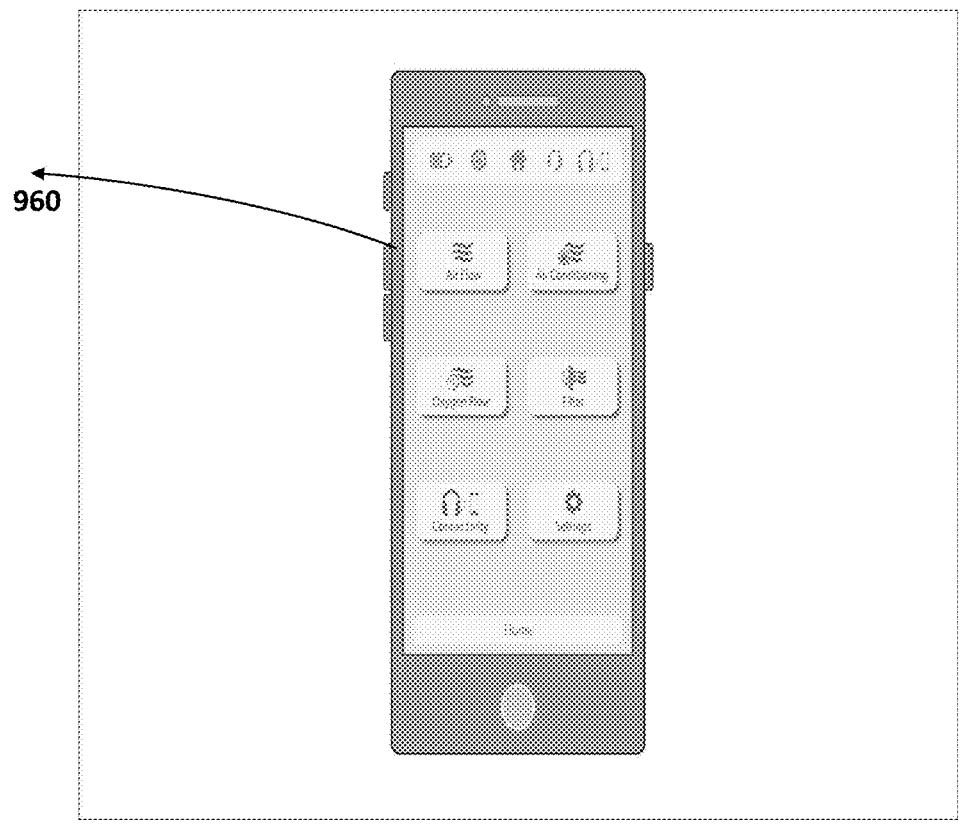
FIG. 6J shows the home page of an application on the external device's screen.

FIG. 6J shows the home page of an application used by an external device to perform configuration settings, observe the status of the operation of respirator 950/1900, perform diagnostics, and receive alarm due to any failure or malfunction.

Figure 6K:
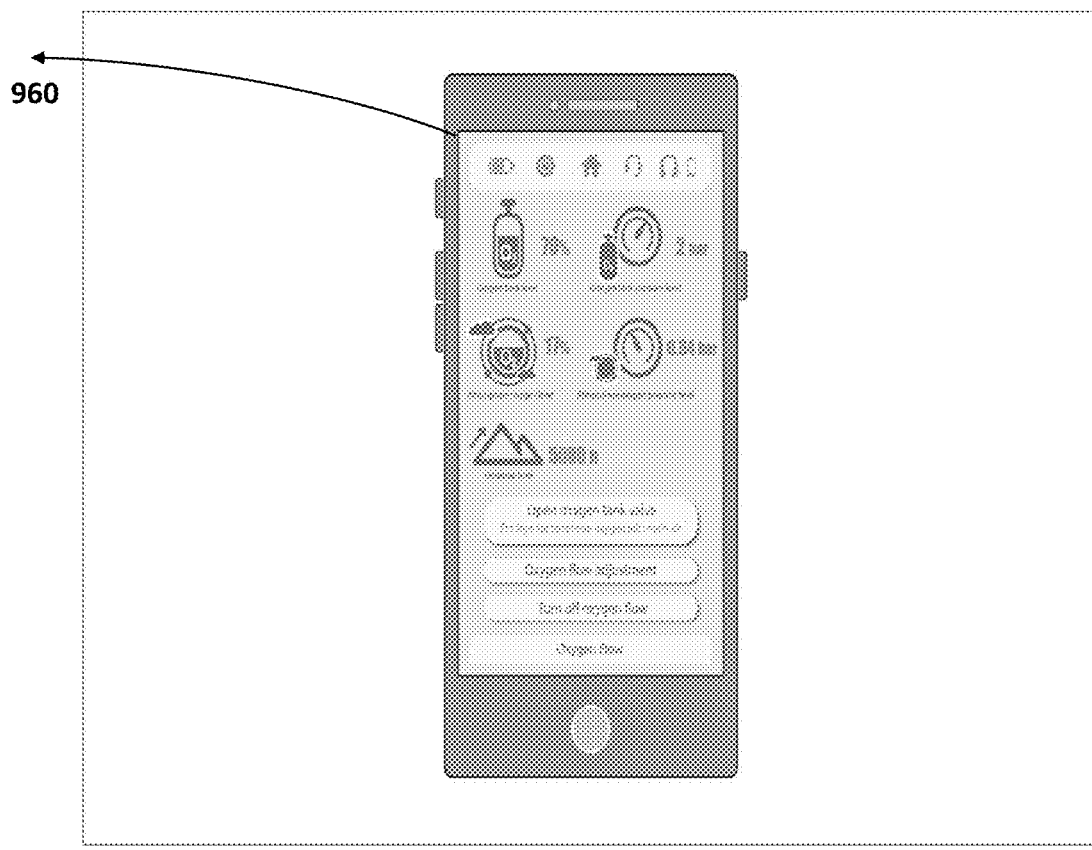
FIG. 6K illustrates the page of the application which shows the status of oxygen tank.

FIG. 6K depicts a page of the application which shows the status of the oxygen tank. It can show the amount of oxygen used, the amount of oxygen left, elevation level, atmosphere oxygen level, atmosphere pressure level, tank oxygen pressure level, and other information and instructions.

Figure 7:
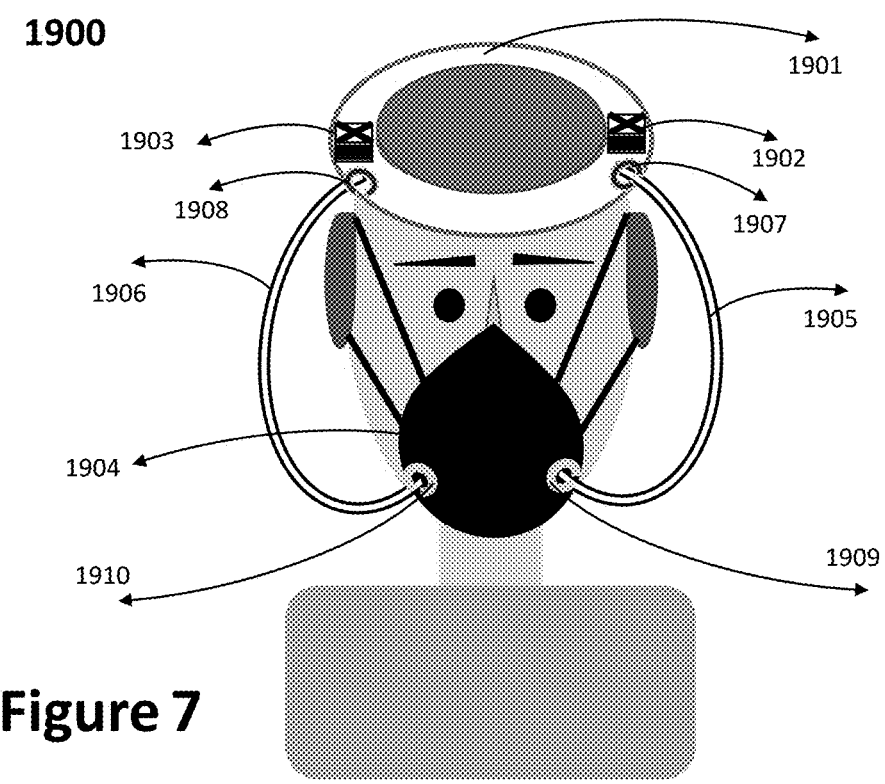
FIG. 7 illustrates a respirator with a face mask and a wearable device that is a head ring.

FIG. 7 depicts a novel respirator 1900. The respirator comprises of a wearable device (head ring) 1901, a typical face mask 1904, an air pipe (tube) 1905 that receives air from wearable device (head ring) 1901 using inlet assembly sucking fan 1902 and inject it into the interior of the face mask 1904, and an air pipe (tube) 1906 that receives contaminated air from interior of face mask 1904 and delivers it into wearable device (head ring) 1901. Air pipes (tubes) 1905 and 1906 are attached to the face mask 1904 through connectors 1909 and 1910. Fresh air is sucked from free space by wearable device (head ring) 1901 using inlet assembly sucking fan 1902 (which has a HEPA, a ULPA filter, or a proprietary filter attached to it) and delivered to the interior of the face mask 1904 using the air pipe (tube) 1905 that is connected to both wearable device (head ring) 1901 and face mask 1904. Contaminated air from interior of face mask 1904 is received by air pipe (tube) 1906 that is connected to both face mask 1904 and wearable device (head ring) 1901 and delivered into wearable device (head ring) 1901 to be sucked by fan 1903 (which has a HEPA, a ULPA filter, or a proprietary filter attached to it) and released to free space. The air pipes (tubes) 1905 and 1906 may be part of wearable device (head ring) 1901 or face mask 1904.

i) In one embodiment, the wearable device (head ring) 1901 is also used as a neck and/or face cooler by blowing some of the air it sucks (pulls in) by fan 1902 from free space towards the face and neck.

j) In one embodiment, wearable device (head ring) 1901 is used as a neck and/or face cooler by blowing the filtered contaminated air sucked (pull out) by fan 1903 from the interior of the face mask 1904 towards the neck and face.

k) In one embodiment, wearable device (head ring) 1901 is used as a neck and/or face cooler by blowing some of the filtered sucked (pulled in) air by fan 1902 from environment and the filtered contaminated air sucked by fan 1903 from the interior of the face mask 1904 towards the neck and/or face using air apertures or opening holes on the peripheral of wearable device (head ring) 1901.

l) In another embodiment, the air flow from the air aperture or opening hole is controlled by changing the area of opening of the aperture or hole.

m) In another embodiment, wearable device (head ring) 1901 sucks the air from free space using fan 1902 and sends it into the interior of the face mask 1904 without filtering.

n) In one embodiment, wearable device (head ring) 1901 sucks (pulls in) the air from free space using fan 1902 and sends it into the interior of the face mask 1904 after being filtered.

o) In another embodiment, wearable device (head ring) 1901 sucks (pulls in) the air from free space using fan 1902 and sends some of it into the interior of the face mask 1904 after being filtered and blows the remaining of the sucked air from free space filtered or unfiltered towards the neck and/or face for cooling.

p) In one embodiment, air pipes (tubes) 1905 and 1906 are part of wearable device (head ring) 1901 and can be slid inside the wearable device (head ring) 1901 when not connected to the face mask 1904.

q) In one embodiment, air pipes (tubes) 1905 and 1906 are independent components and are connected to both face mask 1904 (through connectors 1909 and 1910) and wearable device (head ring) 1901 (through connectors 1907 and 1908) using various simple methods that prevent any air leak.

r) In another embodiment, the amount of air that is passed through face mask 1904 is controlled by various known practical methods such as speed of fan, the amount of sucked air that is used for cooling, releasing extra air, etc.

s) In another embodiment, the amount of air used by wearable device (head ring) 1901 for cooling the neck and/or face is controlled by various known practical methods such as opening and closing the apertures or holes that blow the air, reducing the opening of the apertures or holes, reducing fan speed, etc.

t) In one embodiment, the amount of sucked air from free space (environment) by fan 1902 and contaminated air from interior of face mask 1904 by fan 1903 is controlled and adjusted through various known practical methods such as changing the DC voltage applied to the fans.

u) In another embodiment, wearable device (head ring) 1901 uses fan 1903 to suck the contaminated air from interior of face mask 1904 through air pipe 1906 as well as some air from free space to use for cooling the neck and/or face through apertures or opening holes on the peripheral of wearable device (head ring) 1901.

v) In one embodiment, wearable device (head ring) 1901 stores oxygen inside wearable device (head ring) 1901 and through an injection valve sends oxygen into inlet assembly to be mixed with filtered or unfiltered air sucked from free space by fan 1902 before releasing the mixed air and oxygen through air pipe 1905 into face mask 1904.

w) In another embodiment, the amount of oxygen that mixes with sucked and filtered or unfiltered air from free space is controlled for different applications.

x) In one embodiment, respirator 1900 with wearable device (head ring) 1901 is used for various applications when body needs air with required oxygen level. These applications are people with asthma, high elevation hikers, hospital patients, nurses, doctors, miners, gliders, people with breathing problem, people with heart problem, people with medical problems that need higher level oxygen, skiers at high elevations, ordinary people in areas with high level of air pollution (cities), fire fighters, tourist in high elevation places, factory workers, carpenters, chemical lab workers, airplane passengers, and any other application that requires a respirator.

Figure 8A:
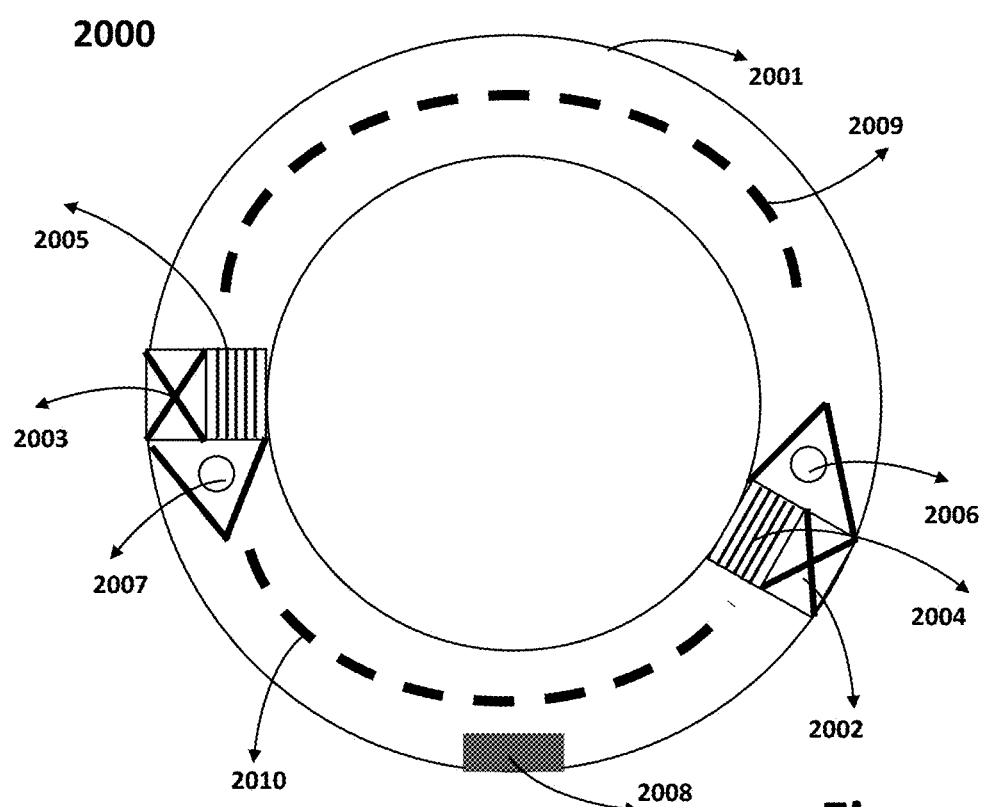
FIG. 8A depicts a wearable device (a head ring) that supplies air to the face mask.

FIG. 8A shows a detailed wearable device (head ring) 2000 which is used in FIG. 7 as wearable device (head ring) 1901. Wearable device (head ring) 2000 uses a fan 2002 to suck (pull in) the air from environment, filter it with filter 2004 and send it from outlet 2006 into interior of face mask 1904 through air pipe (tube) 1905. The contaminated air from interior of face mask 1904 is sucked by the fan 2003 through the air pipe 1906 and the inlet 2007, filtered by the filter 2005 and released to the environment by the fan 2003.

Figure 8B:
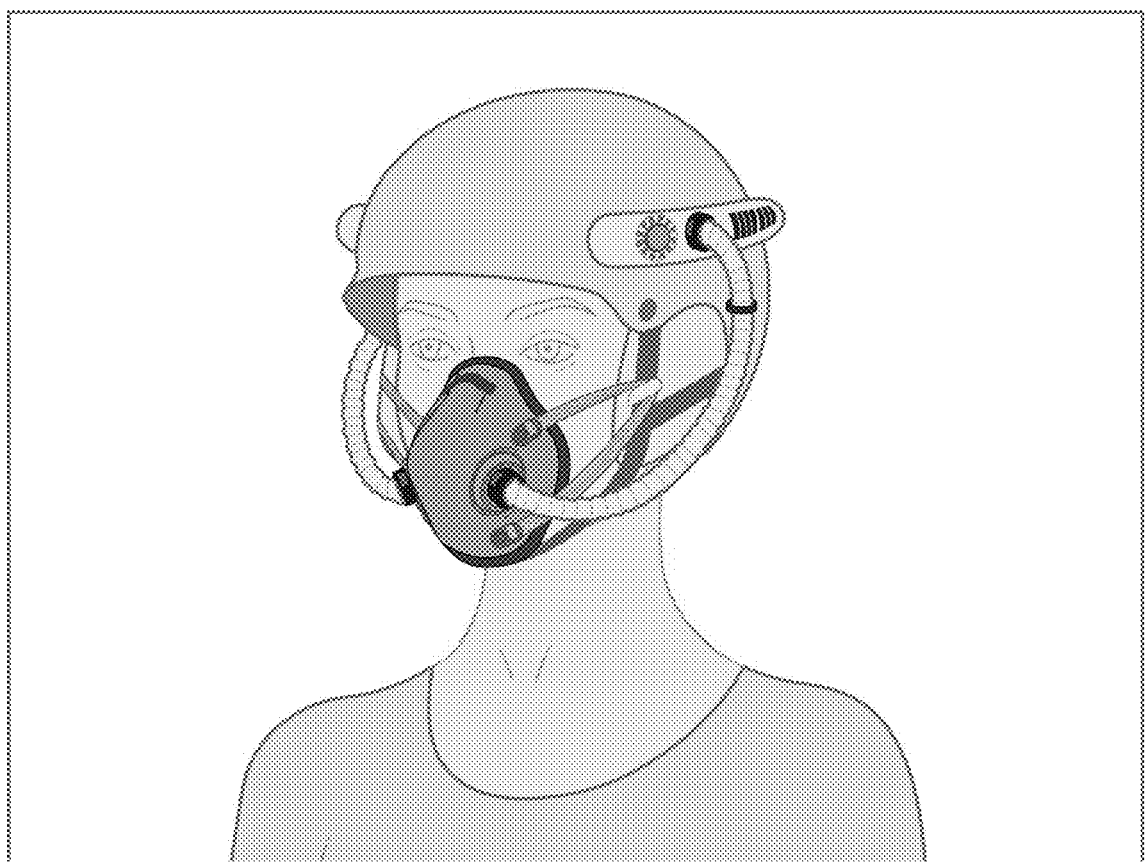
FIG. 8B illustrates a wearable device (a head ring) attached to a helmet.

FIG. 8B shows how wearable device (head ring) 2000 is connected to a helmet. Helmets have different shapes and structures. The head ring when is connected to a helmet can be in one piece or two pieces. Wearable device (head ring) 2000 does not need to be a complete ring. When it has one piece only it can have an arc shape. When it has two pieces each piece can have an arc shape. For attaching the head ring to a helmet one can use Velcro fasteners and any other methods or means of fastening that are not permanent and after use readily can be detached and reused. The wearable device 2000 can also be an integral part of the helmet. A helmet itself can be wearable device 2000.

Wearable device (head ring) 2000, among other things includes a flexible tube (solid) 2001, inlet assembly with fan 2002 and filter 2004, an exhaust assembly with fan 2003, and filter 2005, battery and control circuit housing 2008, apertures 2009 and 2010, outlet 2006 and inlet 2007.

The flexible tube 2001 can be solid or hollow depending on the application of wearable device (head ring) 2000. The flexible tube 2001 is made of very light materials to keep the overall weight of wearable device (head ring) 2000 low. The battery and control circuit housing 2008 accommodates the battery that powers the fans 2002, 2003, and a control circuit with a CPU that controls the operation of the respirator 1900. The outlet 2006 and inlet 2007 have circular (square, or other) cross sections and provide necessary requirements to connect to air pipes 2005 and 2006 without any leakage of air. Tube 2001 can have a key on its external surface for turning on and off the operation of wearable device (head ring) 2000. The wearable device (head ring) 2000 can also have a reset bottom on the external surface of tube 2001 to reset the control circuit.

Fans 2002 and 2003 suck air from environment and interior of the face mask 2904 respectively and their sucking power is adjusted independently by controlling the DC voltage apply to them from the battery and control circuit in housing 2008. Filters 2004 and 2005 both are either high efficiency particulate air (HEPA) filters, ultra-low particulate air (ULPA) filters, or a proprietary filter based on the application of the head ring 1901. The same filtering options explained earlier for wearable device 1200 can also be used for respirator 1900.

Wearable device (head ring) 2000 in addition to facilitating flow of fresh and filtered air inside the face mask performs cooling of the neck and face by blowing air towards the neck and face. The air sucked by fan 2002 is filtered by filter 2004 before sending portion of filtered air into the interior of face mask 1904 from outlet 2006 through air pipe 1905 and blowing the remaining of the air through apertures or holes 2009 and 2010 towards the neck and face. The speed of the air flow from the apertures 2009 and 2010 can be adjusted by reducing the opening of the apertures or by totally closing selected number of apertures 2009 and 2010.

Contaminated air from interior of face mask 1904 is sucked by fan 2003 through inlet 2007 and air pipe 1906, filtered by filter 2005, then sent to the aperture 2009 or 2010 for blowing towards the neck and face. Fan 2003 in addition to the contaminated air it sucks from interior of the face mask through air pipe 1906 and inlet 2007 it can also suck air from environment through a separate inlet on the tube 2001 to increase the amount of air that is blown towards neck and face through apertures 2009 and 2010.

Wearable device (head ring) 2000 can also be an oxygen tank for oxygen. Wearable device (head ring) 2000 facilitates flow of fresh and filtered air that is mixed with oxygen from the oxygen tank inside the tube 2001. The air sucked by fan 2002 from the environment is filtered by filter 2004 and mixed with injected oxygen before sending it into the interior of face mask 1904 from outlet 2006 and through air pipe 1905 like wearable device (neck hanger) 1200.

Wearable device (head ring) 2000 also like wearable device (neck hanger) 1200 can use a regulator. The regulator consists of a pressure reducer and a flow adjuster. The oxygen tank can be a tank within the tube 2001. The entire wearable device (neck hanger) 2000 or a portion of it can be used as oxygen tank. It all depends on several parameters which are safety issues, weight, pressure of compressed oxygen (in any form, gas, solid or liquid), and complexity. The regulator should also function as a pressure gauge and a flow meter. One way of providing these two functions is to use sensors, one as pressure sensor and another as flow sensor. The other approach is to have provisions for a pressure gauge and a flow meter to be connected to the regulator when needed like a valve that is used to refill the oxygen tank.

The speed of the fans is controlled by the control circuit by changing the DC (direct current) voltage applied to the sucking fans 2002 and 2003. The power and control circuit housing for battery and control circuit can have a USB port or other power ports for charging the battery. The USB port is also used for communication between the control circuit and an external device. The control circuit can also use a wireless transceiver like Bluetooth, Zigbee, Infrared, or WiFi (wireless fidelity) to communicate with external devices.

The control circuit within the power and control circuit housing performs several tasks. One of the tasks is to control the speed of the fans by changing the DC voltage applied to the fans. The control circuit based on the information it obtains from various sensors and external networks and devices decides what voltage to apply to the sucking fan 2002 and 2003. The decision is made by an artificial intelligence (AI) algorithm that is executed in the control circuit's CPU (central processing unit). A second task is to monitor the amount of charge of the batteries through appropriate sensors and use an LED (light emission diode) which is capable of deeming, a red LED when the charge is below a threshold and a green light when fully charged. It can also communicate to an external device like smart phone the amount of available charge. A third task is to monitor the pressure of oxygen tank and estimate the amount of oxygen in the tank and to indicate when the tank needs to be refilled through a red LED or communicating with an external device. A fourth task is to act as a flow meter for the regulator. If the oxygen flow is below a threshold, the control circuit indicates through an LED or communicates to an external device. A fifth task is to connect to an external device and configure respirator 1900. The configurations parameters are initial operating parameters of the respirator that include various thresholds, and settings. Another task of the control circuit is to perform diagnostic and alarms.

Figure 9A:
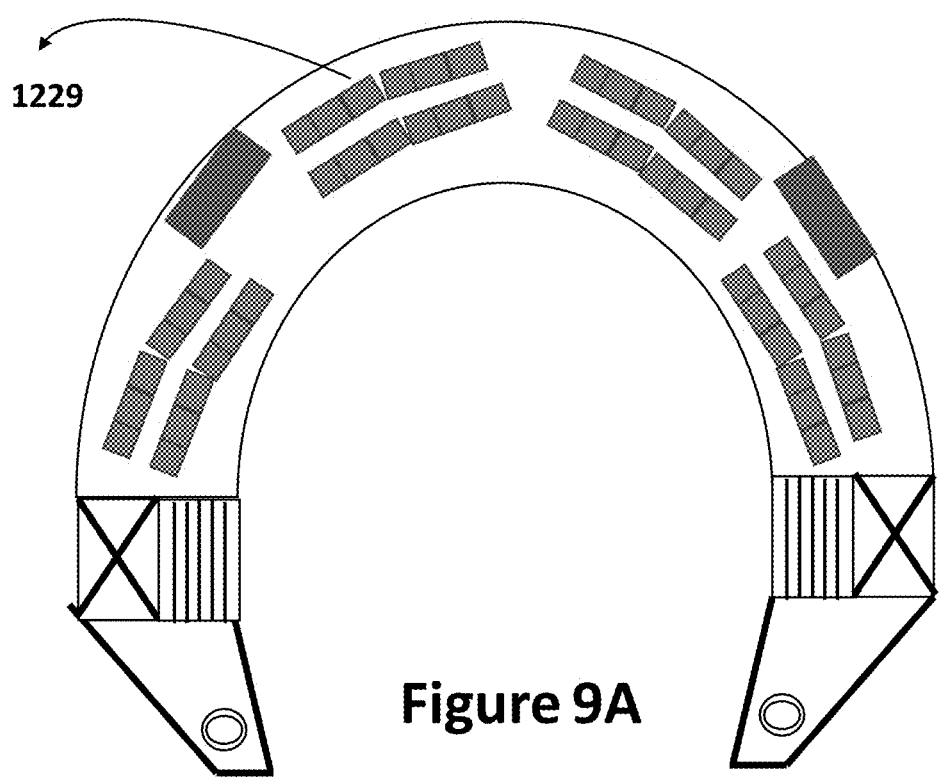
FIG. 9A shows a wearable device with locations of solar panel.
Figure 9B:
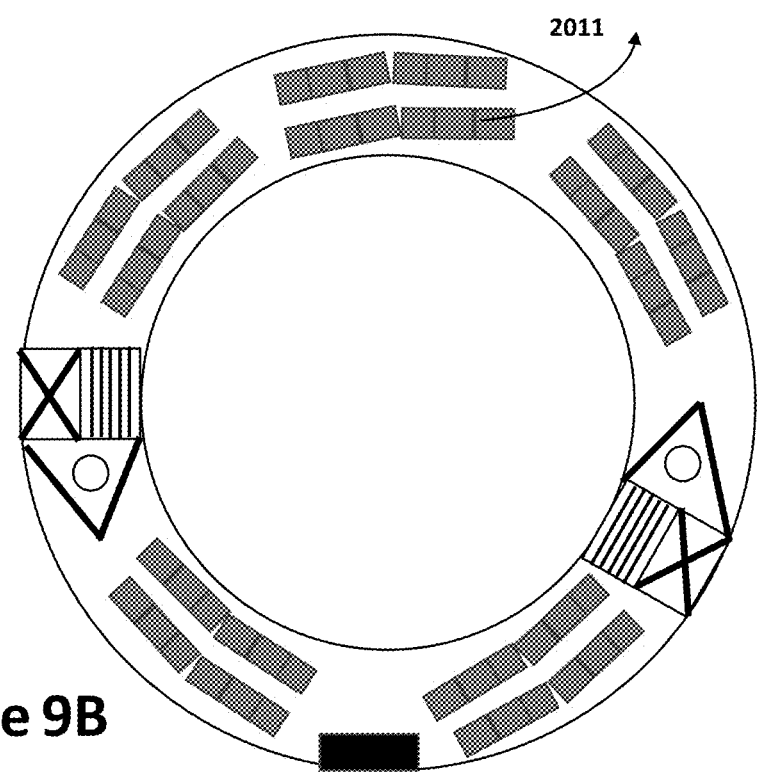
FIG. 9B shows a head ring (wearable device) with solar panel.
Figure 9C:
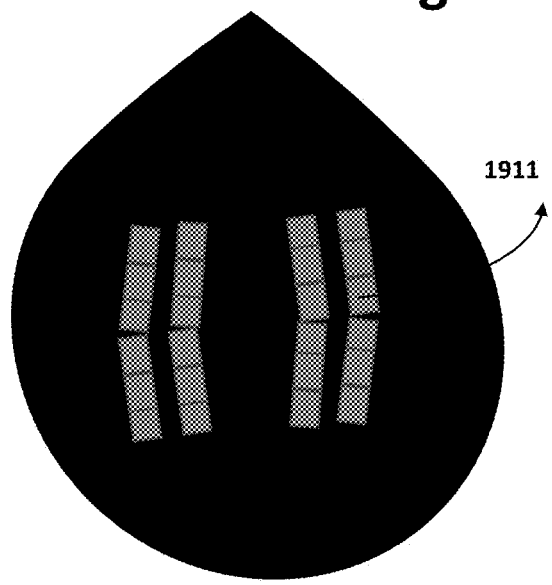
FIG. 9C depicts a face mask with solar panel.

As mentioned before the rechargeable battery can be fully or partially charged through solar cells. The solar cells 1911 may be attached to the external of the face mask as shown in FIG. 9C. The solar cells 1229 and 2011 are attached to the external peripheral of wearable device (neck hanger) 1200 and wearable device (head ring) 2000 as shown in FIG. 9A and FIG. 9B. In the power and control circuit housing there is a DC (Direct Current) converter circuit to convert solar energy to the DC voltage required for charging the battery.

Sensors are located at various locations of respirators 950 and 1900 (both face mask and wearable device that has various form factor as described in earlier paragraphs) to provide operation information data, measurement information data, and metering information data for the control circuit located in the battery and control circuit housing. Control circuit has a CPU (central processing unit) that receives all information data and uses its artificial intelligence algorithm to monitor operation of respirator 950 or 1900 in real time and control or modify operation of various components and alert the person wearing them if a deficiency, a problem, or a mal function detected. Control circuit can use LED to show proper function, or mal function of various components. The control circuit also uses a wireless transceiver or a USB port to send status and real time value of certain parameters to an external device like a computer, a tablet, a smart phone (directly or via 5G/6G network) to display numerically or graphically and being analyzed.

The sensors are attached at various locations of respirator 950 and 1900. These location are inside of the face mask for air flow, outside of the face mask for solar panel and air pressure, inside of both air pipes (tubes), before air filters that are attached to both sucking fans, after the air filters to make sure filters function correctly and are not blocked, various location inside and outside peripheral of wearable device (head ring) 2000, and wearable device (neck hanger) 1200 for air flow and solar panels, inside the oxygen tank within wearable devices (head ring) 2000, and (neck hanger) 1200 for pressure measurement, inside oxygen tank regulator and inside of power and control circuit housing for monitoring battery power (charge, and other parameters). It is also possible to have sensors at other locations for other purposes (pollution measurement) like measuring the altitude (elevation) of the area where the respirator is used from sea level. Elevation helps to measure the atmospheric pressure which results in calculating the oxygen level in the atmosphere air. The information data that sensors measure or collect are sent to the control circuit's CPU to be used by AI algorithm for analysis.

The sensors do not need to be on continuously. To save power, the sensors are turned on during a time window configured in the control circuit, collect the required information data, and then turned off. This can be done during a time window every 10 seconds or other configurations that are suitable for a particular application.

Respirators 950 and 1900 act like an Internet of Thing (IoT) device. It can communicate with external devices and networks. Since both respirator 950 and 1900 have operating fan, to make the battery last longer it is always possible to use an external auxiliary battery attached to waist or arm to support required power for both fans and control circuit wireless transceiver that provides the function of IoT device and communicate real time or as needed with external devices or networks. The auxiliary battery is connected to respirator 950 and 1900 with a power cord through a USB power port or any other power port.

Respirators 950 and 1900 as IoT devices communicate with other IoT devices like smart phone, computers, and tablets through IoT networks that are fifth generation (5G) wireless network, sixth generation (6G) wireless network, beyond 5G/6G wireless network or Wireless Fidelity (WiFi) network.

Respirators 950 and 1900 as IoT devices through external devices (using Bluetooth, Zigbee, WiFi and infrared) as well as external devices that are attached to IoT networks can be configured, diagnosed, monitored, and updated with new software for the control circuit's CPU. The analysis data from AI algorithm can be shared with external devices (through Bluetooth, Zigbee, WiFi and infrared) or devices that are attached to IoT network for monitoring as well as modifying the configuration parameters. The control circuit CPU can also send the raw data collected by various sensors to an external device the way that was explained above for analysis and decision making. The external device based on analysis of raw data decides whether there is a need for the modification of the operating parameters of respirators 950 and 1900 and through IoT network or using Bluetooth, Zigbee, Infrared, or WiFi performs the changing of the operation parameters.

In both cases of respirators 950 and 1900 the face masks 951 and 1904 are attached to the face of the person and cover the nose and the mouth of the person. Face masks 951 and 1904 are not attached to the nose and mouth of the person and there is a gap between the nose and mouth with the interior surface of the mask to allow for air flow within the interior of the mask. However, the peripheral of the face masks 951 and 1904 are attached to the face to prevent any air from entering the interior of the mask and any interior air of the mask to leave the mask through peripheral of the face mask.

Face masks 951 and 1904 use ear loops to attach to the face of a person. For even better attachment it is possible to loop the left ear loop and the right ear loop and connect them together with a paperclip at the back of the head. Another technique for attaching the face mask to the face of the person is to attach the left ear loop to a strap and the right ear loop to another strap and fasten the two straps at the back of the head using hook and loop fastener made up of two pieces of materials: one with lots of tiny loops and another with lots of tiny hooks. Therefore, one of the straps acts as hook and the other strap acts as loop. The mask can also be attached to the face by any other feasible means that is obvious to a person with skill of fastening.

Obstructive sleep apnea (OSA) is a disorder where narrowing of upper airway leads to disturbance in normal ventilation during sleep. Decreased airflow due to repetitive complete or partial obstruction of the upper airway occurs with consequent progressive respiratory effort to overcome the obstruction. These obstructive respiratory events are typically associated with cortical microarousals leading to sleep fragmentation and consequent unrefreshing mornings. Sleep is a restorative phenomenon for the body. Instead in OSA patients, sleep becomes a stressful ordeal, the effect of which is borne by the patient not only in sleeping hours but also in the subsequent daytime hours in various ways. OSA has had its struggle with lack of awareness, significant expense of diagnosis and treatment and concerning bodily consequences. Awareness for this disease is still emerging, both amongst patient population and medical care givers across the world. In the current scenario, the world has gathered enough literature to support a better understanding regarding disease physiology, consequences, accompaniments and effects on overall morbidity and mortality.

Diagnosis of OSA comprises of a suggestive history, positive examination findings and confirmatory overnight polysomnography (PSG). In history, one should look for duration of symptoms, possible identifiable triggers like drugs and underlying medical disorders which should be addressed at priority. Also, an attempt to rule out mimics should be done. For example, sleep deprivation may be caused due to anxiety, depression disorder, diabetes, pain, prostatic symptoms, neuro stimulant drugs leading to excessive daytime sleepiness. Similarly, snoring can be due to pregnancy, nasal obstruction, or congestion than by OSA. Usually, supervised laboratory-based sleep study is the standard of practice for confident diagnosis of OSA in all scenarios. However, in resource limited settings or where there is strong likelihood of OSA and laboratory study is not feasible, home sleep analysis can be performed. There has been a strong recommendation that clinical tools, questionnaires and prediction algorithms should not be used to diagnose OSA in adults, in absence of polysomnographic or home sleep apnea testing (HSAT). Detailed polysomnographic features have been discussed in Sleep Study Interpretation in OSA. Other supportive tests which can be helpful are sleep endoscopy, actigraphy and sleep diary. Sleep endoscopy has a role in diagnosis where dynamic collapse of upper airway is visualized under endoscopic guidance. Actigraphy is a noninvasive modality to gauge body movements, which should be cautiously used in OSA diagnosis. Sleep diary maintenance is another helpful adjunct in diagnosis, which should be used as supportive test only.

In this application a novel and simple method based on airflow measurement to diagnose OSA is disclosed. This solution uses one of the wearable devices shown in FIG. 2, 4A, 4C, 4E, 4G, 4K, or 4M in conjunction with a face mask that is connected to wearable device by two air tubes. To measure the airflow an airflow sensor (meter) that is installed in the path of the airflow is used. One or multiple airflow sensors (meters) can be used at different locations to measure and collect airflow real time data for analysis and diagnoses of OSA. In the following paragraphs the details of OSA detection and mitigation are explained.

FIG. 10 shows the possible location of an airflow sensor (meter) for better measurement of airflow in real time. FIG. 10 like FIG. 5 shows flexible air pipe (tube) 953/954 in drawing "a" and outlet or inlet of inlet assembly and exhaust assembly of wearable device (neck hanger) 952/1200/1000 in drawing "b". Flexible air pipe (tube) 953/954 comprises of air pipe (tube) 1301 and female heads 1302 and 1303. Female heads 1302 and 1303 are used to connect the flexible pipe (tube) 953/954 to face mask 951/1904 and wearable device (neck hanger) 952/1200/1000. Wearable device (neck hanger) 952/1200/1000 has the male head 1304 for the female head 1302 of air pipe (tube) 1301.

The airflow sensors can be installed anywhere along the air tubes 953/954. Since the air tubes 953/954 are flexible the best location for installing airflow sensors 1305 and 1306 is close to each end of the air tubes 953/954 in the vicinity of the female heads 1302 and 1303. As explained earlier air tubes 953/954 can also use male head. Airflow sensors are located in the airflow path of the sleep apnea device where air is flowing depending on real time airflow measurement requirement for the control circuit.

Airflow sensors can also be installed at the outlet head 1304 of the inlet assembly and inlet head 1304 of the exhaust assembly of wearable device (neck hanger) 952/1200/1000. The airflow sensor (meter) 1307 is installed in the vicinity of inlet head and/or outlet head that can be male or female. Therefore, there are four locations at both ends of the air tubes 953/954 for installation of the airflow sensors and two locations at vicinity of the outlet of the inlet assembly and inlet of exhaust assembly. Airflow sensors (1305, 1306, and 1307) can also be installed at any other location of airflow. It is also possible to use more airflow sensors in the path of airflow.

Figure 11A:
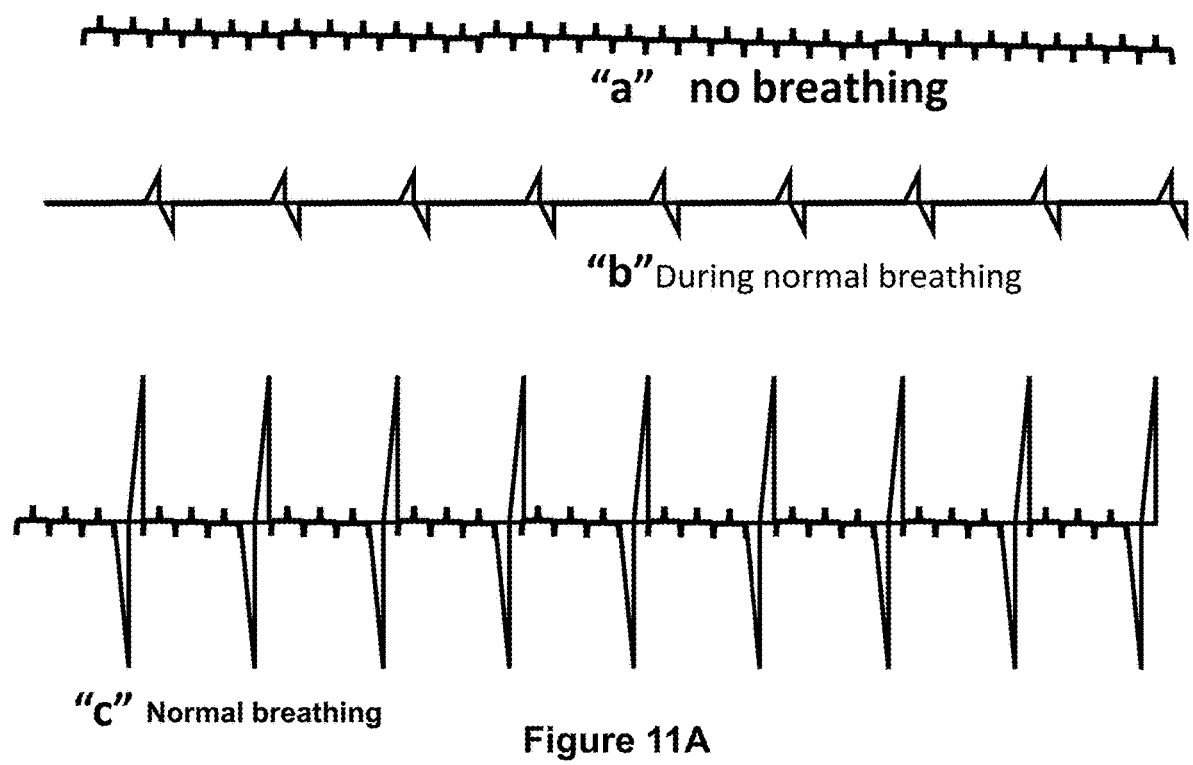
FIG. 11A shows the airflow in presence and absence of inhaling and exhaling.

FIG. 11A shows the real time airflow at the outlet of the inlet assembly or inlet of the air tube 953 and outlet of air tube 954 and inlet of the exhaust assembly. Airflow "a" is at all six locations mentioned above when the person wearing the face mask is not inhaling and exhaling. The airflow is steady and smooth with some random variation due to the movement of the person who uses sleep apnea device and fluctuation in operation of the moving components of the inlet assembly and exhaust assembly. Airflow "b" is at the outlet of the inlet assembly and inlet and outlet of the air tube 953 that connects the inlet assembly to the face mask when the person wearing the face mask is inhaling and exhaling normally. Airflow "c" is at the inlet of the exhaust assembly and inlet and outlet of the air tube 954 that connects the exhaust assembly to the face mask when the person wearing the face mask is inhaling and exhaling normally. Airflow "b" and "c" are magnified for clarity.

The reason for the real time shape of airflow "b" is that during the inhale time window or period the speed of airflow in the outlet of inlet assembly and inlet and outlet of air tube 953 increases and then decreases during the exhale time window or period. The increase is because during the inhalation process the air is further pulled from inlet assembly and the reason for decrease during exhalation process is that the air is further pushed towards the inlet assembly. From airflow "b" and "c" the trajectory or airflow in "b" is opposite of airflow "c".

FIG. 11B shows the real time airflow at the outlet of the inlet assembly or inlet of the air tube 953 and outlet of air tube 954 and inlet of the exhaust assembly when sleep apnea occurs. Airflow "d" is at the inlet of the exhaust assembly and inlet and outlet of the air tube 954 that connects the exhaust assembly to the face mask when the person wearing the face mask experiences sleep apnea during inhaling and exhaling. Sleep apnea occurs when normal breathing is disrupted due to narrowing of upper airway that leads to disturbance in normal ventilation during sleep for ten seconds or more. Airflow "e" is at the outlet of the inlet assembly and inlet and outlet of the air tube 953 that connects the inlet assembly to the face mask when the person wearing the face mask experiences sleep apnea during inhaling and exhaling. Airflow "d" and "e" are magnified for clarity.

The airflow sensors that are located at the inlet of exhaust assembly or inlet and outlet of the air tube 954 real time measure the airflow and send the data to control circuit for analysis. If needed control circuit uses the real time measured airflow data from the airflow sensors of air tube 953 and outlet of inlet assembly. In addition to real time airflow data from exhaust assembly and air tube 954/953 the control circuit can also use (wired or wireless) real time data from biometric devices like oxygen saturation, heart rate variation HRV or electrocardiogram (ECG, EKG) connected to the person's body for analysis. The real time data is used by an artificial intelligence (AI) algorithm that is executed in a central processing unit (CPU) that resides in the control circuit to detect sleep apnea occurrence, duration of apnea and number of apneas in a defined time window. Although the airflow "d" provides sufficient real time data for the AI algorithm to detect apnea, having access to the real time data from other sensors and biometric devices mentioned above helps to minimize false detection. In the following paragraphs various implementation and options for detection and mitigation are described.

To perform home sleep apnea testing (HSAT), or lab sleep apnea testing (LSAT) to detect apnea using the method or solution described above there is a need for a pillow that houses or has all or some of the components of the wearable device 952/1200/1000 embedded in it. The pillow can have various shapes and perform exactly like a typical pillow used during sleep. It provides comfort for the neck, shoulders, and head. It is also possible to hold the head steady if needed and act like a hat. It can be like travel pillows used during flying or a jacket that has short sleeves with a neck pillow. Therefore, in the following paragraphs all types of pillows, hat and pillow combined with any shape is called pillow. All or selected components of wearable device 952/1200/1000 are embedded in the pillow.

Figure 12A:
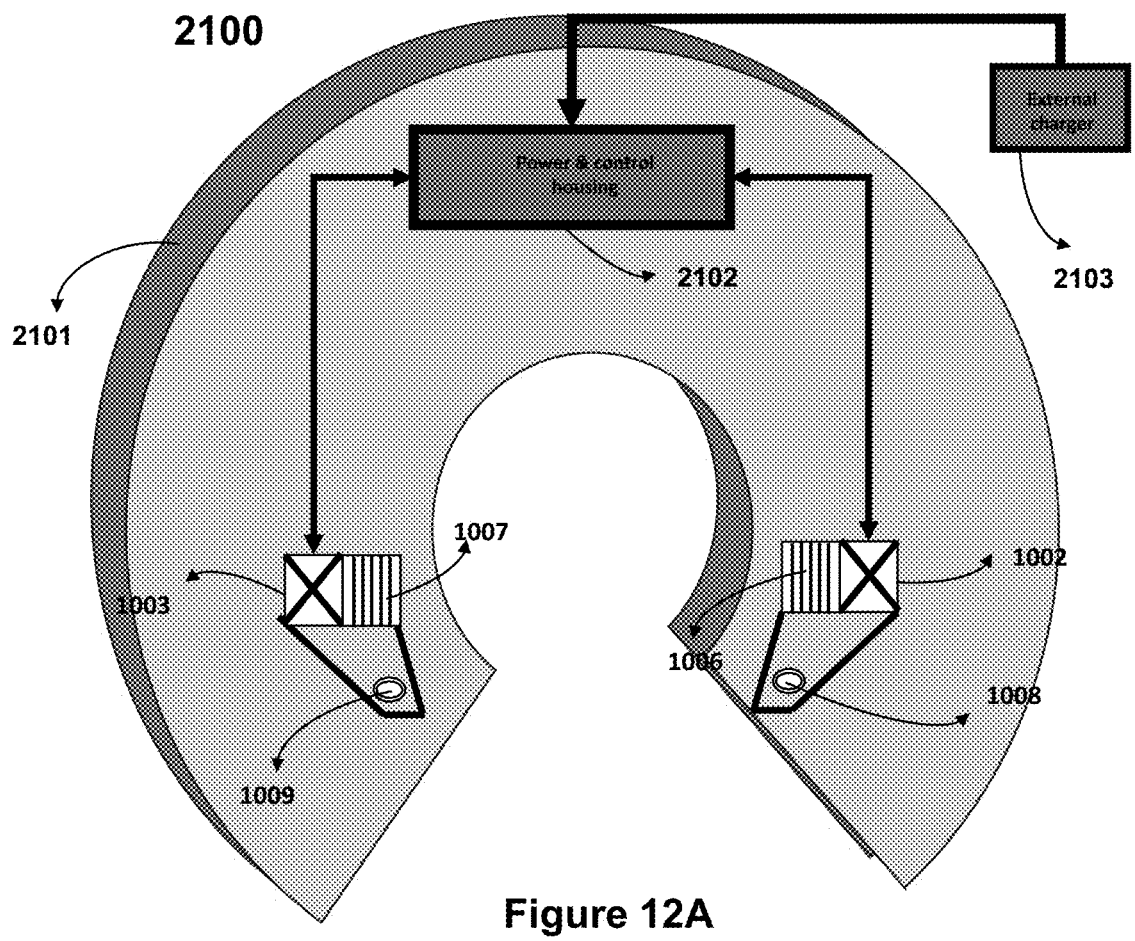
FIG. 12A shows a pillow with an embedded inlet assembly, exhaust assembly, and a power housing.

FIG. 12A shows sleep apnea detection 2100 with pillow 2101 that holds only inlet assembly and exhaust assembly of the wearable device 952/1200/1000. The air tubes 953/954 and face mask 951/1904 are not shown in the sleep apnea detection 2100 for simplicity. The design of pillow 2021 is not the subject of this application. Within pillow 2101 there is one or more air passageways used to pull air from the environment by air inlet assembly (1002, 1006, 1008) and to release air to the environment by exhaust assembly (1003, 1007, 1009). These environmental air passageways are at locations in pillow 2101 that do not cause discomfort for the person using pillow 2101 and are not totally blocked by movement of the person during sleep. The air passageways used by exhaust assembly if needed can be at locations where air is not blown towards the head, neck or face of the person using the pillow. For air inlet assembly outlet 1008/1208 and exhaust assembly inlet 1009/1209, pillow 2101 has two specific passageways (outlet and inlet). The air tubes 953 and 954 are connected to inlet assembly and exhaust assembly through these specific passageways. The method and implementation of the connection of air tubes 953 and 954 are not the subject of this application. The connections need to be implemented in a way that does not cause discomfort for the person using pillow 2101 and is without any leakage. The air inlet assembly and air exhaust assembly inside the pillow need to be mechanically stable to avoid air flow fluctuation through air tubes 953/954 and the face mask 951/1904.

Powerhouse 2102 inside pillow 2101 houses the control circuit and battery. The battery is charged by charger 2103 when needed to power all the moving components, reshaping components, electronic circuits and all the sensors or charger 2103 directly powers the control circuit and all other moving components, reshaping components, and sensors.

Figure 12B:
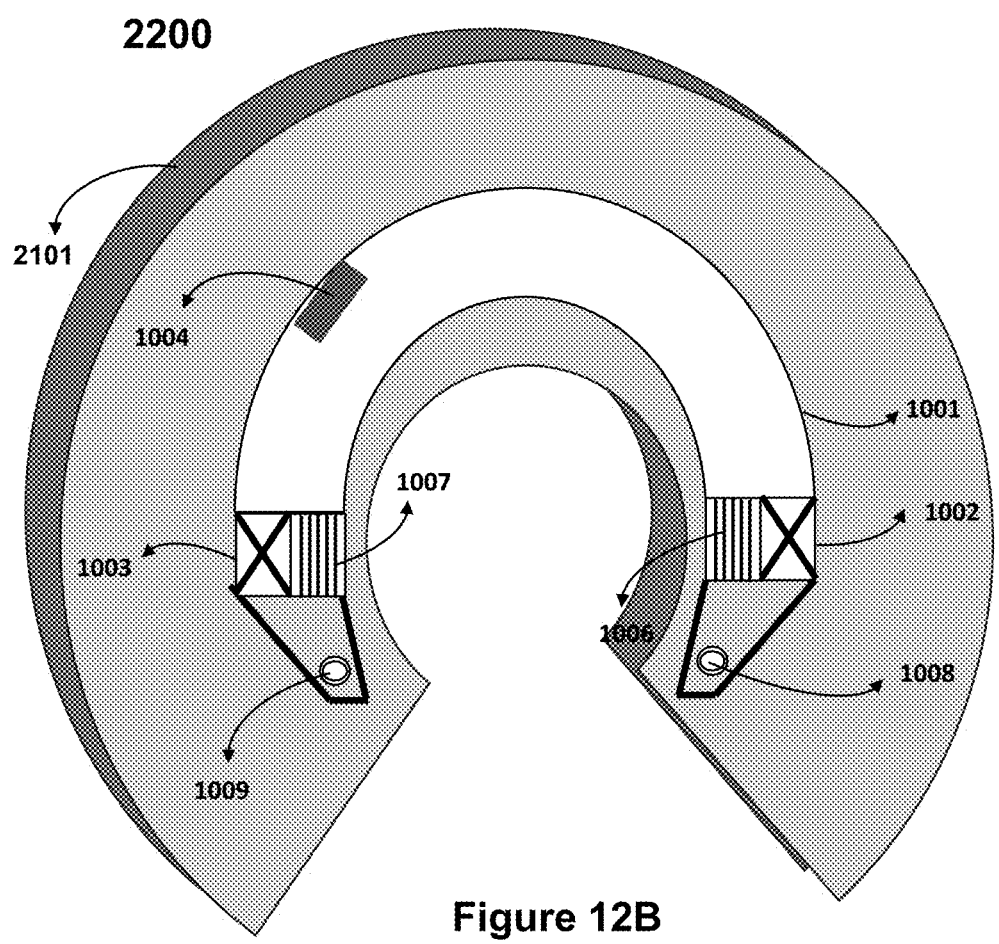
FIG. 12B illustrates a pillow with an embedded inlet assembly, and exhaust assembly connected by a tube that houses battery and control circuit.

FIG. 12B illustrates sleep apnea detection 2200 with pillow 2101. The difference between solution 2100 and 2200 is the hollow or solid tube that connects air inlet assembly, air exhaust assembly and powerhouse 1004 that houses the battery and control circuit. The battery is chargeable with charger 2103 or battery is bypassed, and everything is powered by charger 2103 as mentioned above. All features described about pillow 2101 used in solution 2100 applies to solution 2200.

Figure 12C:
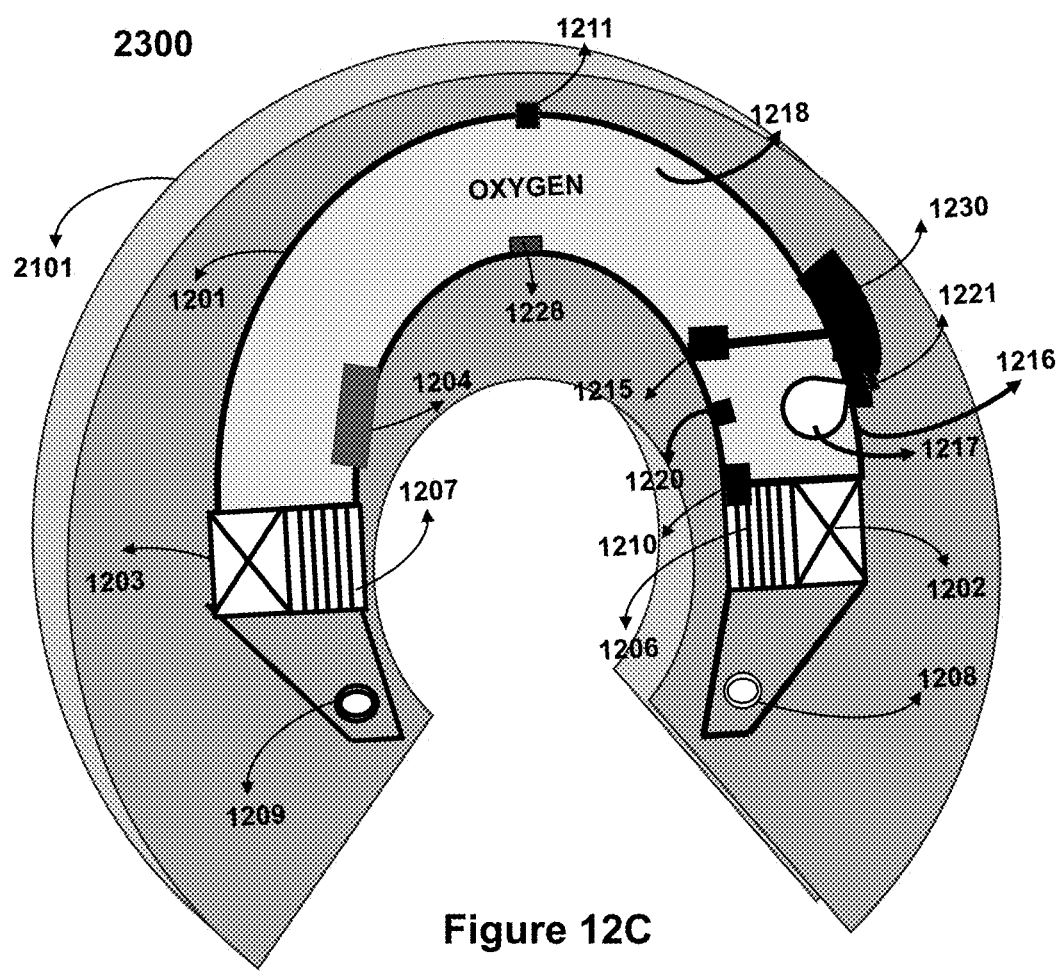
FIG. 12C shows a pillow with an embedded inlet assembly, exhaust assembly, oxygen tank with regulator, battery, and control circuit.

FIG. 12C depicts sleep apnea detection 2300 with pillow 2101. Solution 2300 in addition to all the features of solution 2100 needs to support all or some functions of one of the wearable devices shown in FIGS. 4C, 4E, 4G, 4K, and 4M. Therefore, pillow 2101 also needs to provide means for refilling the oxygen storage 1218 and adjusting regulator 1216. In solution 2300 shown in FIG. 12C all components and functions of wearable device 1800 that is shown in FIG. 4M and explained in detail in paragraph 00165 are used. Pillow 2101 accommodates tube 1201 that houses the battery and control circuit 1204, oxygen storage 1218 with refill valve 1211 and regulator 1216. Therefore, pillow 2101 in addition to all the features and capabilities described in above paragraphs provides provision for refilling the oxygen tank 1218 and air passageway for electric air pump 1230 used by regulator 1216.

The reason for using the wearable device 1800 with oxygen tank shown in FIG. 4M is to mix oxygen with the airflow when AI algorithm detects low oxygen saturation during sleep apnea test. Oxygen saturation's measured data is obtained by control circuit through a biometric device attached to the body of the person under sleep apnea test and used by AI algorithm. Using the measured data from various sensors AI also detects any disturbance in airflow or malfunction of any component of the sleep apnea test setup and alarms the person under the test.

The criteria or threshold for detection of the apnea can be configured in the control circuit. This can be done using external devices that communicate with the embedded device (wired or wireless). Power housing can use a USB port to communicate with external devices or a transceiver to communicate with external devices directly or through IoT network. The occurrence of apnea is detected when a time between two consecutive breath inhales is more than ten seconds or a time between two consecutive breath exhales is more than ten seconds. It is also possible to have other values less or more than ten seconds to determine the occurrence of apnea. This value can be configured in the control circuit by medical staff or the person using the sleep apnea device. The AI algorithm uses the last configured value for its detection of apnea. It is also possible to use other techniques using all the information data collected by the AI algorithm within the CPU of the control circuit to detect apnea.

Another function of pillow 2101 is to mitigate the occurrence of apnea. This is done by vibration or reshaping resulting in changing the shape and size of the pillow. There are several methods to mitigate sleep apnea. In the following paragraphs three practical methods of mitigation without awakening the person under test are explained.

Figure 13A:
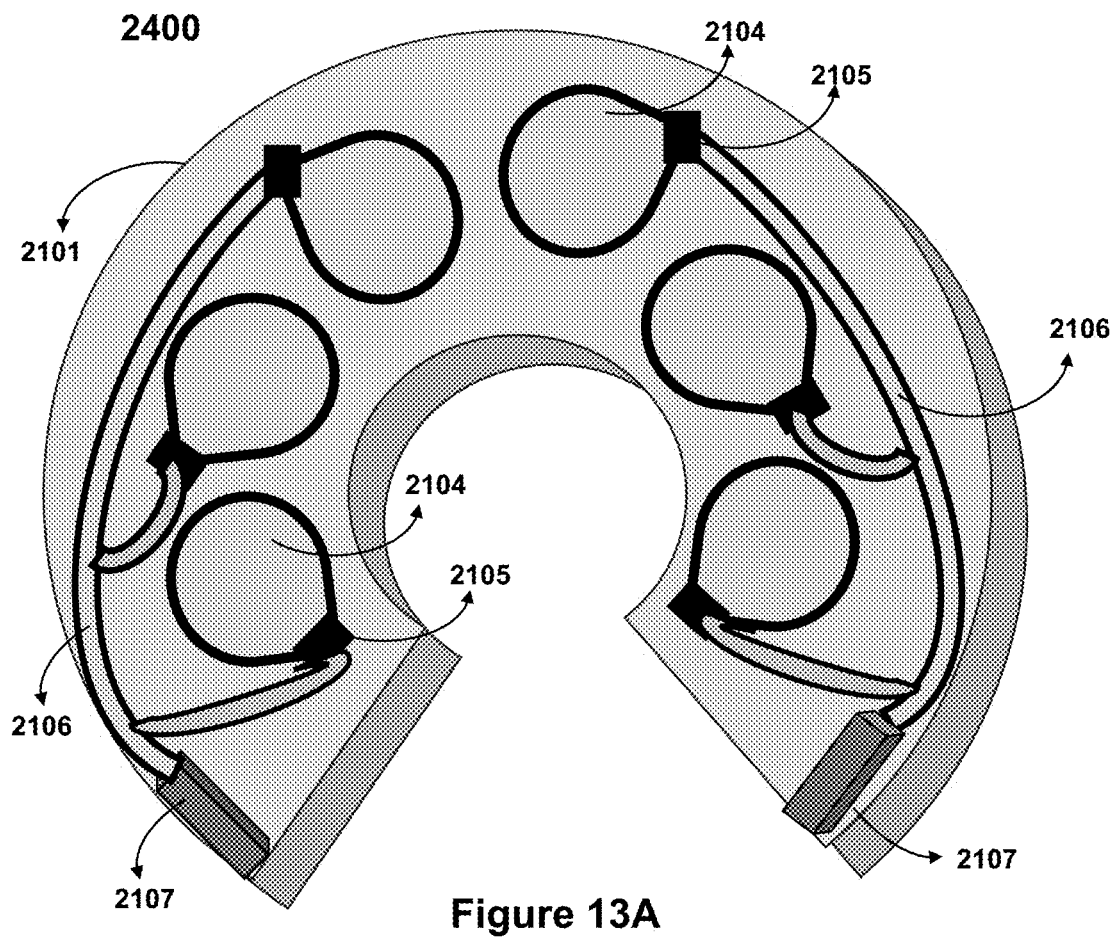
FIG. 13A depicts a pillow with airbags that can be inflated and deflated by an electric air pump.

FIG. 13A shows pillow reshaping method 2400. For this type of reshaping of pillow 2101 airbags that are an integral part of the pillow 2101 are used. Airbags 2104 are located at various locations in pillow 2101 and are inflated and deflated when needed. The inflation and deflation of airbags are done by electric air pump 2107. Air pump 2107 through inflating/deflating tube 2106 and valve 2105 inflates or deflates airbag 2104. Airbags 2104 are embedded at various locations of pillow 2101 and each airbag 2104 has its own valve 2105. The valve 2105 is opened or closed by the AI algorithm in control circuit that resides in powerhouse 2102/1204. When one airbag 2104 is inflated or deflated its valve 2105 is opened and at other times closed. The electric air pump 2107 is installed within pillow 2101 where it does not cause any discomfort for the person (wearer) using the pillow and the air passageway it uses to pull or release air from or to the environment is not blocked. The electric air pump can also be attached to pillow 2101 or part of the external charger 2103.

The control circuit's AI algorithm receives information data from airflow sensors 1305, 1306 and 1307 (as well as oxygen saturation sensor, HRV sensor, and ECG/EKG if needed for further verification) to detect occurrence of apnea. When apnea is detected, then AI algorithm based on configured procedure inflates one or more airbags 2104 to mitigate the apnea. By inflating one or more airbags 2104 the pillow 2101 is reshaped and the position of the head of the person (wearer) under test changes. If apnea occurrence stops, then AI algorithm continues monitoring of the sleep. If apnea does not stop, then AI algorithm has several options to reshape pillow 2101 by totally deflating the airbags that are already inflated and inflate new and different airbags 2104 or reduce the number of already inflated airbags and inflate no new airbags or inflate new airbags based on configured procedure. If there is no configured inflating and deflating procedure for airbags 2104, then AI algorithm can randomly inflate and deflate airbags and by doing so learn the best procedure for inflating and deflating that best mitigates apnea.

Figure 13B:
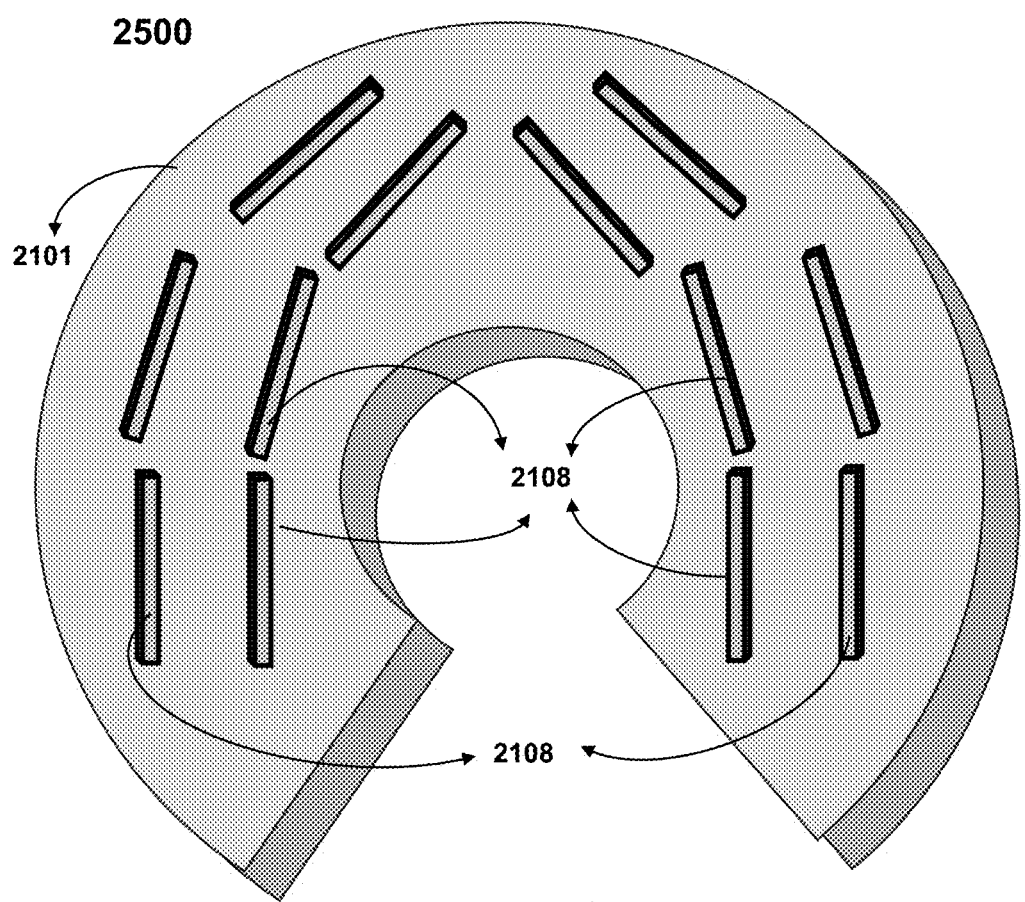
FIG. 13B shows a pillow with expandable polymer pads that can be expanded and contracted by applying voltage.

FIG. 13B shows pillow reshaping method 2500. For this type of reshaping of pillow 2101 expandable polymer pads that are an integral part of the pillow 2101 are used. Expandable polymer pads 2108 are located at various locations in pillow 2101 and are expanded and contracted when needed. Expansion and contraction of the polymer pads is done by applying a voltage across them that is controlled by control circuit's AI algorithm. This process results in reshaping (change of shape and size) of pillow 2101. Expandable polymer pads 2108 are embedded at various locations of pillow 2101. The process of reshaping pillow 2101 to mitigate apnea is like what was described for airbags in paragraph 00223.

Figure 13C:
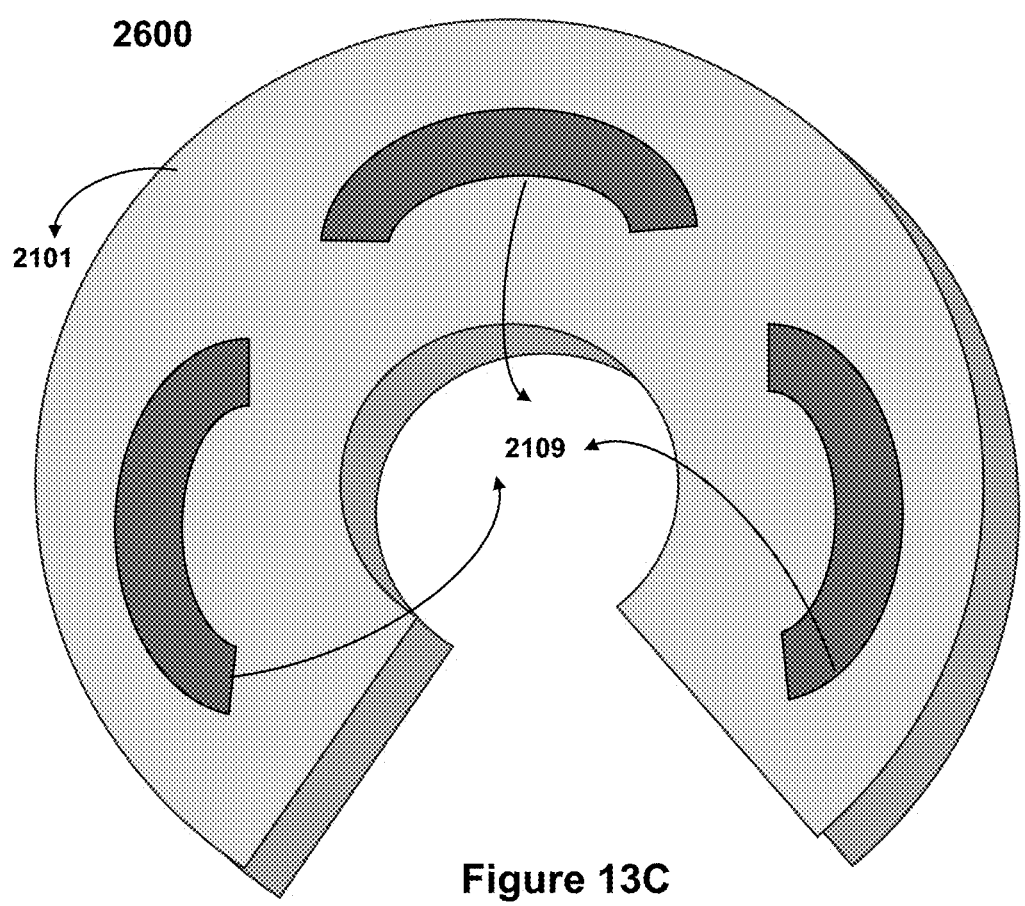
FIG. 13C illustrates a pillow with vibrators.

FIG. 13C shows pillow vibration method 2600. This type of pillow 2101 uses a vibrator to slightly shake the head of the person under the sleep apnea test without waking the person. This technique can help the person under the test move their head. It is possible that this head movement mitigates the apnea. The vibration happens after AI algorithm like other two methods use all or a subset of the measured data and detects apnea. Pillow 2101 uses one or more vibrators. The vibrators are embedded inside the pillow.

The above procedures (explained about FIGS. 13A, 13B, 13C) are also used when airflow in the sleep apnea device is blocked (full or partially) or airflow is disturbed and is abnormal. This scenario happens due to the movement of the person (wearer) using the pillow.

For mitigation of sleep apnea and any sleep apnea device's airflow blockage (full or partial) or disturbance there are certainly other solutions. This application clearly focuses on using a pillow in any shape, size, dimension, and material to mitigate apnea and any airflow blockage (full or partial) or disturbance due to movement of the wearer (person) of pillow 2101. It is also possible to provide multiple solutions in the pillow for mitigation. The pillow can use one or all the methods shown in FIGS. 13A, 13B, and 13C to mitigate apnea. The pillow can use only two of the solutions shown in FIGS. 13A, 13B, and 13C to mitigate apnea. Pillow can use one, two or all the solutions shown in FIGS. 13A, 13B, and 13C in conjunction with one or more other solutions that are not described in this application to mitigate apnea. This also applies for airflow blockage and disturbance.

When most people hear the term robot, they think of a highly advanced, artificially intelligent machine that can do dozens of daily tasks. A robot is defined as an electromechanical device capable of reacting in some way to its environment and making autonomous decisions or actions to achieve a specific task. One of the most important components of a robotic build is the actuator. An actuator is a device that converts energy into physical motion, and most actuators produce rotary or linear motion. Linear actuators are defined by force, rotary actuators are defined by torque.

There are many types of actuators, but the three most common types of actuators are hydraulic, pneumatic, and electric. Hydraulic actuators use compressed oil to cause motion. They are most used in heavy machinery, and they can generate very high force. Pneumatic actuators are very similar to hydraulic actuators. Instead of using compressed oil to cause motion, they use compressed air. Electric actuators use an electric current and magnets.

Materials that have actuating properties are based mainly on polymers. A polymer gel is an electroactive material which differs in various ways from solid polymer materials. The polymer chains in the gel are usually considered to be chemically or physically cross-linked and form a three-dimensional network. The gels also have various actuating modes, such as change of volume due to swelling and de-swelling, symmetric deformation and asymmetric deformation. Various triggers for actuating polymer gels have been described. Triggers are classified into two categories: chemical and physical triggers. An example of a physical trigger is an electrical field, which is one of the most attractive triggers for use.

Electroactive polymers (EAPs) are a class of polymeric materials that can change dimensions when electrically activated. Those polymers exhibit natural muscle-like behaviors due to their operation principle like real muscles and therefore they gained the name of artificial muscles. The EAPs are generally divided into two families operating by fundamentally different principles: (i) electronic EAPs whose volume changes under application of an electric field and (ii) ionic EAPs whose volume changes with a movement of ions within the material. Electronic conducting polymers (ECPs) belong to the ionic one. Their oxidation or reduction gives rise to reversible volume variations.

Dielectric elastomers (as an electronic EAP) can hold their induced displacement while activated under a DC voltage. This allows dielectric polymers to be considered for robotic applications. These types of materials also have high mechanical energy density and can be operated in air without a major decrease in performance. However, dielectric polymers require very high activation fields (>10 V/μm) that are close to the breakdown level.

The activation of ionic polymers, on the other hand, requires only 1-2 volts. They however need to maintain wetness, though some polymers have been developed as self-contained encapsulated activators which allows their use in dry environments. Ionic polymers also have a low electromechanical coupling. They are however ideal for bio-mimetic devices.

EAP materials can be easily manufactured into various shapes due to the ease in processing many polymeric materials, making them very versatile materials. One potential application for EAPs is that they can potentially be integrated into a fluid regulator to control the pressure.

Figure 14A:
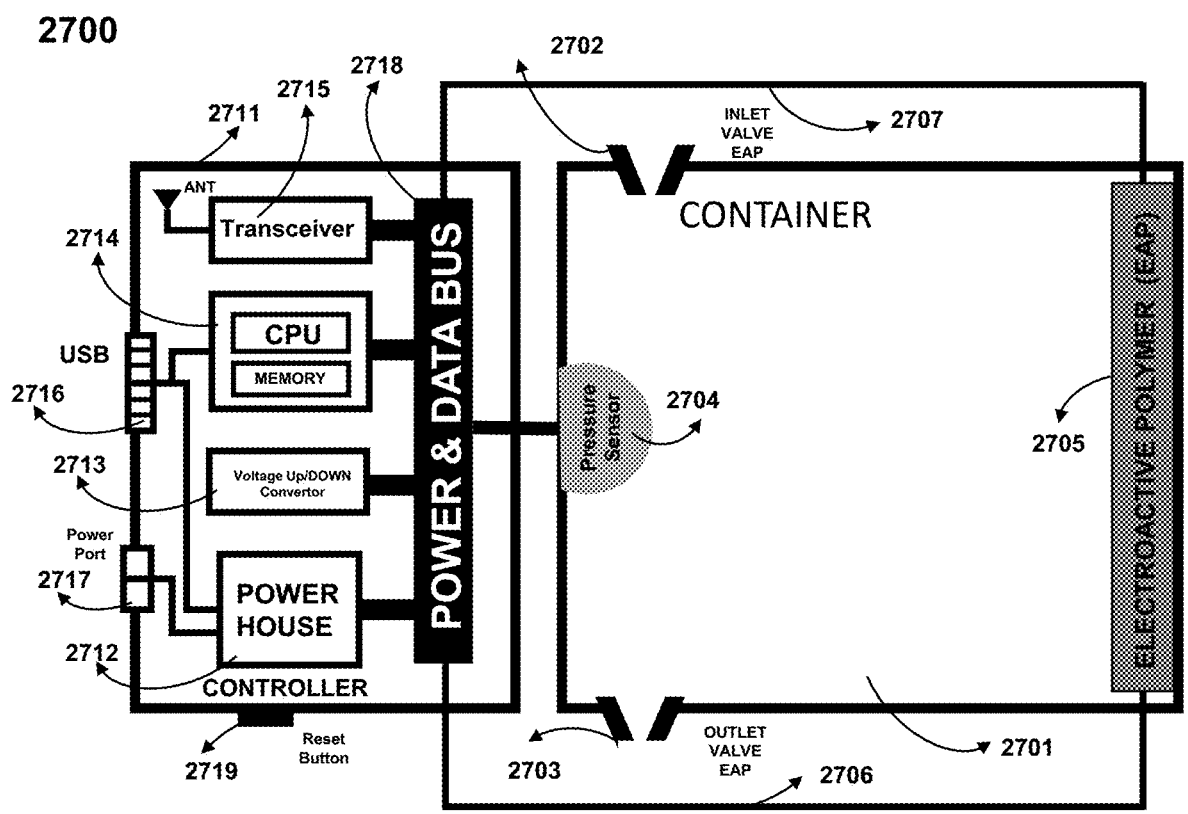
FIG. 14A depicts block diagram of the structure of fluid pressure regulator using EAP.

FIG. 14A depicts the block diagram structure of a fluid regulator 2700. Fluid regulator 2700 among other things include a container 2701 that receives the fluid through fluid inlet valve 2702 and after adjusting the pressure of the incoming fluid release it through fluid outlet valve 2703. The fluid regulator uses pressure sensor 2704 to measure the pressure of the fluid within the container 2701 and sends the measured data to controller 2711 for analysis. Controller 2711 based on preconfigured thresholds determines when to adjust the pressure of the fluid within the container 2701 by activating the electroactive polymer (EAP) 2705 within the container 2701 by applying a voltage to the EAP 2705 using power lines 2706 and 2707. The adjustment is done by changing the size and volume of the EAP 2705, The fluid can be water, oil, gas, air, oxygen, and any other type of fluids. The physical structure of the container 2701, the components (2704, and 2705) within the container 2701, and the inlet/outlets valves (2702 and 2703) are tailored towards the fluid it is being used for.

Inlet valve 2702 and outlet valve 2703 can use EAP to control the fluid (flow and pressure) entering and exit container 2701. The EAP used by inlet valve 2701 and outlet valve 2703 when activated by a voltage controlled by controller 2711 change size, deform, and bend to adjust the fluid flow and/or pressure in and out of container 2701.

The controller 2711 that is an integral part of the regulator 2700 is attached to the container 2701 or is a standalone component that is connected to the container 2701 by a cable that carries data and required voltage for the EAP 2705 and EAP used in inlet valve 2702 and outlet valve 2703. The controller 2711 communicates to an external device by a USB (universal serial port) 2716 or acts as an Internet of things (IoT) device and wirelessly communicates with an external device directly or through an IoT network. Controller 2711 can also uses USB 2716 as a power port. Controller 2711 comprises a powerhouse 2712 that houses rechargeable batteries, a voltage up and down convertor (regulator) 2713, a central processing unit (CPU) with memory 2714, a wireless transceiver (that can facilitate IoT communication) 2715, a power and data bus 2718 that connects all components of the controller and provides power and data exchange, a redundant power port 2717 to provide power for the powerhouse 2712 in case USB 2716 is not used, and a reset button 2719.

Controller 2711 obtains its power from USB 2716 or power port 2717. The rechargeable batteries in powerhouse 2712 are charged through USB 2716 or power port 2717. Controller 2711 can also use an external charger to provide the voltage that voltage up and down convertor (regulator) 2713 requires. The output voltage of the powerhouse 2712 is applied to voltage up or down convertor 2713 to regulate the voltages that are required for EAP 2705, inlet valve 2702 EAP, outlet valve 2703 EAP, CPU/memory 2714, pressure sensor 2704, wireless transceiver 2715, and any other components (LED indicators, alarm devices, etc.) that are used by fluid regulator 2700. All the voltages for various components of fluid regulator are supplied through power and data bus 2718 or other methods of power distribution. Powerhouse 2712 uses sensors to monitor its operation and send measured data to CPU and memory 2714. Controller 2711 uses various sensors to measure different operation parameters for CPU/memory 2704 to be used by its algorithm.

Controller 2711 uses voltage up/down convertor 2713 to provide various voltages for various components that are used by fluid regulator 2700. These voltages are distributed by power and data bus 2718. The voltages depend on the application of the fluid regulator and the components that are used for these applications. Voltage up conversion is needed for EAP 2705, inlet valve 2702 EAP, and outlet valve 2703 EAP. There are applications that use electroactive polymers that need high voltage and voltage up/down converter provides the required voltage. The voltage up/down converter 2713 uses sensors to monitor its operation and send measured data to CPU and memory 2714.

CPU/memory 2714 obtains measured information data from pressure sensor 2704, other sensors used internal and external to fluid regulator 2700, and various sensors from external devices that are connected to the fluid regulator 2700. CPU/memory 2714 also receives information data from external devices (smart phone, tablet, computer, etc.), biometric devices, external IoT networks, wireless fidelity (WiFi) network, and any other proprietary wireless network through wireless transceiver 2715. CPU/memory 2714 also shares information data with external devices wirelessly or through USB 2716.

Figure 14B:
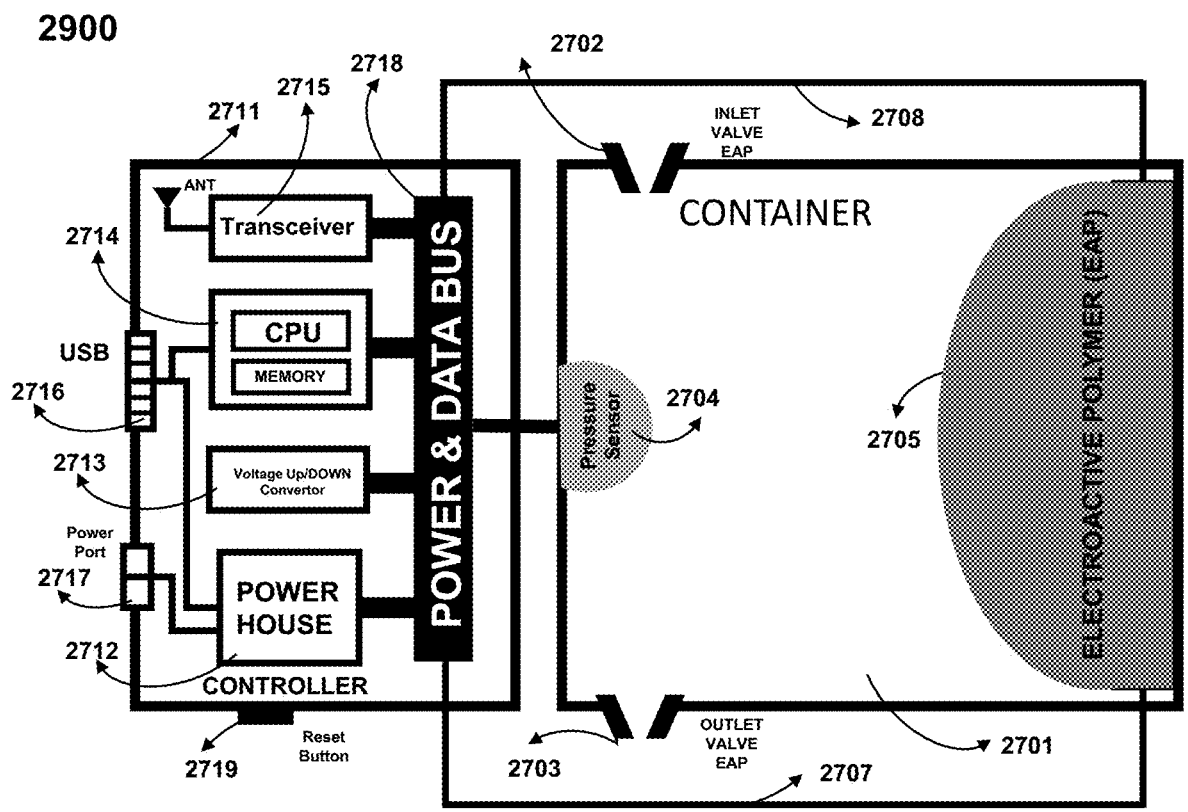
FIG. 14B shows block diagram of the structure of fluid pressure regulator when EAP activated

CPU/memory 2714 obtains configuration data that includes all data required for operation of fluid regulator 2700 at power up as well as during operation of fluid regulator 2700. CPU/memory 2714 uses an artificial intelligence (AI) algorithm to analyze all the information data (measured or/and supplied) to control the operation of fluid regulator 2700. The AI algorithm uses pressure sensor 2704 real time measured data as well as received information data from external devices (wireless or through USB 2716), devices that are attached to fluid regulator 2700, and biometric devices used in certain application of fluid regulator 2700 to control the fluid pressure within container 2701 and amount of fluid enter or exit the container. This is shown in FIG. 14B. EAP2705 is activated and its size and volume are increased by controller AI algorithm by applying the required voltage to adjust the fluid (water, oil, gas, air, oxygen. Etc.) within container 2701 to the pressure specified by configuration information data saved in the controller 2711 or real time determined by the AI algorithm executed in CPU/memory 2714 based on all measured information data and received information data described above. The AI algorithm also determines the voltage needed to apply to inlet valve 2702 EAP and outlet valve 2703 EAP. The AI algorithm using all information data described earlier determines to activate all the EAPs (inlet valve EAP, outlet valve EAP, and EAP 2705) or subset of all EAPS. The information data controller receives from external devices or networks can also be various commands to perform certain functions. When controller 2711 is not an integral part or attached to the container 2701 a cable that carries all the voltages and data is used between controller 2711 and container 2701.

Figure 14C:
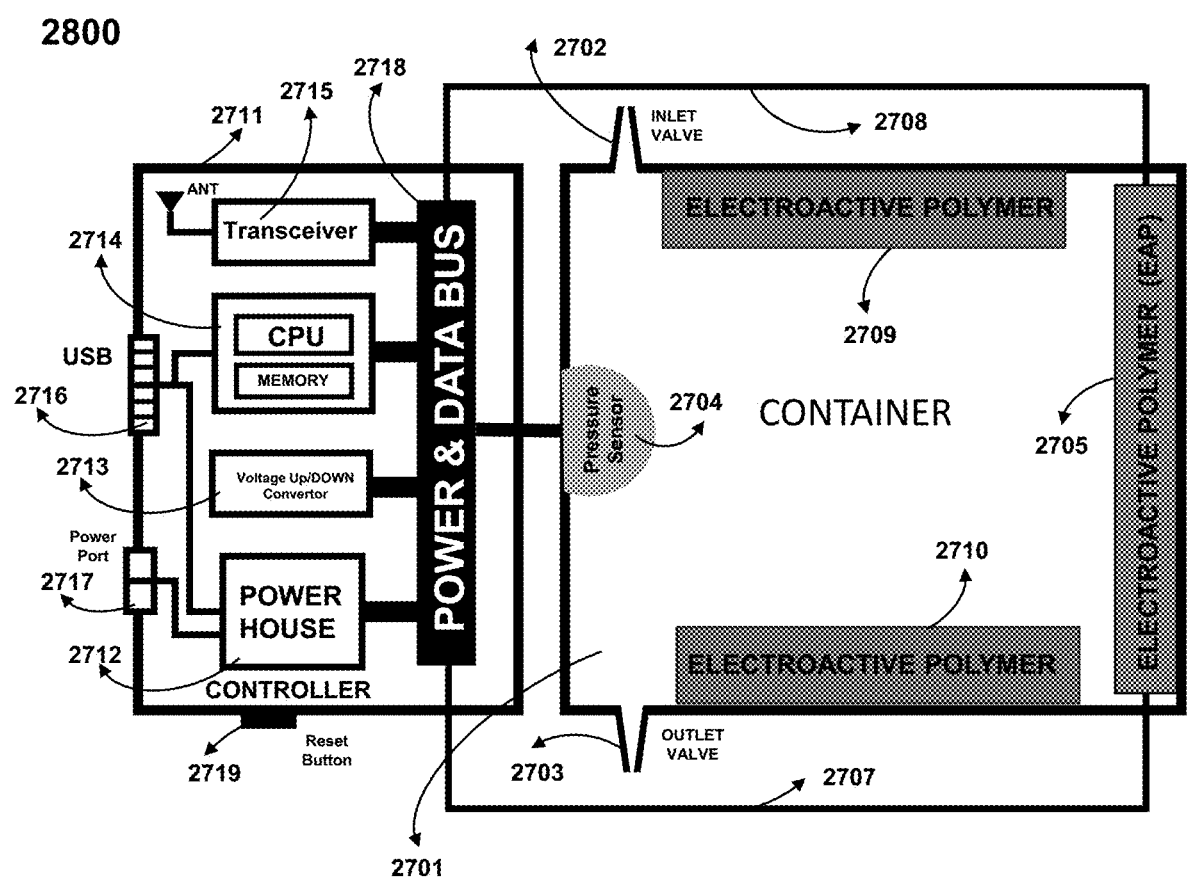
FIG. 14C depicts block diagram of the structure of fluid pressure regulator using multiple EAP.

Fluid regulator 2700 can use multiple EAPs (2705, 2708, 2709) located at different locations of the container 2701 as shown in FIG. 14C. The same voltage can be used for all EAPs, or each EAP can have its own voltage when activated. The voltages are produced in voltage up/down converter 2713 and carried by power and data bus 2718 to various EAPs.

Various embodiments are thus described. While embodiments have been described, it should be appreciated that the embodiments should not be construed as limited by such description, but rather construed according to the following claims.

The invention claimed is:

1. A sleep apnea device comprising:
a pillow;
a face mask;
a first air tube; and
a second air tube;
said pillow comprising:
an embedded reshaping device to reshape said pillow;
an embedded device comprising:
an inlet assembly that receives an air from an environment by a first fan, filters said air by a first filter before releasing it into said face mask through an outlet port;
an exhaust assembly that receives said air that is contaminated from an interior of said face mask through an inlet port by a second fan and filters it by a second filter before releasing it to said environment;
an airflow sensor located in an airflow path of said sleep apnea device to measure a real time airflow;
a power housing to hold a battery, and a control circuit;
said face mask is connected to said embedded device inside said pillow by said first air tube that receives said air from said inlet assembly for a breath inhale and said second air tube that delivers said air that is contaminated due to a breath exhale to said exhaust assembly;
said control circuit uses said real time airflow data obtained by said airflow sensor to detect occurrence of an apnea;
said control circuit after detection of at least one of said apnea, and a blockage of said airflow path activates said embedded reshaping device to reshape said pillow.

2. The sleep apnea device of claim 1, wherein said control circuit uses said real time airflow data measured by said airflow sensor to detect at least one of a time between two consecutive said breath inhales that is more than ten seconds, and a time between two consecutive said breath exhales that is more than ten seconds as occurrence of said apnea.

3. The sleep apnea device of claim 2, further said control circuit uses an artificial intelligence (AI) algorithm executed in a central processing unit (CPU) to detect said apnea or said blockage of said airflow path and activate said embedded reshaping device to mitigate said apnea or said blockage of said airflow path.

4. The sleep apnea device of claim 1, wherein said embedded reshaping device is at least one of an expandable polymer pad, a device with vibrating motion that causes reshaping, and an airbag.

5. The sleep apnea device of claim 4, further said reshaping is done by an inflating or a deflating of said airbag.

6. The sleep apnea device of claim 5, further said inflating and said deflating of said airbag is done by an electric air pump embedded in said pillow.

7. The sleep apnea device of claim 4, further said reshaping is done by an expanding or a contracting of said expandable polymer pad.

8. The sleep apnea device of claim 7, further said expanding or said contracting of said expandable polymer pad is done by applying a voltage to it.

9. The sleep apnea device of claim 1, wherein said embedded device has an oxygen tank with a regulator.

10. The sleep apnea device of claim 9, further said regulator receives an oxygen from said oxygen tank, adjusts a pressure of said oxygen before injecting it into said inlet assembly to be mixed with said air that is filtered by said first filter.

11. The sleep apnea device of claim 10, wherein said regulator comprises of an inlet valve to receive said oxygen, a container that holds said oxygen, an outlet valve, and a pressure sensor inside said container to measure said pressure of said oxygen within said container and deliver it to said control circuit.

12. The sleep apnea device of claim 11, further said outlet valve delivers said oxygen that is inside said container after adjustment of said pressure to said inlet assembly under control of said control circuit.

13. The sleep apnea device of claim 1, wherein said embedded device, and said embedded reshaping device are powered by at least one of said battery, and an external charger connected to said power housing.

* * * * *